(12) United States Patent
Keith et al.

(10) Patent No.: US 8,637,520 B2
(45) Date of Patent: Jan. 28, 2014

(54) SUBSTITUTED PYRIDYL AMIDE COMPOUNDS AS MODULATORS OF THE HISTAMINE $H_3$ RECEPTOR

(75) Inventors: John M. Keith, San Diego, CA (US); Michael A. Letavic, San Diego, CA (US); Kiev S. Ly, San Diego, CA (US); Neelakandha S. Mani, San Diego, CA (US); John E. Mills, Hatfield, PA (US); Chennagiri R. Pandit, San Diego, CA (US); Frank J. Villani, Perkasie, PA (US); Hua Zhong, Maple Glen, PA (US)

(73) Assignee: Janssen Pharmaceutica NV, Beerse (BE)

( * ) Notice: Subject to any disclaimer, the term of this patent is extended or adjusted under 35 U.S.C. 154(b) by 441 days.

(21) Appl. No.: 12/828,883

(22) Filed: Jul. 1, 2010

(65) Prior Publication Data

US 2010/0267701 A1 Oct. 21, 2010

Related U.S. Application Data

(63) Continuation of application No. 11/753,607, filed on May 25, 2007, now Pat. No. 7,777,031.

(60) Provisional application No. 60/823,108, filed on Aug. 22, 2006, provisional application No. 60/803,407, filed on May 30, 2006.

(51) Int. Cl.
*A61K 31/496* (2006.01)
*C07D 401/06* (2006.01)

(52) U.S. Cl.
USPC ...... 514/253.13; 544/336; 544/358; 544/365; 540/553; 514/252.12

(58) Field of Classification Search
USPC ........ 544/336, 358, 365; 514/252.12, 253.13; 540/553
See application file for complete search history.

(56) References Cited

U.S. PATENT DOCUMENTS

| | | | |
|---|---|---|---|
| 3,538,106 A | 11/1970 | Hoffmann et al. | |
| 4,792,547 A | 12/1988 | Itoh et al. | |
| 5,384,305 A | 1/1995 | Foster et al. | |
| 5,780,393 A | 7/1998 | Newton | |
| 6,201,007 B1 | 3/2001 | Ito et al. | |
| 6,339,045 B1 | 1/2002 | Kanno et al. | |
| 6,399,607 B1 | 6/2002 | Welch et al. | |
| 6,645,990 B2 | 11/2003 | Askew et al. | |
| 7,423,147 B2 | 9/2008 | Carruthers et al. | |
| 7,777,031 B2 * | 8/2010 | Mani et al. | 540/553 |
| 2003/0125339 A1 | 7/2003 | Chen et al. | |
| 2004/0014744 A1 | 1/2004 | Haviv et al. | |
| 2004/0019039 A1 | 1/2004 | Dorwald et al. | |
| 2004/0110746 A1 | 6/2004 | Apodaca et al. | |
| 2004/0224968 A1 | 11/2004 | Seidelmann et al. | |
| 2006/0025404 A1 | 2/2006 | Ancliff et al. | |
| 2006/0052597 A1 | 3/2006 | Best et al. | |
| 2006/0178375 A1 | 8/2006 | Ohtake et al. | |
| 2007/0066821 A1 | 3/2007 | Allison et al. | |
| 2007/0167435 A1 | 7/2007 | Mutahi et al. | |
| 2007/0219240 A1 | 9/2007 | Cole et al. | |
| 2007/0281923 A1 | 12/2007 | Keith et al. | |
| 2008/0045507 A1 | 2/2008 | Allison et al. | |

FOREIGN PATENT DOCUMENTS

| | | |
|---|---|---|
| CA | 1051888 A1 | 4/1979 |
| DE | 817911 | 10/1951 |
| DE | 1902694 A1 | 9/1969 |
| DE | 2514334 A1 | 10/1987 |
| EP | 0089153 A2 | 9/1983 |
| EP | 0134096 A2 | 3/1985 |
| EP | 0143630 A2 | 6/1985 |
| EP | 0488474 A1 | 6/1992 |
| EP | 1388535 A1 | 2/2004 |
| EP | 1396487 A1 | 3/2004 |
| JP | 44-20347 B | 9/1969 |
| JP | 46-37595 B | 11/1971 |
| JP | 6-306051 | 11/1994 |
| JP | 2005 502623 A | 1/2005 |
| JP | 2009 521448 A | 6/2009 |
| WO | WO 84/04304 A1 | 11/1984 |
| WO | WO 00/50391 A1 | 8/2000 |
| WO | WO 00/76984 A2 | 12/2000 |
| WO | WO 01/85715 A2 | 11/2001 |
| WO | WO 03/004480 A2 | 1/2003 |
| WO | WO 2003 004480 A2 | 1/2003 |
| WO | WO 03/037869 A1 | 5/2003 |
| WO | WO 03/037891 A1 | 5/2003 |
| WO | WO 03/066604 A2 | 8/2003 |
| WO | WO 03/078398 A1 | 9/2003 |
| WO | WO 03/082205 A2 | 10/2003 |
| WO | WO 03/092686 A1 | 11/2003 |
| WO | WO 2004/018428 A1 | 3/2004 |
| WO | WO 2004/054973 A2 | 7/2004 |
| WO | WO 2005/007644 A1 | 1/2005 |

(Continued)

OTHER PUBLICATIONS

Arrang, J.-M. et al. Auto-Inhibition of Brain Histamine Release Mediated by a Novel Class ($H_3$) of Histamine Receptor. Nature, 1983, 302, 832-837.

Barbier, A.J. et al. Acute Wake-promoting Actions of JNJ-5207852, a Novel, Diamine-based $H_3$ Antagonist. Br. J. Pharmacol. 2004, 143, 649-661.

Barnes, J.C. et al. The Selective Histamine $H_3$ Receptor Antagonist Thioperamide Improves Cognition and Enhances Hippocampal Acetylcholine Release In Vivo. Soc. Neurosci. Abstr. 1993, 19, 1813.

Bodroux Reaction. In Merck Index, 12$^{th}$ ed.; Budavari, S., Ed.; Merck & Co., Inc.: Whitehouse Station, NJ, 1996; p. ONR-12.

Bonaventure, P. et al. Histamine $H_3$ Receptor Antagonists: From Target Identification to Drug Leads. Biochem. Pharm. 2007, 73, 1084-1096.

(Continued)

*Primary Examiner* — Golam M M Shameem
(74) *Attorney, Agent, or Firm* — Michael J. Atkins

(57) ABSTRACT

Certain substituted pyridyl amide compounds are histamine $H_3$ receptor modulators useful in the treatment of histamine $H_3$ receptor-mediated diseases.

4 Claims, No Drawings

(56) References Cited

FOREIGN PATENT DOCUMENTS

| WO | WO 2005/009976 A1 | 2/2005 |
|---|---|---|
| WO | WO 2005/023247 A1 | 3/2005 |
| WO | WO 2005/040144 A1 | 5/2005 |
| WO | WO 2007 075629 A2 | 7/2007 |

OTHER PUBLICATIONS

Chen, Z. Effect of Histamine $H_3$-Receptor Antagonist Clobenpropit on Spatial Memory of Radial Maze Performance in Rats. Acta Pharmacol. Sin. 2000, 21(10), 905-910.

Fox, G.B. et al. Effects of Histamine $H_3$ Receptor Ligands GT-2331 and Ciproxifan in a Repeated Acquisition Avoidance Response in the Spontaneously Hypertensive Rat Pup. Behav. Brain Res. 2002, 131(1-2), 151-161.

Lamberti, C. et al. Antidepressant-like Effects of Endogenous Histamine and of Two Histamine $H_1$ Receptor Agonists in the Mouse Forced Swim Test. Br. J. Pharmacol. 1998, 123(7), 1331-1336.

Letavic, M.A. et al. Recent Medicinal Chemistry of the Histamine $H_3$ Receptor. Prog. Med. Chem. 1996, 44, 181-206.

Leurs, R. et al.: The medicinal chemistry and therapeutic potentials of ligands of the histamine H3 receptor; Progress in Drug Research (1995) 45: 107-165.

Machidori, H. et al. Zucker Obese Rats: Defect in Brain Histamine Control of Feeding. Brain Res. 1992, 590, 180-186.

Miyazaki, S. et al. Effects of Thioperamide, A Histamine $H_3$-Receptor Antagonist, on a Scopolamine-Induced Learning Deficit Using an Elevated Plus-Maze Test in Mice. Life Sci. 1995, 57(23), 2137-2144.

Miyazaki, S. et al. Effects of Thioperamide on the Cholinergic System and the Step-through Passive Avoidance Test in Mice. Meth. Find. Exp. Clin. Pharmacol. 1995, 17(10), 653-658.

Morisset, S. et al. High Constitutive Activity of Native $H_3$ Receptors Regulates Histamine Neurons in Brain. Nature 2000, 408, 860-864.

Orsetti, M. et al. Histamine $H_3$-Receptor Antagonism Improves Memory Retention and Reverses the Cognitive Deficit Induced by Scopolamine in a Two-Trial Place Recognition Task. Behav. Brain Res. 2001, 124(2), 235-242.

Panula, P. et al. Significant Changes in the Human Brain Histaminergic System in Alzheimer's Disease. Soc. Neurosci. Abstr. 1995, 21, 1977.

Perez-Garcia, C. et al. Effects of Histamine $H_3$ Receptor Ligands in Experimental Models of Anxiety and Depression. Psychopharmacology 1999, 142(2), 215-220.

Schlicker, E. et al. The Moderate Affinity of Clozapine at $H_3$ Receptors is Not Shared by its Two Major Metabolites and by Structurally Related and Unrelated Atypical Neuroleptics. Naunyn-Schmiedeberg's Arch. Pharmacol. 1996, 353, 290-294.

Searles, Jr., S. et al. β-Priopiolactam and the Use of Mesityl Grignard Reagent in the Breckpot β-Lactam Syntheses. Chem. Ind. (London) 1964, 51, 2097.

Shono, T. et al. Electroorganic Chemistry. 82. β-Amino Acid Esters from α-Methoxycarbamates and Ketene Silyl Acetals; Cyclization to β-Lactams. J. Org. Chem. 1984, 49, 1056-1059.

Stark, H. et al. Developments of Histamine $H_3$-Receptor Antagonists. Drugs Future 1996, 21(5), 507-520.

Yokoyama, H. et al. Effect of Thioperamide, a Histamine $H_3$ Receptor Antagonist, on Electrically Induced Convulsions in Mice. Eur. J. Pharmacol. 1993, 234, 129-133.

PCT International Search Report dated Dec. 6, 2007 for International PCT Application No. PCT/US2007/069723.

Akhundov, R.A. et al.: "Synthesis and Psychotropic Activity of Amides of 2-Aminonicotinic Acid", Khimiko-Farmatsevticheskki Zhurnal, vol. 20, No. 1 (1986) pp. 48-50, Rumoscow, Database Beilstein 1993, Database Accession No. 5702704 (CNR) BRN: 5598995, 5632883, 5764929, 5774681, (XP002344011).

Ash, A.S.F et al.: Receptors Mediating Some Actions of Histamine. Br. J. Pharmac. Chemother. 1966, 27, 427-439.

Bagshawe, K.D.: "Antibody-Directed Enzyme Prodrug Therapy: A Review"; Drug Devel. Research (1995) 34: 220-230.

Berge, S.M. et al.: "Pharmaceutical Salts"; J. of Pharmaceutical Sciences (1977) 66(1): 1-19.

Bertolini, G. et al.: "A New Rational Hypothesis for the Pharmacophore of the Active Metabolite of Leflunomide, A Potent Immunosuppressive Drug"; J. Med. Chem. (1997) 40: 2011-2016.

Black, J.W. et al.: Definition and Antagonism of Histamine $H_2$-Receptors. Nature 1972, 236, 385-390.

Bodor, N.: Novel Approaches to the Design of Safer Drugs: Soft Drugs and Site-Specific Chemical Delivery Systems; Advances in Drug Research (1984) 13: 255-331.

Buchi, Von J. et al.: "Syntheses of Some 2-Dialkylaminoalkoxy-6-Alkylaminopyridines and 2-Dialkylaminoalkylamino-6-Alkoxypyridines", Helvetica Chimica Acta., vol. 48, No. 5 (1965) pp. 1216-1219, Chverlag Helvetica Chimica Acta. Basel, (XP009050917). (Look to the Figures and Tables Found Throughout the Article for Relevance.).

Fleisher, D. et al.: "Improved Oral Drug Delivery: Solubility Limitations Overcome by the Use of Prodrugs"; Adv. Drug Del. Rev. (1996) 19: 115-130.

Foks et al.: "Pyrazine Derivatives. III. Synthesis and Tuberculostatic Activity of 6-(N-Methyllamino)-Pyrazine-2-Carboxylic Acid Derivatives", Polish Journal of Pharmacology and Pharmacy, vol. 26, No. 5 (1974) pp. 537-543 (XP002355523)—Chemical Abstracts, Database Accession No. 82:43345 (DN) RN 54409-12-0.

Foks et al.: "Aminomethylation of Pyridine- and Pyrazinecarbothioamides. V. 6-Chloro- and 6-Aminopyrazine-2-Carbothioamides in the Mannich Reaction", Acta Poloniae Pharmaceutica, vol. 33, No. 1 (1976) pp. 55-65 (XP002355524)—Chemical Abstracts, Database Accession No. 86:72575 (DN).

Ganellin, C.R. et al.: Synthesis of Potent Non-Imidazole Histamine $H_3$-Receptor Antagonists. Arch. Pharm. Pharm. Med. Chem. (Weinheim, Ger.) 1998, 331, 395-404.

Highfield, J.A. et al.: "Preparative, Physico-Chemical and Cytotoxicity Studies of Prodrugs Activated in Hyposiz to Give Metal-Binding Analogues of Bleomycin", Journal of the Chemical Society, Perkin Transactions 1, vol. 16 (1999) pp. 2343-2352, GB Chemical Society, Letchworth, (XP002337176).

Ichinose, M. et al.: Histamine $H_3$-Receptors Modulate Nonadrenergic Noncholinergic Neural Bronchoconstriction in Guinea-Pig In Vivo. Eur. J. Pharmacol. 1989, 174(1), 49-55.

Imamura, M. et al.: Unmasking of Activated Histamine $H_3$-Receptors in Myocardial Ischemia: Their Role as Regulators of Exocytotic Norepinephrine Release. J. Pharmacol. Exp. Ther. 1994, 271(3), 1259-1266.

Krause et al.: "Medicinal Chemistry of Histamine H3 Receptor Agonists"; The Histamine H3 Receptor—A Target for New Drugs; Leurs, R. and Timmerman, H., (Eds.), Elsevier, (1998): 175-196.

Lin, J-S. et al.: Involvement of Histaminergic Neurons in Arousal Mechanisms Demonstrated With $H_3$-Receptor Ligands in the Cat. Brain Res. 1990, 523, 325-330.

Linney, I.D. et al.: Design, Synthesis, and Structure-Activity Relationships of Novel Non-Imidazole Histamine $H_3$ Receptor Antagonists. J. Med. Chem. 2000, 43(12), 2362-2370.

Lovenberg, T.W. et al.: Cloning and Functional Expression of the Human Histamine $H_3$ Receptor. Mol. Pharmacol. 1999, 55(6), 1101-1107.

MacDonald, S.J.F. et al.: Discovery of Further Pyrrolidine Trans-Lactams as Inhibitors of Human Neutrophil Elastase (HNE) With Potential as Development Candidates and the Crystal Structure of HNE Complexed With an Inhibitor (GW475151). J.Med.Chem. 2002, 45(18), 3878-3890.

Mase, T. et al.: Synthesis of Muscarinic Receptor Antagonist Via a Diastereoselective Michael Reaction, Selective Deoxyfluorination and Metal-Halogen Exchange Reaction. J. Org. Chem. 2001, 66, 6775-6786.

McLeod, R.L. et al.: Antimigraine and Sedative Activity of SCH 50971: A Novel Orally-Active Histamine $H_3$ Receptor Agonist. Soc. Neurosci. Abstr. 1996, 22, 2010.

Monti, J.M. et al.: Effects of Selective Activation or Blockade of the Histamine $H_3$ Receptor on Sleep and Wakefulness. Eur. J. Pharmacol. 1991, 205(3), 283-287.

Ortho-McNeil Pharmaceutical, Inc.: (WO03050099); "Phenylalkynes to Treat Histamine-Mediated Conditions", Expert Opinion on Therapeutic Patents, vol. 13, No. 11 (2003) pp. 1759-1762, (XP002337280).

(56) References Cited

OTHER PUBLICATIONS

Patani, G.A. et al.: Bioisosterism: A Rational Approach in Drug Design; Chem. Rev. (1996) 96: 3147-3176.
Pavia et al.: "6-Alkoxy-*N,N*-Disubstituted-2-Pyridinamines as Anticonvulsant Agents", *Journal of the American Chemical Society*, vol. 30, No. 7 (1987) pp. 1210-1214, US American Chemical Society, Washington DC, (XP002337175).
Phillips, J.G. et al.: Medicinal Chemistry of Histamine $H_3$ Receptor Antagonists. *In the Histamine $H_3$ Receptor—A Target for New Drugs*. Leurs, R.; Timmerman, H., Eds.; Elsevier: 1998; pp. 197-222.
Reiner, J.E. et al.: Non-Covalent Thrombin Inhibitors Featuring $P_3$-Heterocycles With $P_1$-Monocyclic Arginine Surrogates. *Bioorg. Med. Chem. Lett.* 2002, 12, 1203-1208.
Robinson, R.P. et al.: "Discovery of the Hemifumarate and (A-L-Alanyloxy)Methyl Ether as Prodrugs of an Antirheumatic Oxindole: Prodrugs for the Enolic OH Group"; J. Med. Chem. (1996) 39: 10-18.
Shan, D. et al.: "Prodrug Strategies Based on Intramolecular Cyclization Reactions"; J. of Pharm. Sciences (Jul. 1997) 86(7): 765-767.
Stark, H.: "Recent Advances in Histamine $H_3/H_4$ Receptor Ligands", *Expert Opinion on Therapeutic Patents*, vol. 13, No. 6 (2003) pp. 851-865, Ashley Publications, GB, ISSN: 1354-3776, (XP002298271).
Thunus et al.: "Quelques Derives de la (Methyl-4, Peperazinyl-1)-2 Pyridine Substituee en 3", *European Journal of Medicinal Chemistry*, vol. 9, No. 1 (1974) pp. 55-58, Freditions Scientifique Elsevier, Paris, (XP009050898). (Look to the Figures and Tables Found Throughout the Article for Relevance.).
Tozer, M.J. et al.: Histamine $H_3$ Receptor Antagonists. *Exp. Opin. Ther*. Patents 2000, 10(7), 1045-1055.
Turner, S.C. et al.: A New Class of Histamine $H_3$-Receptor Antagonists: Synthesis and Structure-Activity Relationships of 7,8,9,10-Tetrahydro-6H-Cyclohepta[B]Quinolones. *Bioorg. Med. Chem. Lett.* 2003, 13(13), 2131-2135.
Vippagunta, S. R. et al: "Crystalline Solids"; Advanced Drug Delivery Reviews (2001) 48: 3-26.
Walczynski, K. et al.: Non-Imidazole Histamine $H_3$ Ligands. Part I. Synthesis of 2-(1-Piperazinyl)- and 2-(Hexahydro-1H-1,4-Diazepin-1-YL)Benzothiazole Derivatives as $H_3$-Antagonists With $H_1$ Blocking Activities. *FARMACO* 1999, 54, 684-694.
Walczynski, K. et al.: Non-Imidazole Histamine H3 Ligands, Part 2: New 2-Substituted Benzothiazoles as Histamine $H_3$ Antagonists. Arch. Pharm. Pharm. Med. Chem. (Weinheim, Ger.) 1999, 332, 389-398.
Bundgaard Design of Prodrugs Ed H. Bundgaard Elsevier 1985.
Celanire et al "Histamine H3 Receptor Antagonists Reach Out for the Clinic" Drug Discovery Today 2005 vol. 10 (23/24) pp. 1613-1627.
Hancock et al "The Challenge of Drug Discovery of a CPCR Target: Analysis of Preclinical Pharmacology of Histamine H3 Antagonists/Inverse Agonists" Biochem Pharmacol 2006 vol. 71 pp. 1103-1113.
Larsen et al Design and Application of Prodrugs, Drug Design and Development Krogsgaard-Larsen et al., Eds., Harwood Academic Publishers 1991.
Leurs et al The Histamine H3 Receptor a Target for New Drugs Leurs R and Timmerman H Eds Elsevier 1998.
Borisi et al "Systematic Discovery Of multicomponent Therapeutics" PNAS 2003 vol. 100(13) pp. 7977-7982.
Berlin et al "Recent Advances in the Development of Histamine H3 Antgonists" Expert Opinion in Therapeutic Patents 2007 vol. 17(6) pp. 675-687.

\* cited by examiner

SUBSTITUTED PYRIDYL AMIDE COMPOUNDS AS MODULATORS OF THE HISTAMINE H₃ RECEPTOR

CROSS REFERENCE TO RELATED APPLICATIONS

This application is a continuation of U.S. Ser. No. 11/753,607 filed on May 25, 2007, now U.S. Pat. No. 7,777,031 which claims the benefit under 35 USC §119(e) of the following provisional applications: U.S. Ser. No. 60/823,108 filed on Aug. 22, 2006 and U.S. Ser. No. 60/803,407 filed on May 30, 2006. The complete disclosures of the aforementioned related U.S. patent applications are hereby incorporated herein by reference for all purposes.

FIELD OF THE INVENTION

The present invention relates to certain pyridyl amide compounds, methods of making them, pharmaceutical compositions containing them, and methods of using them for the treatment of disease states, disorders, and conditions mediated by the histamine H₃ receptor.

BACKGROUND OF THE INVENTION

The histamine H₃ receptor was first described as a presynaptic autoreceptor in the central nervous system (CNS) (Arrang, J.-M. et al., Nature 1983, 302, 832-837) controlling the synthesis and release of histamine. The histamine H₃ receptor is primarily expressed in the mammalian central nervous system (CNS), with some minimal expression in peripheral tissues such as vascular smooth muscle.

Thus, several indications for histamine H₃ antagonists and inverse agonists have been proposed based on animal pharmacology and other experiments with known histamine H₃ antagonists (e.g. thioperamide). (See: "The Histamine H₃ Receptor—A Target for New Drugs", Leurs, R. and Timmerman, H., (Eds.), Elsevier, 1998; Morisset, S. et al., Nature 2000, 408, 860-864.) These include conditions such as cognitive disorders, sleep disorders, psychiatric disorders, and other disorders.

For example, histamine H₃ antagonists have been shown to have pharmacological activity relevant to several key symptoms of depression, including sleep disorders (e.g. sleep disturbances, fatigue, and lethargy) and cognitive difficulties (e.g. memory and concentration impairment), as described above. For reviews, see: Celanire, S. Drug Discovery Today 2005, 10(23/24), 1613-1627; Hancock, A. A. Biochem. Pharmacol. 2006, 71, 1103-1113.

Substituted diazepanyl benzamides were described as histamine H₃ receptor antagonists in Intl. Patent Appl. Publ. WO05/040144 (May 6, 2005). Substituted pyridines with antiangiogenic properties are disclosed in U.S. Patent Appl. Publ. 2004/0014744 (Jan. 22, 2004). Substituted piperazines and diazepanes are described as histamine H₃ receptor modulators in Intl. Patent Appl. Publ. WO03/004480 (Jan. 16, 2003). However, there remains a need for potent histamine H₃ receptor modulators with desirable pharmaceutical properties.

SUMMARY OF THE INVENTION

Certain pyridyl amide derivatives have now been found to have histamine H₃ receptor modulating activity. Thus, the invention is directed to the general and preferred embodiments defined, respectively, by the independent and dependent claims appended hereto, which are incorporated by reference herein.

In one general aspect the invention relates to a compound of the following Formula (I):

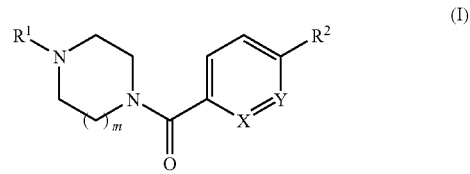

wherein
R¹ is —C₁₋₄alkyl or saturated monocyclic cycloalkyl;
m is 1 or 2;
X is N or CH;
Y is N or CRᵃ;
  Rᵃ is —H, —Z—Ar, —CH₂NRᵇRᶜ, —CN, —CO₂C₁₋₄alkyl, —CO₂H, or —CONRᵇRᶜ;
    where Rᵇ and Rᶜ are each independently —H or —C₁₋₄alkyl; and
R² is —H or —Z—Ar;
with the proviso that one of X and Y is N and one of Rᵃ and R² is —Z—Ar;
  where Z is O or S; and
  Ar is a phenyl or monocyclic heteroaryl group unsubstituted or substituted with one, two, or three R³ substituents;
    where each R³ substituent is independently selected from the group consisting of: halo, —C₁₋₄alkyl, —OH, —OC₁₋₄alkyl, —SC₁₋₄alkyl, —CN, —CONRᵈRᵉ, and —NO₂;
      where Rᵈ and Rᵉ are each independently —H or —C₁₋₄alkyl;
or a pharmaceutically acceptable salt, a pharmaceutically acceptable prodrug, or a pharmaceutically active metabolite thereof.

In certain embodiments, the invention provides compounds of Formula (II):

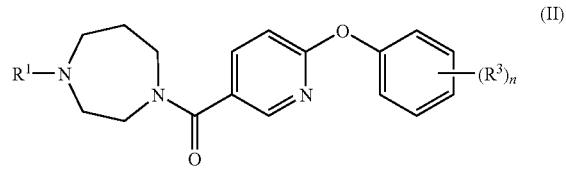

wherein
R¹ is —C₁₋₄alkyl or saturated monocyclic cycloalkyl;
each R³ substituent is independently selected from the group consisting of: halo, —C₁₋₄alkyl, —OH, —OC₁₋₄alkyl, —SC₁₋₄alkyl, —CN, —CONRᵈRᵉ, and —NO₂;
  where Rᵈ and Rᵉ are each independently —H or —C₁₋₄alkyl; and
n is 0, 1, 2, or 3;
or a pharmaceutically acceptable salt, a pharmaceutically acceptable prodrug, or a pharmaceutically active metabolite thereof.

In certain embodiments, the invention provides compounds of Formula (III):

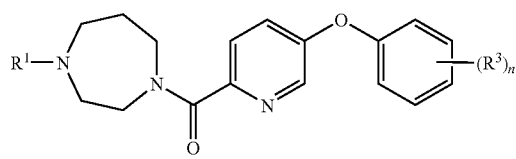

(III)

wherein
R¹ is —$C_{1-4}$alkyl or saturated monocyclic cycloalkyl;
each R³ substituent is independently selected from the group consisting of: halo, —$C_{1-4}$alkyl, —OH, —O$C_{1-4}$alkyl, —S$C_{1-4}$alkyl, —CN, —CONR$^d$R$^e$, and —NO₂;
  where R$^d$ and R$^e$ are each independently —H or —$C_{1-4}$alkyl; and
n is 0, 1, 2, or 3;
or a pharmaceutically acceptable salt, a pharmaceutically acceptable prodrug, or a pharmaceutically active metabolite thereof.

In a further general aspect, the invention relates to pharmaceutical compositions each comprising: (a) an effective amount of a compound of Formula (I), or a pharmaceutically acceptable salt, pharmaceutically acceptable prodrug, or pharmaceutically active metabolite thereof; and (b) a pharmaceutically acceptable excipient.

In another general aspect, the invention is directed to a method of treating a subject suffering from or diagnosed with a disease, disorder, or medical condition mediated by histamine $H_3$ receptor activity, comprising administering to the subject in need of such treatment an effective amount of a compound of Formula (I), or a pharmaceutically acceptable salt, pharmaceutically acceptable prodrug, or pharmaceutically active metabolite thereof.

In certain preferred embodiments of the inventive method, the disease, disorder, or medical condition is selected from: cognitive disorders, sleep disorders, psychiatric disorders, and other disorders.

In another general aspect, the invention is directed to methods of making compounds of Formula (I) or Formula (II) or pharmaceutically acceptable salts thereof.

Additional embodiments, features, and advantages of the invention will be apparent from the following detailed description and through practice of the invention.

DETAILED DESCRIPTION

The invention may be more fully appreciated by reference to the following description, including the following glossary of terms and the concluding examples. For the sake of brevity, the disclosures of the publications, including patents, cited in this specification are herein incorporated by reference.

As used herein, the terms "including", "containing" and "comprising" are used herein in their open, non-limiting sense.

The term "alkyl" refers to a straight- or branched-chain alkyl group having from 1 to 12 carbon atoms in the chain. Examples of alkyl groups include methyl (Me, which also may be structurally depicted by /), ethyl (Et), n-propyl, isopropyl, butyl, isobutyl, sec-butyl, tert-butyl (tBu), pentyl, isopentyl, tert-pentyl, hexyl, isohexyl, and groups that in light of the ordinary skill in the art and the teachings provided herein would be considered equivalent to any one of the foregoing examples.

The term "cycloalkyl" refers to a saturated or partially saturated, monocyclic, fused polycyclic, or spiro polycyclic carbocycle having from 3 to 12 ring atoms per carbocycle. Illustrative examples of cycloalkyl groups include the following entities, in the form of properly bonded moieties:

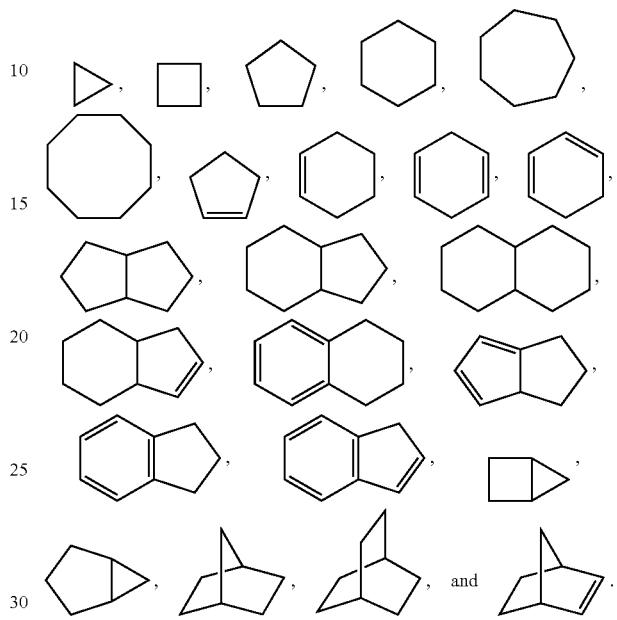

A "heterocycloalkyl" refers to a monocyclic, or fused, bridged, or spiro polycyclic ring structure that is saturated or partially saturated and has from 3 to 12 ring atoms per ring structure selected from carbon atoms and up to three heteroatoms selected from nitrogen, oxygen, and sulfur. The ring structure may optionally contain up to two oxo groups on carbon or sulfur ring members. Illustrative entities, in the form of properly bonded moieties, include:

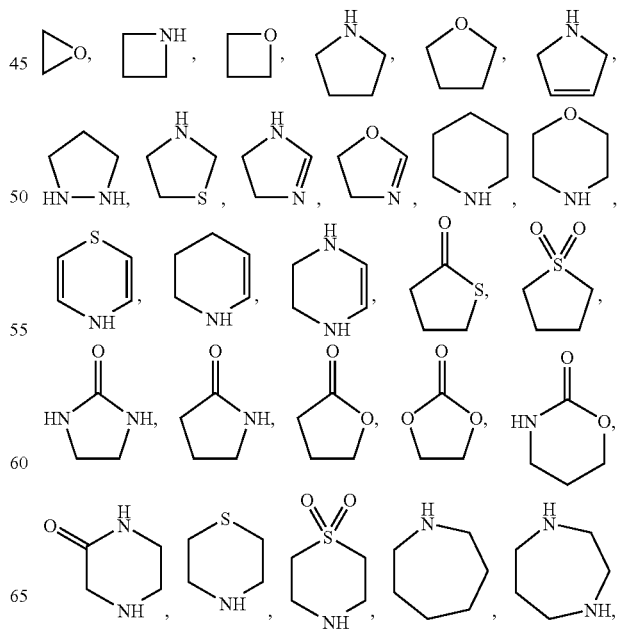

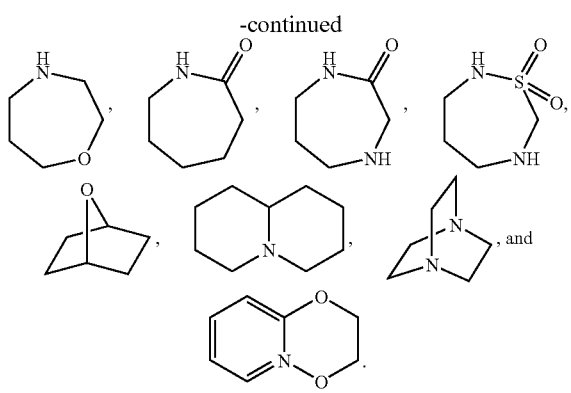

The term "heteroaryl" refers to a monocyclic, fused bicyclic, or fused polycyclic aromatic heterocycle (ring structure having ring atoms selected from carbon atoms and up to four heteroatoms selected from nitrogen, oxygen, and sulfur) having from 3 to 12 ring atoms per heterocycle. Illustrative examples of heteroaryl groups include the following entities, in the form of properly bonded moieties:

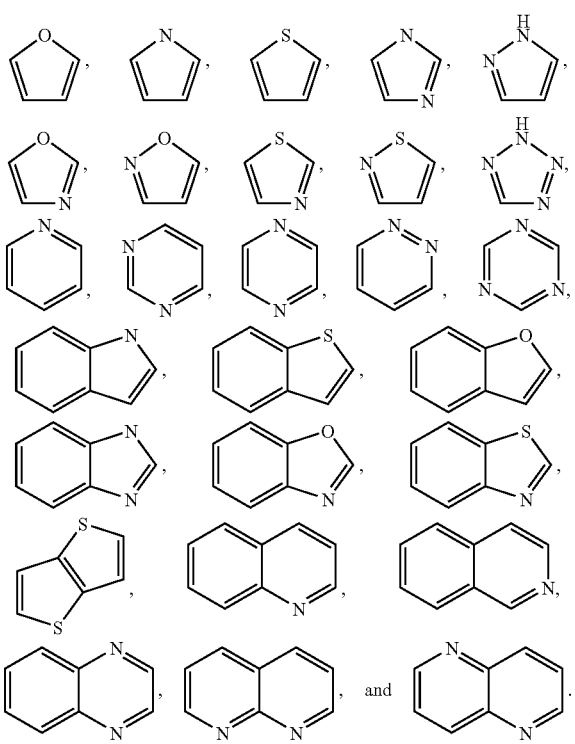

Those skilled in the art will recognize that the species of cycloalkyl, heterocycloalkyl, and heteroaryl groups listed or illustrated above are not exhaustive, and that additional species within the scope of these defined terms may also be selected.

The term "halogen" represents chlorine, fluorine, bromine or iodine. The term "halo" represents chloro, fluoro, bromo or iodo.

The term "substituted" means that the specified group or moiety bears one or more substituents. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system. In cases where a specified moiety or group is not expressly noted as being optionally substituted or substituted with any specified substituent, it is understood that such a moiety or group is intended to be unsubstituted.

Any formula given herein is intended to represent compounds having structures depicted by the structural formula as well as certain variations or forms. In particular, compounds of any formula given herein may have asymmetric centers and therefore exist in different enantiomeric forms. All optical isomers and stereoisomers of the compounds of the general formula, and mixtures thereof, are considered within the scope of the formula. Thus, any formula given herein is intended to represent a racemate, one or more enantiomeric forms, one or more diastereomeric forms, one or more atropisomeric forms, and mixtures thereof. Furthermore, certain structures may exist as geometric isomers (i.e., cis and trans isomers), as tautomers, or as atropisomers. Additionally, any formula given herein is intended to embrace hydrates, solvates, and polymorphs of such compounds, and mixtures thereof.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^{2}H$, $^{3}H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$, $^{125}I$, respectively. Such isotopically labeled compounds are useful in metabolic studies (preferably with $^{14}C$), reaction kinetic studies (with, for example $^{2}H$ or $^{3}H$), detection or imaging techniques [such as positron emission tomography (PET) or single-photon emission computed tomography (SPECT)] including drug or substrate tissue distribution assays, or in radioactive treatment of patients. In particular, an $^{18}F$ or $^{11}C$ labeled compound may be particularly preferred for PET or SPECT studies. Further, substitution with heavier isotopes such as deuterium (i.e., $^{2}H$) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

When referring to any formula given herein, the selection of a particular moiety from a list of possible species for a specified variable is not intended to define the moiety for the variable appearing elsewhere. In other words, where a variable appears more than once, the choice of the species from a specified list is independent of the choice of the species for the same variable elsewhere in the formula.

In preferred embodiments of Formula (I), $R^1$ is methyl, ethyl, propyl, isopropyl, butyl, sec-butyl, or tert-butyl. In other preferred embodiments, $R^1$ is methyl or isopropyl. In still other preferred embodiments, $R^1$ is cyclopropyl, cyclobutyl, cyclopentyl, or cyclohexyl.

In preferred embodiments, m is 1. In other preferred embodiments, m is 2.

In preferred embodiments, X is N, Y is $CR^a$, and $R^2$ is —Z—Ar. In other preferred embodiments, X is CH, Y is N, and $R^2$ is —Z—Ar. In still other preferred embodiments, X is N, Y is $CR^a$, and $R^2$ is —H, where $R^1$ is —Z—Ar.

In preferred embodiments, $R^a$ is —CN, —CONH$_2$, or —CH$_2$NH$_2$. In other preferred embodiments, $R^a$ is —H.

In preferred embodiments, Z is O. In other preferred embodiments, Z is S.

In preferred embodiments, Ar is a phenyl, pyrrolyl, furanyl, thiophenyl, imidazolyl, pyrazolyl, oxazolyl, isoxazolyl, thiazolyl, pyridyl, pyrimidinyl, or pyrazinyl group, each unsubstituted or substituted with one, two, or three $R^3$ substituents. In other preferred embodiments, Ar is a phenyl group unsubstituted or substituted with one, two, or three $R^3$ substituents. In still other preferred embodiments, Ar is a 4-halophenyl group. In further preferred embodiments, Ar is phenyl, 3,4-dichlorophenyl, 4-methylsulfanylphenyl, 3-chlorophenyl, 3-fluorophenyl, 4-chloro-3-methylphenyl, 3-cyanophenyl, 4-chlorophenyl, 4-fluorophenyl, 3,4-difluorophenyl, 2-fluorophenyl, 3-chlorophenyl, 2,4-difluorophenyl, 3,5-dichlorophenyl, 2,5-difluorophenyl, 3,5-difluorophenyl, 3-methyl-4-methylsulfanylphenyl, or 3-pyridyl.

In preferred embodiments of Formula (II) and Formula (III), $R^1$ is cyclopropyl, cyclobutyl, cyclopentyl, or cyclohexyl.

In certain preferred embodiments, the compound of Formula (I) is selected from the group consisting of:

| Ex. | Chemical Name |
|---|---|
| 1 | [6-(3,4-Dichloro-phenoxy)-pyridin-3-yl]-(4-isopropyl-piperazin-1-yl)-methanone; |
| 2 | (4-Isopropyl-piperazin-1-yl)-[6-(pyridin-3-yloxy)-pyridin-3-yl]-methanone; |
| 3 | (4-Isopropyl-piperazin-1-yl)-[6-(4-methylsulfanyl-phenoxy)-pyridin-3-yl]-methanone; |
| 4 | [6-(3-Chloro-phenoxy)-pyridin-3-yl]-(4-isopropyl-piperazin-1-yl)-methanone; |
| 5 | (4-Isopropyl-piperazin-1-yl)-(6-phenoxy-pyridin-3-yl)-methanone; |
| 6 | [6-(4-Chloro-3-methyl-phenoxy)-pyridin-3-yl]-(4-isopropyl-piperazin-1-yl)-methanone; |
| 7 | 3-[5-(4-Isopropyl-piperazine-1-carbonyl)-pyridin-2-yloxy]-benzonitrile; |
| 8 | [6-(4-Chloro-phenoxy)-pyridin-3-yl]-(4-isopropyl-piperazin-1-yl)-methanone; |
| 9 | (4-Cyclopropyl-[1,4]diazepan-1-yl)-[6-(3,4-dichloro-phenoxy)-pyridin-3-yl]-methanone; |
| 10 | [6-(4-Chloro-phenoxy)-pyridin-3-yl]-(4-cyclopropyl-[1,4]diazepan-1-yl)-methanone; |
| 11 | 3-[5-(4-Cyclopropyl-[1,4]diazepane-1-carbonyl)-pyridin-2-yloxy]-benzonitrile; |
| 12 | [6-(4-Chloro-3-methyl-phenoxy)-pyridin-3-yl]-(4-cyclopropyl-[1,4]diazepan-1-yl)-methanone; |
| 13 | (4-Cyclopropyl-[1,4]diazepan-1-yl)-(6-phenoxy-pyridin-3-yl)-methanone; |
| 14 | (4-Cyclobutyl-[1,4]diazepan-1-yl)-[6-(3,4-dichloro-phenoxy)-pyridin-3-yl]-methanone; |
| 15 | [6-(3,4-Dichloro-phenoxy)-pyridin-3-yl]-(4-isopropyl-[1,4]diazepan-1-yl)-methanone; |
| 16 | [6-(4-Chloro-3-methyl-phenoxy)-pyridin-3-yl]-(4-cyclobutyl-[1,4]diazepan-1-yl)-methanone; |
| 17 | [6-(4-Chloro-3-methyl-phenoxy)-pyridin-3-yl]-(4-isopropyl-[1,4]diazepan-1-yl)-methanone; |
| 18 | (4-Cyclopropyl-[1,4]diazepan-1-yl)-[6-(4-fluoro-phenoxy)-pyridin-3-yl]-methanone; |
| 19 | (4-Cyclobutyl-[1,4]diazepan-1-yl)-[6-(4-fluoro-phenoxy)-pyridin-3-yl]-methanone; |
| 20 | 3-[5-(4-Cyclobutyl-[1,4]diazepane-1-carbonyl)-pyridin-2-yloxy]-benzonitrile; |
| 21 | (4-Cyclobutyl-[1,4]diazepan-1-yl)-(6-phenoxy-pyridin-3-yl)-methanone; |
| 22 | (4-Cyclopropyl-piperazin-1-yl)-[6-(4-fluoro-phenoxy)-pyridin-3-yl]-methanone; |
| 23 | [6-(3-Chloro-phenoxy)-pyridin-3-yl]-(4-cyclopropyl-[1,4]diazepan-1-yl)-methanone; |
| 24 | [6-(3-Chloro-phenoxy)-pyridin-3-yl]-(4-cyclobutyl-[1,4]diazepan-1-yl)-methanone; |
| 25 | [6-(4-Chloro-phenoxy)-pyridin-3-yl]-(4-cyclobutyl-[1,4]diazepan-1-yl)-methanone; |
| 26 | (4-Cyclobutyl-[1,4]diazepan-1-yl)-[6-(3,4-difluoro-phenoxy)-pyridin-3-yl]-methanone; |
| 27 | (4-Cyclopropyl-[1,4]diazepan-1-yl)-[6-(3,4-difluoro-phenoxy)-pyridin-3-yl]-methanone; |
| 28 | [6-(3,4-Difluoro-phenoxy)-pyridin-3-yl]-(4-isopropyl-piperazin-1-yl)-methanone; |
| 29 | (4-Cyclobutyl-[1,4]diazepan-1-yl)-[6-(2-fluoro-phenoxy)-pyridin-3-yl]-methanone; |
| 30 | (4-Cyclobutyl-[1,4]diazepan-1-yl)-[6-(2,4-difluoro-phenoxy)-pyridin-3-yl]-methanone; |
| 31 | (4-Cyclopropyl-[1,4]diazepan-1-yl)-[6-(2-fluoro-phenoxy)-pyridin-3-yl]-methanone; |
| 32 | (4-Cyclopropyl-[1,4]diazepan-1-yl)-[6-(2,4-difluoro-phenoxy)-pyridin-3-yl]-methanone; |
| 33 | (4-Cyclobutyl-[1,4]diazepan-1-yl)-[6-(3,5-dichloro-phenoxy)-pyridin-3-yl]-methanone; |

-continued

| Ex. | Chemical Name |
|---|---|
| 34 | (4-Cyclopropyl-[1,4]diazepan-1-yl)-[6-(2,5-difluoro-phenoxy)-pyridin-3-yl]-methanone; |
| 35 | (4-Cyclopropyl-[1,4]diazepan-1-yl)-[6-(3,5-dichloro-phenoxy)-pyridin-3-yl]-methanone; |
| 36 | (4-Cyclobutyl-[1,4]diazepan-1-yl)-[6-(3,5-difluoro-phenoxy)-pyridin-3-yl]-methanone; |
| 37 | (4-Cyclopropyl-[1,4]diazepan-1-yl)-[6-(3-fluoro-phenoxy)-pyridin-3-yl]-methanone; |
| 38 | [6-(3-Fluoro-phenoxy)-pyridin-3-yl]-(4-isopropyl-[1,4]diazepan-1-yl)-methanone; |
| 39 | (4-Cyclobutyl-[1,4]diazepan-1-yl)-[6-(3-fluoro-phenoxy)-pyridin-3-yl]-methanone; |
| 40 | (4-Cyclobutyl-[1,4]diazepan-1-yl)-[6-(3-methyl-4-methylsulfanyl-phenoxy)-pyridin-3-yl]-methanone; |
| 41 | (4-Cyclopropyl-[1,4]diazepan-1-yl)-[6-(3-methyl-4-methylsulfanyl-phenoxy)-pyridin-3-yl]-methanone; |
| 42 | (4-Isopropyl-[1,4]diazepan-1-yl)-[6-(3-methyl-4-methylsulfanyl-phenoxy)-pyridin-3-yl]-methanone; |
| 43 | [6-(3,4-Dichloro-phenoxy)-pyridin-2-yl]-(4-isopropyl-piperazin-1-yl)-methanone; |
| 44 | (4-Cyclopropyl-[1,4]diazepan-1-yl)-[6-(3,4-dichloro-phenoxy)-pyridin-2-yl]-methanone; |
| 45 | (4-Cyclobutyl-[1,4]diazepan-1-yl)-[6-(3,4-dichloro-phenoxy)-pyridin-2-yl]-methanone; |
| 46 | [6-(3,4-Dichloro-phenoxy)-pyridin-2-yl]-(4-isopropyl-[1,4]diazepan-1-yl)-methanone; |
| 47 | [6-(4-Chloro-3-methyl-phenoxy)-pyridin-2-yl]-(4-cyclopropyl-[1,4]diazepan-1-yl)-methanone; |
| 48 | [6-(4-Chloro-3-methyl-phenoxy)-pyridin-2-yl]-(4-cyclobutyl-[1,4]diazepan-1-yl)-methanone; |
| 49 | [6-(4-Chloro-3-methyl-phenoxy)-pyridin-2-yl]-(4-isopropyl-[1,4]diazepan-1-yl)-methanone; |
| 50 | [5-(3,4-Dichloro-phenoxy)-pyridin-2-yl]-(4-isopropyl-[1,4]diazepan-1-yl)-methanone; |
| 51 | (4-Cyclobutyl-[1,4]diazepan-1-yl)-[5-(3,4-dichloro-phenoxy)-pyridin-2-yl]-methanone; |
| 52 | (4-Cyclopropyl-[1,4]diazepan-1-yl)-[5-(3,4-dichloro-phenoxy)-pyridin-2-yl]-methanone; |
| 53 | 3-(3,4-Dichloro-phenoxy)-6-(4-isopropyl-piperazine-1-carbonyl)-pyridine-2-carbonitrile; |
| 54 | 3-(3,4-Dichloro-phenoxy)-6-(4-isopropyl-piperazine-1-carbonyl)-pyridine-2-carboxylic acid amide; |
| 55 | 6-(4-Cyclopropyl-[1,4]diazepane-1-carbonyl)-3-(4-methylsulfanyl-phenoxy)-pyridine-2-carbonitrile; |
| 56 | 6-(4-Cyclopropyl-[1,4]diazepane-1-carbonyl)-3-(pyridin-3-yloxy)-pyridine-2-carbonitrile; |
| 57 | 3-(4-Chloro-3-methyl-phenoxy)-6-(4-cyclopropyl-[1,4]diazepane-1-carbonyl)-pyridine-2-carbonitrile; |
| 58 | 6-(4-Cyclopropyl-[1,4]diazepane-1-carbonyl)-3-(3,4-dichloro-phenoxy)-pyridine-2-carbonitrile; |
| 59 | 6-(4-Cyclopropyl-[1,4]diazepane-1-carbonyl)-3-(4-fluoro-phenoxy)-pyridine-2-carbonitrile; |
| 60 | 6-(4-Cyclopropyl-[1,4]diazepane-1-carbonyl)-3-(3-fluoro-phenoxy)-pyridine-2-carbonitrile; |
| 61 | 6-(4-Cyclopropyl-[1,4]diazepane-1-carbonyl)-3-(2-fluoro-phenoxy)-pyridine-2-carbonitrile; |
| 62 | 6-(4-Cyclopropyl-[1,4]diazepane-1-carbonyl)-3-(4-methylsulfanyl-phenoxy)-pyridine-2-carboxylic acid amide; |
| 63 | 6-(4-Cyclopropyl-[1,4]diazepane-1-carbonyl)-3-(pyridin-3-yloxy)-pyridine-2-carboxylic acid amide; |
| 64 | [6-Aminomethyl-5-(3,4-dichloro-phenoxy)-pyridin-2-yl]-(4-isopropyl-piperazin-1-yl)-methanone; |
| 65 | (4-Cyclopentyl-[1,4]diazepan-1-yl)-(6-phenoxy-pyridin-3-yl)-methanone; |
| 66 | (4-Cyclopentyl-[1,4]diazepan-1-yl)-[6-(3,4-dichloro-phenoxy)-pyridin-3-yl]-methanone; |
| 67 | (4-Cyclopentyl-[1,4]diazepan-1-yl)-[6-(4-fluoro-phenoxy)-pyridin-3-yl]-methanone; |
| 68 | [5-(4-Chloro-phenoxy)-pyridin-2-yl]-(4-cyclobutyl-[1,4]diazepan-1-yl)-methanone; |
| 69 | (4-Cyclobutyl-[1,4]diazepan-1-yl)-[5-(4-fluoro-phenoxy)-pyridin-2-yl]-methanone; |
| 70 | [5-(3-Chloro-phenoxy)-pyridin-2-yl]-(4-cyclobutyl-[1,4]diazepan-1-yl)-methanone; |
| 71 | (4-Cyclobutyl-[1,4]diazepan-1-yl)-[5-(3-fluoro-phenoxy)-pyridin-2-yl]-methanone; |
| 72 | (4-Cyclobutyl-[1,4]diazepan-1-yl)-[5-(2-fluoro-phenoxy)-pyridin-2-yl]-methanone; |

-continued

| Ex. | Chemical Name |
|---|---|
| 73 | [6-(2-Chloro-phenoxy)-pyridin-3-yl]-(4-cyclobutyl-[1,4]diazepan-1-yl)-methanone; |
| 74 | (4-Cyclopentyl-piperazin-1-yl)-[6-(4-fluoro-phenoxy)-pyridin-3-yl]-methanone; |
| 75 | [6-(2-Chloro-phenoxy)-pyridin-3-yl]-(4-isopropyl-piperazin-1-yl)-methanone; |
| 76 | [6-(2-Chloro-phenoxy)-pyridin-3-yl]-(4-cyclopentyl-piperazin-1-yl)-methanone; |
| 77 | [6-(4-Chloro-phenoxy)-pyridin-3-yl]-(4-cyclopentyl-piperazin-1-yl)-methanone; |
| 78 | (4-Cyclopentyl-piperazin-1-yl)-[6-(2-fluoro-phenoxy)-pyridin-3-yl]-methanone; |
| 79 | (4-Cyclobutyl-piperazin-1-yl)-[6-(4-fluoro-phenoxy)-pyridin-3-yl]-methanone; |
| 80 | [6-(4-Fluoro-phenoxy)-pyridin-3-yl]-(4-methyl-[1,4]diazepan-1-yl)-methanone; |
| 81 | 6-(4-Cyclopropyl-[1,4]diazepane-1-carbonyl)-3-phenoxy-pyridine-2-carbonitrile; |
| 82 | 6-(4-Cyclobutyl-[1,4]diazepane-1-carbonyl)-3-(4-fluoro-phenoxy)-pyridine-2-carbonitrile; |
| 83 | (4-Cyclobutyl-[1,4]diazepan-1-yl)-[6-(4-fluoro-phenylsulfanyl)-pyridin-3-yl]-methanone; |
| 84 | (4-Cyclobutyl-[1,4]diazepan-1-yl)-[5-(4-fluoro-phenylsulfanyl)-pyridin-2-yl]-methanone; |
| 85 | [6-(4-Chloro-phenylsulfanyl)-pyridin-3-yl]-(4-cyclobutyl-[1,4]diazepan-1-yl)-methanone; |
| 86 | (4-Cyclobutyl-[1,4]diazepan-1-yl)-(6-phenylsulfanyl-pyridin-3-yl)-methanone; |
| 87 | (4-Cyclopentyl-piperazin-1-yl)-[6-(3-methyl-4-methylsulfanyl-phenoxy)-pyridin-3-yl]-methanone; |
| 88 | (4-Isopropyl-piperazin-1-yl)-[6-(3-methyl-4-methylsulfanyl-phenoxy)-pyridin-3-yl]-methanone; |
| 89 | [6-(4-Fluoro-phenoxy)-pyridin-3-yl]-(4-isopropyl-piperazin-1-yl)-methanone; |
| 90 | (4-Ethyl-[1,4]diazepan-1-yl)-[6-(4-fluoro-phenoxy)-pyridin-3-yl]-methanone; |
| 91 | (4-Cyclobutyl-[1,4]diazepan-1-yl)-(5-phenylsulfanyl-pyridin-2-yl)-methanone; |
| 92 | [6-(4-Fluoro-phenoxy)-pyridin-3-yl]-(4-methyl-[1,4]diazepan-1-yl)-methanone; |
| 93 | [6-(4-Fluoro-phenoxy)-pyridin-3-yl]-(4-isobutyl-piperazin-1-yl)-methanone; |
| 94 | (4-Cyclobutyl-[1,4]diazepan-1-yl)-(5-phenylsulfanyl-pyridin-2-yl)-methanone; |
| 95 | (4-Cyclobutyl-[1,4]diazepan-1-yl)-(6-phenylsulfanyl-pyridin-3-yl)-methanone; |
| 96 | [6-(4-Chloro-phenylsulfanyl)-pyridin-3-yl]-(4-cyclobutyl-[1,4]diazepan-1-yl)-methanone; |
| 97 | (4-Cyclobutyl-[1,4]diazepan-1-yl)-[6-(4-fluoro-phenylsulfanyl)-pyridin-3-yl]-methanone; |
| 98 | (4-Ethyl-[1,4]diazepan-1-yl)-[6-(4-fluoro-phenoxy)-pyridin-3-yl]-methanone; |
| 99 | [6-(4-Fluoro-phenoxy)-pyridin-3-yl]-(4-isopropyl-piperazin-1-yl)-methanone; |
| 100 | (4-Cyclopentyl-piperazin-1-yl)-[6-(3-methyl-4-methylsulfanyl-phenoxy)-pyridin-3-yl]-methanone; |
| 101 | (4-Isopropyl-piperazin-1-yl)-[6-(3-methyl-4-methylsulfanyl-phenoxy)-pyridin-3-yl]-methanone; |
| 102 | (4-Cyclobutyl-[1,4]diazepan-1-yl)-(6-o-tolyloxy-pyridin-3-yl)-methanone; |
| 103 | (4-Cyclobutyl-[1,4]diazepan-1-yl)-(6-m-tolyloxy-pyridin-3-yl)-methanone; |
| 104 | (4-Cyclobutyl-[1,4]diazepan-1-yl)-(6-p-tolyloxy-pyridin-3-yl)-methanone; and |
| 105 | (4-Cyclobutyl-[1,4]diazepan-1-yl)-[6-(4-methylsulfanyl-phenoxy)-pyridin-3-yl]-methanone; | and pharmaceutically acceptable salts thereof.

The invention includes also pharmaceutically acceptable salts of the compounds of Formula (I), preferably of those described above and of the specific compounds exemplified herein, and methods of treatment using such salts. In a preferred embodiment, the invention refers to hydrochloride monohydrates of compounds of Formula (I).

A "pharmaceutically acceptable salt" is intended to mean a salt of a free acid or base of a compound represented by Formula (I) that is non-toxic, biologically tolerable, or otherwise biologically suitable for administration to the subject. See, generally, S. M. Berge, et al., "Pharmaceutical Salts", J. Pharm. Sci., 1977, 66:1-19, and *Handbook of Pharmaceutical Salts, Properties, Selection, and Use*, Stahl and Wermuth, Eds., Wiley-VCH and VHCA, Zurich, 2002. Examples of pharmaceutically acceptable salts are those that are pharmacologically effective and suitable for contact with the tissues of patients without undue toxicity, irritation, or allergic response. A compound of Formula (I) may possess a sufficiently acidic group, a sufficiently basic group, or both types of functional groups, and accordingly react with a number of inorganic or organic bases, and inorganic and organic acids, to form a pharmaceutically acceptable salt. Examples of pharmaceutically acceptable salts include sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methyl benzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates.

If the compound of Formula (I) contains a basic nitrogen, the desired pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, ethanesulfonic acid, any compatible mixture of acids such as those given as examples herein, and any other acid and mixture thereof that are regarded as equivalents or acceptable substitutes in light of the ordinary level of skill in this technology.

If the compound of Formula (I) is an acid, such as a carboxylic acid or sulfonic acid, the desired pharmaceutically acceptable salt may be prepared by any suitable method, for example, treatment of the free acid with an inorganic or organic base, such as an amine (primary, secondary or tertiary), an alkali metal hydroxide, alkaline earth metal hydroxide, any compatible mixture of bases such as those given as examples herein, and any other base and mixture thereof that are regarded as equivalents or acceptable substitutes in light of the ordinary level of skill in this technology. Illustrative examples of suitable salts include organic salts derived from amino acids, such as glycine and arginine, ammonia, carbonates, bicarbonates, primary, secondary, and tertiary amines, and cyclic amines, such as benzylamines, pyrrolidines, piperidine, morpholine, and piperazine, and inorganic salts derived from sodium, calcium, potassium, magnesium, manganese, iron, copper, zinc, aluminum, and lithium.

The invention also relates to pharmaceutically acceptable prodrugs of the compounds of Formula (I), and treatment methods employing such pharmaceutically acceptable prodrugs. The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound of Formula (I)). A "pharmaceutically acceptable prodrug" is a prodrug that is non-toxic, biologically tolerable, and otherwise biologically suitable for administration to the subject. Illustrative procedures for the selection and preparation of suitable prodrug derivatives are described, for example, in "Design of Prodrugs", ed. H. Bundgaard, Elsevier, 1985.

Examples of prodrugs include compounds having an amino acid residue, or a polypeptide chain of two or more (e.g., two, three or four) amino acid residues, covalently joined through an amide or ester bond to a free amino, hydroxy, or carboxylic acid group of a compound of Formula (I). Examples of amino acid residues include the twenty naturally occurring amino acids, commonly designated by three letter symbols, as well as 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone.

Additional types of prodrugs may be produced, for instance, by derivatizing free carboxyl groups of structures of Formula (I) as amides or alkyl esters. Examples of amides include those derived from ammonia, primary $C_{1-6}$alkyl amines and secondary di($C_{1-6}$alkyl) amines. Secondary amines include 5- or 6-membered heterocycloalkyl or heteroaryl ring moieties. Examples of amides include those that are derived from ammonia, $C_{1-3}$alkyl primary amines, and di($C_{1-2}$alkyl)amines. Examples of esters of the invention include $C_{1-7}$alkyl, $C_{5-7}$cycloalkyl, phenyl, and phenyl ($C_{1-6}$alkyl) esters. Preferred esters include methyl esters. Prodrugs may also be prepared by derivatizing free hydroxy groups using groups including hemisuccinates, phosphate esters, dimethylaminoacetates, and phosphoryloxymethyloxycarbonyls, following procedures such as those outlined in *Adv. Drug Delivery Rev.* 1996, 19, 115. Carbamate derivatives of hydroxy and amino groups may also yield prodrugs. Carbonate derivatives, sulfonate esters, and sulfate esters of hydroxy groups may also provide prodrugs. Derivatization of hydroxy groups as (acyloxy)methyl and (acyloxy)ethyl ethers, wherein the acyl group may be an alkyl ester, optionally substituted with one or more ether, amine, or carboxylic acid functionalities, or where the acyl group is an amino acid ester as described above, is also useful to yield prodrugs. Prodrugs of this type may be prepared as described in *J. Med. Chem.* 1996, 39, 10. Free amines can also be derivatized as amides, sulfonamides or phosphonamides. All of these prodrug moieties may incorporate groups including ether, amine, and carboxylic acid functionalities.

The present invention also relates to pharmaceutically active metabolites of the compounds of Formula (I), which may also be used in the methods of the invention. A "pharmaceutically active metabolite" means a pharmacologically active product of metabolism in the body of a compound of Formula (I) or salt thereof. Prodrugs and active metabolites of a compound may be determined using routine techniques known or available in the art. See, e.g., Bertolini, et al., *J. Med. Chem.* 1997, 40, 2011-2016; Shan, et al., *J. Pharm. Sci.* 1997, 86 (7), 765-767; Bagshawe, *Drug Dev. Res.* 1995, 34, 220-230; Bodor, *Adv. Drug Res.* 1984, 13, 224-331; Bundgaard, Design of Prodrugs (Elsevier Press, 1985); and Larsen, Design and Application of Prodrugs, Drug Design and Development (Krogsgaard-Larsen, et al., eds., Harwood Academic Publishers, 1991).

The compounds of Formula (I) and their pharmaceutically acceptable salts, pharmaceutically acceptable prodrugs, and pharmaceutically active metabolites of the present invention are useful as modulators of the histamine $H_3$ receptor in the methods of the invention. As such modulators, the compounds may act as antagonists, agonists, or inverse agonists. The compounds of the invention may be used in the methods for the treatment or prevention of medical conditions, diseases, or disorders mediated through modulation of the histamine $H_3$ receptor, such as those described herein.

The term "treat" or "treating" as used herein is intended to refer to administration of a compound or composition of the invention to a subject for the purpose of effecting a therapeutic or prophylactic benefit through modulation of histamine $H_3$ receptor activity. Treating includes reversing, ameliorating, alleviating, inhibiting the progress of, lessening the severity of, or preventing a disease, disorder, or condition, or one or more symptoms of such disease, disorder or condition mediated through modulation of histamine $H_3$ receptor activity. The term "subject" refers to a mammalian patient in need of such treatment, such as a human. "Modulators" include both inhibitors and activators, where "inhibitors" refer to compounds that decrease, prevent, inactivate, desensitize or down-regulate histamine $H_3$ receptor expression or activity, and "activators" are compounds that increase, activate, facilitate, sensitize, or up-regulate histamine $H_3$ receptor expression or activity.

Accordingly, the invention relates to methods of using the compounds described herein to treat subjects diagnosed with or suffering from a disease, disorder, or condition mediated by histamine $H_3$ receptor activity, such as: cognitive disorders, sleep disorders, psychiatric disorders, and other disorders. Symptoms or disease states are intended to be included within the scope of "medical conditions, disorders, or diseases."

Cognitive disorders include, for example, dementia, Alzheimer's disease (Panula, P. et al., Soc. Neurosci. Abstr. 1995, 21, 1977), cognitive dysfunction, mild cognitive impairment (pre-dementia), attention deficit hyperactivity disorders (ADHD), attention-deficit disorders, and learning and memory disorders (Barnes, J. C. et al., Soc. Neurosci. Abstr. 1993, 19, 1813). Learning and memory disorders include, for example, learning impairment, memory impairment, age-related cognitive decline, and memory loss. $H_3$ antagonists have been shown to improve memory in a variety of memory tests, including the elevated plus maze in mice (Miyazaki, S. et al. Life Sci. 1995, 57(23), 2137-2144), a two-trial place recognition task (Orsetti, M. et al. Behav. Brain Res. 2001, 124(2), 235-242), the passive avoidance test in mice (Miyazaki, S. et al. Meth. Find. Exp. Clin. Pharmacol. 1995, 17(10), 653-658) and the radial maze in rats (Chen, Z. Acta Pharmacol. Sin. 2000, 21(10), 905-910). Also, in the spontaneously hypertensive rat, an animal model for the learning impairments in attention-deficit disorders, $H_3$ antagonists were shown to improve memory (Fox, G. B. et al. Behav. Brain Res. 2002, 131(1-2), 151-161).

Sleep disorders include, for example, insomnia, disturbed sleep, narcolepsy (with or without associated cataplexy), cataplexy, disorders of sleep/wake homeostasis, idiopathic somnolence, excessive daytime sleepiness (EDS), circadian rhythm disorders, fatigue, lethargy, jet lag, and REM-behavioral disorder. Fatigue and/or sleep impairment may be caused by or associated with various sources, such as, for example, sleep apnea, perimenopausal hormonal shifts, Parkinson's disease, multiple sclerosis (MS), depression, chemotherapy, or shift work schedules.

Psychiatric disorders include, for example, schizophrenia (Schlicker, E. and Marr, I., Naunyn-Schmiedeberg's Arch. Pharmacol. 1996, 353, 290-294), bipolar disorders, manic disorders, depression (Lamberti, C. et al. Br. J. Pharmacol. 1998, 123(7), 1331-1336; Perez-Garcia, C. et al. Psychopharmacology 1999, 142(2), 215-220) (Also see: Stark, H. et al., Drugs Future 1996, 21(5), 507-520; and Leurs, R. et al., Prog. Drug Res. 1995, 45, 107-165 and references cited therein.), obsessive-compulsive disorder, and post-traumatic stress disorder.

Other disorders include, for example, motion sickness, vertigo (e.g. vertigo or benign postural vertigo), tinitus, epilepsy (Yokoyama, H. et al., Eur. J. Pharmacol. 1993, 234, 129-133), migraine, neurogenic inflammation, eating disorders (Machidori, H. et al., Brain Res. 1992, 590, 180-186), obesity, substance abuse disorders, movement disorders (e.g. restless leg syndrome), and eye-related disorders (e.g. macular degeneration and retinitis pigmentosis).

Particularly, as modulators of the histamine $H_3$ receptor, the compounds of the present invention are useful in the treatment or prevention of depression, disturbed sleep, narcolepsy, fatigue, lethargy, cognitive impairment, memory impairment, memory loss, learning impairment, attention-deficit disorders, and eating disorders.

In treatment methods according to the invention, an effective amount of at least one compound according to the invention is administered to a subject suffering from or diagnosed as having such a disease, disorder, or condition. An "effective amount" means an amount or dose sufficient to generally bring about the desired therapeutic or prophylactic benefit in patients in need of such treatment for the designated disease, disorder, or condition.

Effective amounts or doses of the compounds of the present invention may be ascertained by routine methods such as modeling, dose escalation studies or clinical trials, and by taking into consideration routine factors, e.g., the mode or route of administration or drug delivery, the pharmacokinetics of the compound, the severity and course of the disease, disorder, or condition, the subject's previous or ongoing therapy, the subject's health status and response to drugs, and the judgment of the treating physician. An example of a dose is in the range of from about 0.001 to about 200 mg of compound per kg of subject's body weight per day, preferably about 0.05 to 100 mg/kg/day, or about 1 to 35 mg/kg/day, in single or divided dosage units (e.g., BID, TID, QID). For a 70-kg human, an illustrative range for a suitable dosage amount is from about 0.05 to about 7 g/day, or about 0.2 to about 2.5 g/day.

Once improvement of the patient's disease, disorder, or condition has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms.

In addition, the compounds of the invention may be used in combination with additional active ingredients in the treatment of the above conditions. In an exemplary embodiment, additional active ingredients are those that are known or discovered to be effective in the treatment of conditions, disorders, or diseases mediated by histamine $H_3$ receptor activity or that are active against another target associated with the particular condition, disorder, or disease, such as $H_1$ receptor antagonists, $H_2$ receptor antagonists, $H_3$ receptor antagonists, topiramate (Topamax™), and neurotransmitter modulators such as serotonin-norepinephrine reuptake inhibitors, selective serotonin reuptake inhibitors (SSRIs), noradrenergic reuptake inhibitors, non-selective serotonin re-uptake inhibitors (NSSRIs), acetylcholinesterase inhibitors (such as tetrahydroaminoacridine, Donepezil (Aricept™), Rivastigmine, or Galantamine (Reminyl™)), or modafinil. The combination may serve to increase efficacy (e.g., by including in the combination a compound potentiating the potency or effectiveness of a compound according to the invention), decrease one or more side effects, or decrease the required dose of the compound according to the invention.

More particularly, compounds of the invention in combination with modafinil are useful for the treatment of narcolepsy, excessive daytime sleepiness (EDS), Alzheimer's disease, depression, attention-deficit disorders, MS-related fatigue, post-anesthesia grogginess, cognitive impairment, schizophrenia, spasticity associated with cerebral palsy, age-related memory decline, idiopathic somnolence, or jet-lag. Preferably, the combination method employs doses of modafinil in the range of about 20 to 300 mg per dose.

In another embodiment, compounds of the invention in combination with topiramate are useful for the treatment of obesity. Preferably, the combination method employs doses of topiramate in the range of about 20 to 400 mg per dose.

The compounds of the invention are used, alone or in combination with one or more other active ingredients, to formulate pharmaceutical compositions of the invention. A pharmaceutical composition of the invention comprises: (a) an effective amount of a compound of Formula (I), or a pharmaceutically acceptable salt, pharmaceutically acceptable prodrug, or pharmaceutically active metabolite thereof; and (b) a pharmaceutically acceptable excipient.

A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of a compound of the invention and that is compatible therewith. Examples of excipients include calcium carbonate, calcium phosphate, various sugars and types of starch, cellulose derivatives, gelatin, vegetable oils, and polyethylene glycols.

Delivery forms of the pharmaceutical compositions containing one or more dosage units of the compounds of the invention may be prepared using suitable pharmaceutical excipients and compounding techniques now or later known or available to those skilled in the art. The compositions may be administered in the inventive methods by oral, parenteral, rectal, topical, or ocular routes, or by inhalation.

The preparation may be in the form of tablets, capsules, sachets, dragees, powders, granules, lozenges, powders for reconstitution, liquid preparations, or suppositories. Preferably, the compositions are formulated for intravenous infusion, topical administration, or oral administration.

For oral administration, the compounds of the invention can be provided in the form of tablets or capsules, or as a solution, emulsion, or suspension. To prepare the oral compositions, the compounds may be formulated to yield a dosage of, e.g., from about 0.05 to about 100 mg/kg daily, or from about 0.05 to about 35 mg/kg daily, or from about 0.1 to about 10 mg/kg daily.

Oral tablets may include a compound according to the invention mixed with pharmaceutically acceptable excipients such as inert diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are suitable disintegrating agents. Binding agents may include starch and gelatin. The lubricating agent, if present, may be magnesium stearate, stearic acid or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, compounds of the invention may be mixed with a solid, semi-solid, or liquid diluent. Soft gelatin capsules may be prepared by mixing the compound of the invention with water, an oil such as peanut oil, sesame oil, or olive oil, liquid paraffin, a mixture of mono and di-glycerides of short chain fatty acids, polyethylene glycol 400, or propylene glycol.

Liquids for oral administration may be in the form of suspensions, solutions, emulsions or syrups or may be presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The compounds of this invention may also be administered by non-oral routes. For example, the compositions may be formulated for rectal administration as a suppository. For parenteral use, including intravenous, intramuscular, intraperitoneal, or subcutaneous routes, the compounds of the invention may be provided in sterile aqueous solutions or suspensions, buffered to an appropriate pH and isotonicity or in parenterally acceptable oil. Suitable aqueous vehicles include Ringer's solution and isotonic sodium chloride. Such forms will be presented in unit-dose form such as ampules or disposable injection devices, in multi-dose forms such as vials from which the appropriate dose may be withdrawn, or in a solid form or pre-concentrate that can be used to prepare an injectable formulation. Illustrative infusion doses may range from about 1 to 1000 µg/kg/minute of compound, admixed with a pharmaceutical carrier over a period ranging from several minutes to several days.

For topical administration, the compounds may be mixed with a pharmaceutical carrier at a concentration of about 0.1% to about 10% of drug to vehicle. Another mode of administering the compounds of the invention may utilize a patch formulation to affect transdermal delivery.

Compounds of the invention may alternatively be administered in methods of this invention by inhalation, via the nasal or oral routes, e.g., in a spray formulation also containing a suitable carrier.

Exemplary compounds useful in methods of the invention will now be described by reference to the illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Unless otherwise specified, the variables are as defined above in reference to Formula (I). Reactions may be performed between the melting point and the reflux temperature of the solvent, and preferably between 0° C. and the reflux temperature of the solvent.

SCHEME A

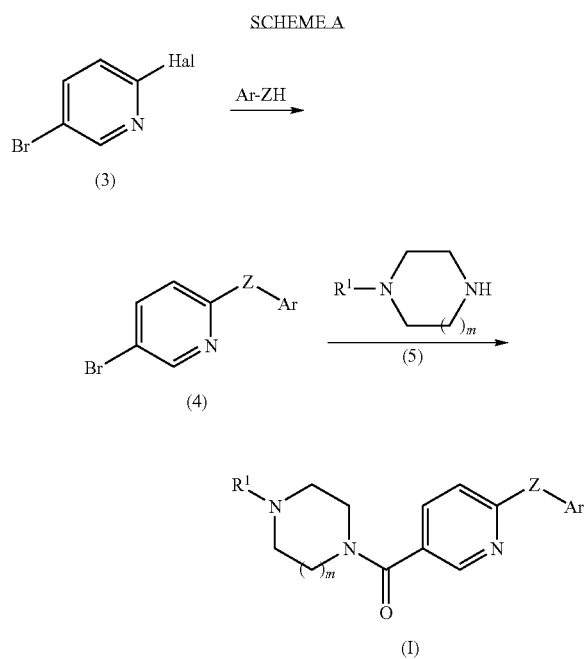

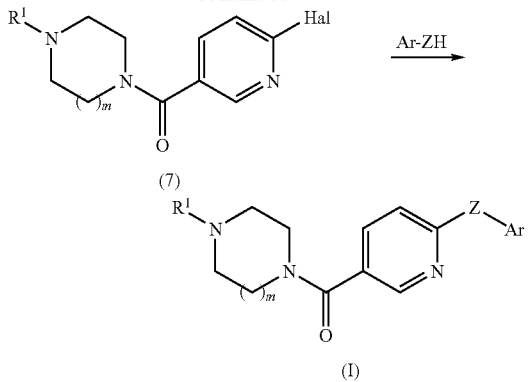

Amide coupling of pyridine carboxylic acids (6) (where A is OH) (6) with amines (5) provides amides (7). Alternatively, acid chlorides (6) (where A is Cl) may be reacted with amines (5) in the presence of a suitable base such as $Et_3N$, $iPr_2NEt$, pyridine, or a mixture thereof to form amides (7). One skilled in the art will recognize that $R^1$ may be replaced by a suitable amine protecting group and then introduced at a later point in the synthesis. Displacement of the Hal group as described in Scheme A provides compounds of Formula (I) where Y is N and $R^2$ is —Z—Ar.

Referring to Scheme A, 3-bromo-pyridines (3), where Hal is bromo, chloro, or fluoro, are commercially available or prepared using methods known to one skilled in the art. Displacement of the Hal substituent is accomplished by reaction with Ar—ZH reagents, in the presence of a suitable base such as $K_2CO_3$, $Na_2CO_3$, $Cs_2CO_3$, NaH, or a mixture thereof, in a polar solvent such as N,N-dimethylformamide (DMF), ethylene glycol dimethyl ether (DME), N,N-dimethylacetamide (DMA), dimethylsulfoxide (DMSO), or a mixture thereof, at a temperature between room temperature and the reflux temperature of the solvent, or subject to microwave irradiation, to provide ethers and thioethers (4). Transition metal-catalyzed reaction of bromides (4) with amines (5) and a CO equivalent, such as CO gas or $Mo(CO)_6$, in the presence of a suitable palladium (II) catalyst, and optional additives such as t-BuPHBF$_4^+$, provide compounds of Formula (I) where Y is N and $R^2$ is —Z—Ar. Alternatively, halogen-metal exchange of the bromine atom of (4) by treatment with n-BuLi or t-BuLi and quenching with a $CO_2$ equivalent provides the corresponding carboxylic acids. Amide coupling of such acids with amines (5), in the presence of coupling agents known to one skilled in the art, also provides compounds of Formula (I) where Y is N and $R^2$ is —Z—Ar.

SCHEME B

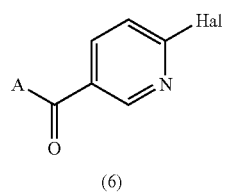

SCHEME B-1

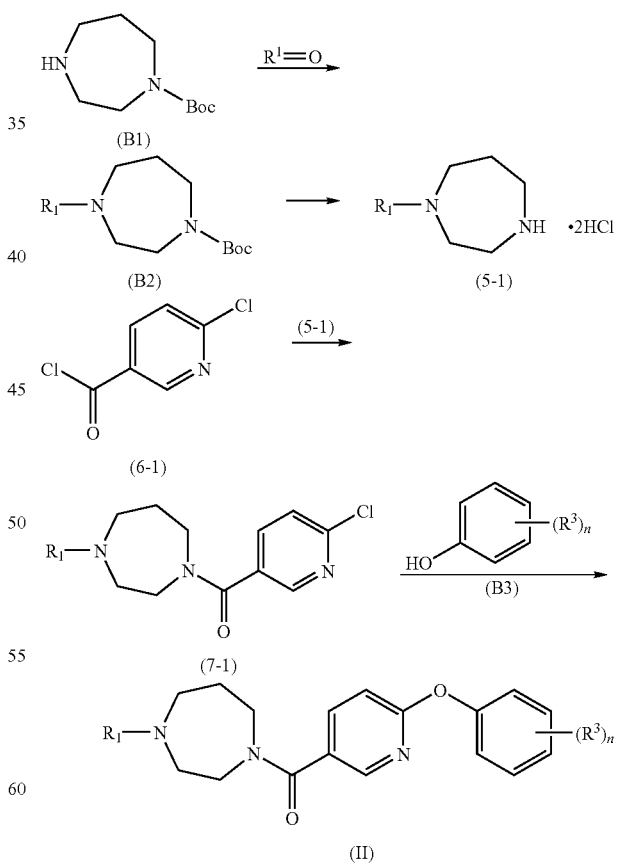

A method of making a compound of Formula (II), or a pharmaceutically acceptable salt thereof, is shown in Scheme B-1. A method of making a compound of Formula (II), or a pharmaceutically acceptable salt thereof, comprises reacting a compound of formula (7-1) with a compound of formula B3 in the presence of at least one equivalent of a first base, such as NaOH, KOH, $K_2CO_3$ or $Cs_2CO_3$, in a first organic solvent such as DMF, DMA, DME, DMSO, or acetonitrile, or a mixture thereof, to give a compound of Formula (II). In preferred embodiments, the reaction is heated at a temperature of about 100° C. In a further preferred embodiment, the compound of formula (7-1) is (6-chloro-pyridin-3-yl)-(4-cyclobutyl[1,4]diazepan-1-yl)-methanone, the compound of formula B3 is 4-fluorophenol, the first base is $Cs_2CO_3$ (preferably at least 1.5 equivalents, and more preferably about 2 equivalents), the first organic solvent is DMA (preferably, about 0.5-0.75 M solution), and the compound of Formula (II) is (4-cyclobutyl-[1,4]diazepan-1-yl)-[6-(4-fluoro-phenoxy)-pyridin-3-yl]-methanone.

The method of making a compound of Formula (II) further comprises reacting a compound of formula (5-1) with 6-chloronicotinyl chloride in the presence of a second base, such as aq. NaOH, aq. KOH, $Et_3N$, or $iPr_2NEt$, in a second organic solvent such as DCM, dichloroethane (DCE), toluene, or isopropyl acetate, to give a compound of formula (7-1). In a further preferred embodiment, the compound of formula (5-1) is 1-cyclobutyl-[1,4]diazepane dihydrochloride, the second base is 1 N aqueous NaOH, the second organic solvent is isopropyl acetate, and the compound of formula (7-1) is (6-chloro-pyridin-3-yl)-(4-cyclobutyl-[1,4]diazepan-1-yl)-methanone.

The method of making a compound of Formula (II) further comprises reacting a compound of formula B2 with a suitable acid, such as TFA or HCl, in a third organic solvent such as DCM, dioxane, or MeOH, or a mixture thereof, to give an amine salt of formula (5-1). In a further preferred embodiment, the compound of formula B2 is 4-cyclobutyl-[1,4]diazepane-1-carboxylic acid tert-butyl ester, the acid is HCl, the third organic solvent is dioxane, and the compound of formula (5-1) is 1-cyclobutyl-[1,4]diazepane dihydrochloride.

The method of making a compound of Formula (II) further comprises reacting tert-butylhomopiperazine-1-carboxylate (preferably, about 0.9-1.1 molar equivalents) via reductive amination with an aldehyde or ketone of formula $R^1$=O (preferably, about 0.9-1.1 molar equivalents) in the presence of at least one molar equivalent of a reducing agent, such as $NaB(OAc)_3H$ or $NaCNBH_3$, in a fourth organic solvent such as DCE, THF, EtOAc, ethanol, or methanol, to give a compound of formula B2. In a further preferred embodiment, $R^1$=O is cyclobutanone, the reducing agent is $NaB(OAc)_3H$ (preferably, at least 1.1 molar equivalents), the fourth organic solvent is dichloroethane (preferably, about 0.2 M-0.5 M solution), and the compound of formula B2 is 4-cyclobutyl-[1,4]diazepane-1-carboxylic acid tert-butyl ester.

In a preferred embodiment, a compound of Formula (II) is reacted with HCl (preferably, about 0.95 equivalents) in a fifth organic solvent such as ethanol, methanol, isopropanol, EtOAc, or an ethanol/$Et_2O$ mixture, to provide a pharmaceutically acceptable salt of the compound of Formula (II). In a further preferred embodiment, the compound of Formula (II) is (4-cyclobutyl-[1,4]diazepan-1-yl)-[6-(4-fluoro-phenoxy)-pyridin-3-yl]methanone, the fifth organic solvent is ethanol/$Et_2O$ (preferably, about 1:1 mixture), and the pharmaceutically acceptable salt of Formula (II) is (4-cyclobutyl-[1,4]diazepan-1-yl)-[6-(4-fluoro-phenoxy)-pyridin-3-yl]methanone hydrochloride monohydrate.

SCHEME C

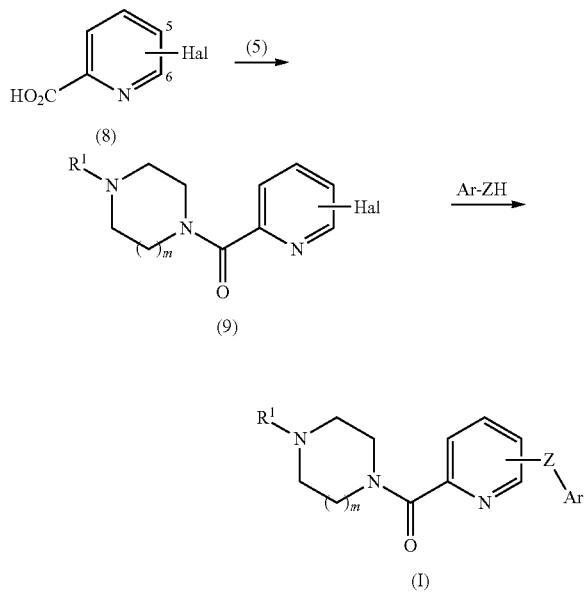

Referring to Scheme C, pyridines (8), where the Hal substituent is at the 5- or 6-position of the pyridine are coupled with amines (5) using general amide coupling methods to give amides (9). Replacement of the Hal substituent with —Z—Ar is accomplished by: 1) displacement by Ar—ZH reagents under basic conditions as described in Scheme A; or 2) Ullmann coupling in the presence of a suitable copper (I) catalyst, such as CuI, in a solvent such as DMF, DMSO, hexamethylphosphoramide (HMPA), or a mixture thereof, to provide compounds of Formula (I) where Y is $CR^a$, $R^a$ is —Z—Ar, and $R^2$ is —H or compounds of Formula (I) where Y is CH and $R^2$ is —Z—Ar.

SCHEME D

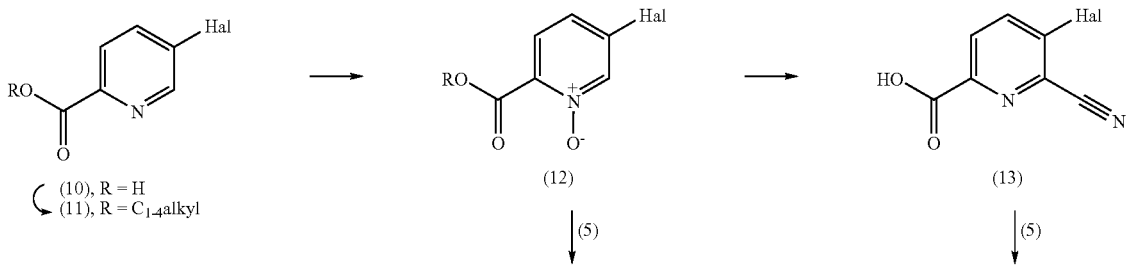

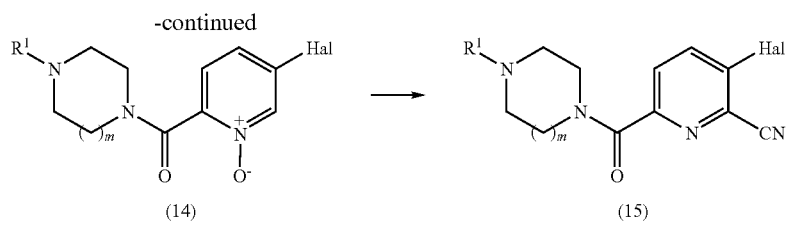

(14) → (15)

Compounds of Formula (I) where X is N, Y is CR$^a$, R$^a$ is —CN, and R$^2$ is —Z—Ar may be prepared from cyano amides (15), which are accessed as shown in Scheme D. Pyridine-2-carboxylic acids (10) are converted to the N-oxide analogs (12) by reaction with urea-hydrogen peroxide complex and trifluoroacetic acid anhydride. Installation of the cyano substituent is accomplished by reaction with trimethylsilyl cyanide (TMSCN) and dimethylcarbamyl chloride to provide nitrile acids (13). Alternatively, acids (10) may be esterified according to known methods to give esters (11), which may be converted to N-oxide esters (12). Following reaction with TMSCN and dimethylcarbamyl chloride to install the cyano group, hydrolysis of the ester group provides acids (13). Acids (13) are converted to cyano amides (15) by amide coupling with amines (5) as described in Scheme A. Alternatively, N-oxides (12), where R is H, may be coupled with amines (5) directly, using amide coupling methods as described in Scheme A. N-oxide amides (14) are reacted with TMSCN and dimethylcarbamyl chloride to give the corresponding cyano amides (15). Reaction of amides (15) via displacement or Ullmann coupling protocols as described in Schemes A and C provide compounds of Formula (I) where X is N, Y is CR$^a$, R$^a$ is —CN, and R$^2$ is —Z—Ar. Nitriles (15) are reduced to the corresponding aminomethyl analogs or hydrolyzed to form amides (not shown).

SCHEME E

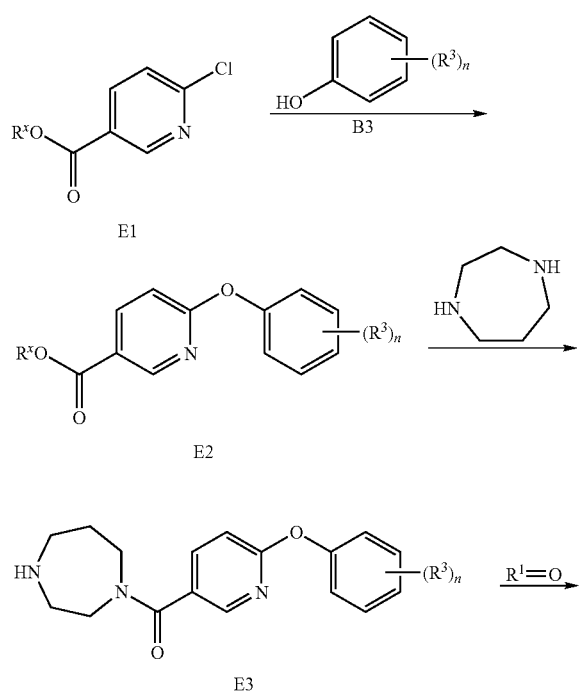

(II)

A method of making a compound of Formula (II), or a pharmaceutically acceptable salt thereof, is also shown in Scheme E. A method of making a compound of Formula (II), or a pharmaceutically acceptable salt thereof, comprises reacting a compound of formula E3 (preferably, about 1 equivalents) via reductive amination with a compound of formula R$^1$=O (preferably, at least 1 equivalent and more preferably, about 1.2 equivalents) in the presence of a suitable reducing agent such as NaB(OAc)$_3$H or NaCNBH$_3$ (preferably, at least 1 equivalent and, more preferably, about 1.5 equivalents), in a sixth organic solvent such as DCE, THF, EtOAc, ethanol, or methanol, at a temperature of about 0° C. to about 40° C., to give a compound of Formula (II). In a further preferred embodiment, the compound of formula E3 is (1,4-diazepan-1-yl)-(6-(4-fluorophenoxy)pyridin-3-yl)methanone, R$^1$=O is cyclobutanone, the reducing agent is NaB(OAc)$_3$H, the sixth organic solvent is EtOAc, and the compound of Formula (II) is (4-cyclobutyl-[1,4]diazepan-1-yl)-[6-(4-fluoro-phenoxy)-pyridin-3-yl]-methanone.

The method of making a compound of Formula (II), or a pharmaceutically acceptable salt thereof, further comprises reacting a compound of formula E2 (preferably, about 1 equivalent) with homopiperazine (preferably, at least 1 equivalent and more preferably, about 2.4 equivalents), in the presence of an organometallic reagent, such as an alkyl Grignard reagent or alkyllithium reagent (preferably, at least 1 equivalent and more preferably, about 1.5 equivalents), in an aprotic organic solvent, at a temperature between about 0° C. and about 30° C., to give a compound of formula E3. Examples of suitable organometallic reagents include R$^y$MgBr, R$^y$MgCl, or R$^y$Li, where R$^y$ is methyl, ethyl, propyl, isopropyl, butyl, or hexyl. Suitable aprotic organic solvents include THF, Et$_2$O, MTBE, or 2-methyl-TFT. In a preferred embodiment, the compound of formula E2 is ethyl 6-(4-fluorophenoxy)nicotinate, the organometallic reagent is hexyllithium, the aprotic organic solvent is THF, and the compound of formula E3 is [1,4]diazepan-1-yl-[6-(4-fluoro-phenoxy)-pyridin-3-yl]-methanone.

The method of making a compound of Formula (II), or a pharmaceutically acceptable salt thereof, further comprises reacting a compound of formula E1, where R$^x$ is methyl or ethyl (preferably, about 1 equivalent), with a compound of formula B3 (preferably, about 1.1 equivalents) in the presence of a base (such as Cs$_2$CO$_3$, K$_2$CO$_3$, NaOH, or KOH, or the like) (preferably, about 1.1 equivalents), in a polar, aprotic organic solvent, at a temperature between about room temperature and about 80° C., to give a compound of formula E2. Suitable polar, aprotic organic solvents include DMF, DMA, DMSO, or acetonitrile. In a further preferred embodiment, the compound of formula E1 is ethyl 6-chloronicotinate, the compound of formula B3 is 4-fluorophenol, the base is $Cs_2CO_3$, the polar, aprotic organic solvent is DMF, and the compound of formula E2 is ethyl 6-(4-fluorophenoxy)nicotinate.

The method of making a compound of Formula (II), or a pharmaceutically acceptable salt thereof, further comprises: a) diluting a solution of the compound of Formula (II) in EtOAc with ethanol; and b) treating the resulting solution with concentrated aqueous HCl (0.95 equivalents) to provide the hydrochloride salt of the compound of Formula (II). Preferably, the hydrochloride monohydrate of Formula (II) is formed. Preferably, the solution of the compound of Formula (II) in EtOAc is obtained from the reaction of a compound of formula E3 with a compound of formula $R^1$=O. In a preferred embodiment, the compound of Formula (II) is (4-cyclobutyl-[1,4]diazepan-1-yl)-[6-(4-fluoro-phenoxy)-pyridin-3-yl]-methanone. In a preferred embodiment, the pharmaceutically acceptable salt of a compound of Formula (II) is (4-cyclobutyl-[1,4]diazepan-1-yl)-[6-(4-fluoro-phenoxy)-pyridin-3-yl]methanone hydrochloride monohydrate.

Those skilled in the art will recognize that several of the chemical transformations described above may be performed in a different order than that depicted in the above Schemes.

Compounds of Formula (I) may be converted to their corresponding salts using methods known to those skilled in the art. For example, amines of Formula (I) may be treated with trifluoroacetic acid (TFA), HCl, or citric acid in a solvent such as diethyl ether ($Et_2O$), dichloromethane (DCM), tetrahydrofuran (THF), or methanol (MeOH) to provide the corresponding salt forms.

Compounds prepared according to the schemes described above may be obtained as single enantiomers, diastereomers, or regioisomers, by enantio-, diastero-, or regiospecific synthesis, or by resolution. Compounds prepared according to the schemes above may alternately be obtained as racemic (1:1) or non-racemic (not 1:1) mixtures or as mixtures of diastereomers or regioisomers. Where racemic and non-racemic mixtures of enantiomers are obtained, single enantiomers may be isolated using conventional separation methods known to one skilled in the art, such as chiral chromatography, recrystallization, diastereomeric salt formation, derivatization into diastereomeric adducts, biotransformation, or enzymatic transformation. Where regioisomeric or diastereomeric mixtures are obtained, single isomers may be separated using conventional methods such as chromatography or crystallization.

The following examples are provided to further illustrate the invention and various preferred embodiments.

EXAMPLES

Chemistry:

In preparing the compounds described in the examples below, the following general experimental methods were employed unless otherwise indicated.

Where solutions or mixtures were "concentrated", they were concentrated under reduced pressure using a rotary evaporator. Unless otherwise specified, reaction solutions were stirred at room temperature (rt) under a $N_{2(g)}$ atmosphere.

Normal phase flash column chromatography (FCC) was typically performed with RediSep® silica gel columns using 2 M $NH_3$ in MeOH/DCM as eluent, unless otherwise indicated.

Preparative Reversed-Phase high performance liquid chromatography (HPLC) was typically performed using a Gilson® instrument with a YMC-Pack ODS-A, 5 µm, 75×30 mm column, a flow rate of 25 mL/min, detection at 220 and 254 nm, with a 15% to 99% acetonitrile/(water/0.05% TFA) gradient (acidic conditions) or an acetonitrile/(water/20 mM $NH_4OH$) gradient (basic conditions).

Analytical Reversed-Phase HPLC (Method B) was performed using a Hewlett Packard instrument with a Zorbax Eclipse XBD-C8, 5 mm, 4.6×150 mm column, and a gradient of 1%-99% acetonitrile/water over 8.0 min.

Analytical Reversed-Phase HPLC (Method C) was performed using a Hewlett-Packard HP1100 HPLC System equipped with a Zorbax Eclipse XDB-C18; 4.6×50 mm, 1.8 µM column with a 2 mL/min flow rate and detection at 220 and 250 nm. The mobile phase was Solvent A: 0.1% TFA/water; Solvent B: 0.1% TFA/Acetonitrile. The gradient run was: 0 min (A:B, 75:25); 1.0 min (A:B, 75:25); 2.0 min (A:B, 5:95).

Trifluoroacetic acid salts were obtained by purification of the crude reaction product by preparative reverse phase HPLC.

In obtaining the characterization data described in the examples below, the following analytical protocols were followed unless otherwise indicated.

Mass spectra were obtained on an Agilent series 1100 MSD using electrospray ionization (ESI) in either positive or negative modes as indicated. Calculated mass corresponds to the exact mass.

NMR spectra were obtained on either a Bruker model DPX400 (400 MHz), DPX500 (500 MHz), DRX600 (600 MHz) spectrometer. The format of the $^1$H NMR data below is: chemical shift in ppm down field of the tetramethylsilane reference (multiplicity, coupling constant J in Hz, integration).

Chemical names were generated using ChemDraw Ultra 6.0.2 (CambridgeSoft Corp., Cambridge, Mass.).

Example 1

[6-(3,4-Dichloro-phenoxy)-pyridin-3-yl]-(4-isopropyl-piperazin-1-yl)-methanone

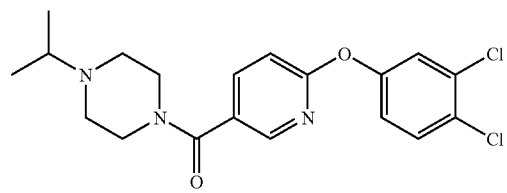

Step A; 5-Bromo-2-(3,4-dichloro-phenoxy)-pyridine

To a solution of 2,5-dibromopyridine (2.412 g, 10.18 mmol) in DMF (50 mL) was added $K_2CO_3$ (5.22 g, 37.8 mmol) and 3,4-dichlorophenol (2.66 g, 16.3 mmol). The mixture was heated at 90° C. for 18 h then allowed to cool to room temperature (rt). Water was added and the mixture was extracted with DCM. Purification by FCC provided the desired product (3.23 g, 100%). ¹H NMR (400 MHz, CDCl₃): 8.21 (dd, J=2.5, 0.8 Hz, 1H), 7.81 (dd, J=8.3, 3.0 Hz, 1H), 7.45 (d, J=8.8 Hz, 1H), 7.26 (d, J=1.5 Hz, 1H), 7.00 (dd, J=9.0, 2.5 Hz, 1H), 6.88 (dd, J=8.8, 0.8 Hz, 1H).

Step B

To a solution of 5-bromo-2-(3,4-dichloro-phenoxy)-pyridine (0.303 g, 0.949 mmol) in THF (4 mL) was added 1,8-diazabicyclo[5.4.0]undec-7-ene (DBU; 0.30 mL, 2.0 mmol), cyclopropyl piperazine (0.30 mL, 2.4 mmol), trans-di-m-acetatobis[2-(di-o-tolylphosphino)benzyl]di-palladium (II) (Hermann's catalyst; 36.7 mg, 0.039 mmol), t-BuPHBF₄⁺ (17.4 mg, 0.060 mmol), and Mo(CO)₆ (301 mg, 1.14 mmol). The reaction mixture was heated in the microwave for 6 min at 125° C., cooled to rt, then concentrated. Purification by FCC gave the desired product (284 mg, 76%). MS (ESI): mass calcd. for C₁₉H₂₁Cl₂N₃O₂, 393.10; m/z found, 394.7 [M+H]⁺. ¹H NMR (CDCl₃): 8.24 (dd, J=2.5, 0.8 Hz, 1H), 7.83 (dd, J=8.3, 2.5 Hz, 1H), 7.47 (d, J=8.8 Hz, 1H), 7.30 (d, J=2.8 Hz, 1H), 7.03 (dd, J=8.8, 2.5 Hz, 1H), 7.00 (dd, J=8.3, 0.8 Hz, 1H), 3.90-3.40 (br m, 4H), 2.74 (h, J=6.8 Hz, 1H), 2.64-2.43 (br m, 4H), 1.04 (d, J=7.1 Hz, 6H).

The compounds in Examples 2-42 were prepared using procedures analogous to those outlined in Example 1.

Example 2

(4-Isopropyl-piperazin-1-yl)-[6-(pyridin-3-yloxy)-pyridin-3-yl]-methanone

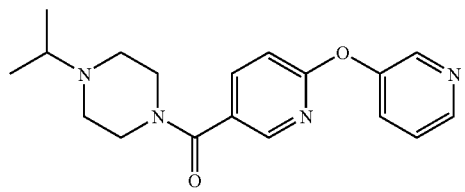 [SMILES: CC(C)N1CCN(C(=O)c2ccc(Oc3cccnc3)nc2)CC1]

MS (ESI): mass calcd. for C₁₈H₂₂N₄O₂, 326.17; m/z found, 327.7 [M+H]⁺.

¹H NMR (CDCl₃): 8.53 (d, J=2.7 Hz, 1H), 8.50 (dd, J=4.9, 1.1 Hz, 1H), 8.23 (d, J=2.7 Hz, 1H), 7.85 (dd, J=8.2, 2.5 Hz, 1H), 7.56-7.53 (m, 1H), 7.37 (dd, J=8.4, 2.5 Hz, 1H), 7.04 (d, J=8.8 Hz, 1H), 3.90-3.36 (m, 4H), 2.75 (h, J=6.8 Hz, 1H), 2.66-2.39 (m, 4H), 1.06 (d, J=6.0 Hz, 6H).

Example 3

(4-Isopropyl-piperazin-1-yl)-[6-(4-methylsulfanyl-phenoxy)-pyridin-3-yl]-methanone

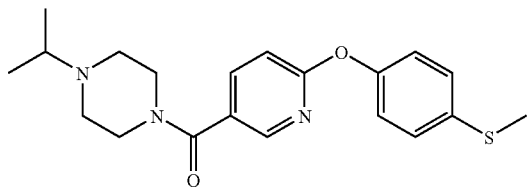 [SMILES: CSc1ccc(Oc2ccc(C(=O)N3CCN(C(C)C)CC3)cn2)cc1]

MS (ESI): mass calcd. for C₂₀H₂₅N₃O₂S, 371.17; m/z found, 372.7 [M+H]⁺.

¹H NMR (CDCl₃): 8.27 (d, J=2.5 Hz, 1H), 7.81 (dd, J=8.5, 2.2 Hz, 1H), 7.33 (d, J=8.8 Hz, 2H), 7.10 (d, J=9.0 Hz, 2H), 6.97 (d, J=8.1 Hz, 1H), 3.87-3.41 (m, 4H), 2.75 (h, J=6.6 Hz, 1H), 2.63-2.42 (m, 7H), 1.06 (d, J=6.3 Hz, 6H).

Example 4

[6-(3-Chloro-phenoxy)-pyridin-3-yl]-(4-isopropyl-piperazin-1-yl)-methanone

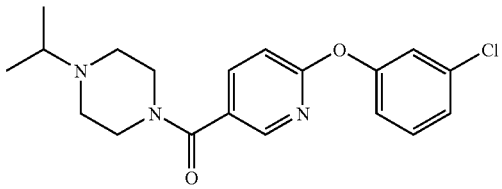 [SMILES: CC(C)N1CCN(C(=O)c2ccc(Oc3cccc(Cl)c3)nc2)CC1]

MS (ESI): mass calcd. for C₁₉H₂₂ClN₃O₂, 359.14; m/z found, 360.1 [M+H]⁺.

¹H NMR (CDCl₃): 8.26 (d, J=1.9 Hz, 1H), 7.83 (dd, J=8.5, 2.7 Hz, 1H), 7.34 (dd, J=8.0, 8.0 Hz, 1H), 7.23-7.20 (m, 1H), 7.18 (dd, J=2.2, 2.2 Hz, 1H), 7.07-7.04 (m, 1H), 6.99 (d, J=8.2 Hz, 1H), 3.87-3.38 (m, 4H), 2.74 (h, J=6.5 Hz, 1H), 2.65-2.41 (m, 4H), 1.05 (d, J=6.6 Hz, 6H).

Example 5

(4-Isopropyl-piperazin-1-yl)-(6-phenoxy-pyridin-3-yl)-methanone

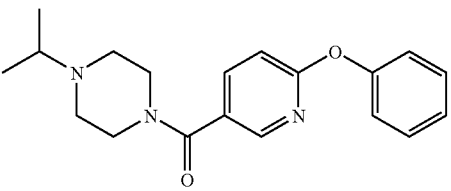 [SMILES: CC(C)N1CCN(C(=O)c2ccc(Oc3ccccc3)nc2)CC1]

MS (ESI): mass calcd. for C₁₉H₂₃N₃O₂, 325.18; m/z found, 326.7 [M+H]⁺.

¹H NMR (CDCl₃): 8.27 (d, J=2.7 Hz, 1H), 7.81 (dd, J=8.5, 2.5 Hz, 1H), 7.46-7.41 (m, 2H), 7.27-7.23 (m, 1H), 7.18-7.14 (m, 2H), 6.96 (d, J=8.5 Hz, 1H), 3.86-3.40 (m, 4H), 2.75 (h, J=6.6 Hz, 1H), 2.66-2.41 (m, 4H), 1.06 (d, J=6.3 Hz, 6H).

Example 6

[6-(4-Chloro-3-methyl-phenoxy)-pyridin-3-yl]-(4-isopropyl-piperazin-1-yl)-methanone

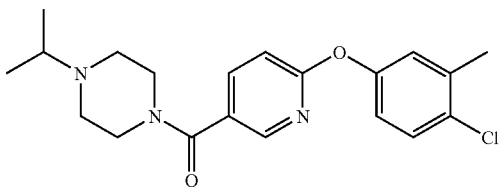 [SMILES: Cc1cc(Oc2ccc(C(=O)N3CCN(C(C)C)CC3)cn2)ccc1Cl]

MS (ESI): mass calcd. for $C_{20}H_{24}ClN_3O_2$, 373.16; m/z found, 374.7 $[M+H]^+$.
$^1$H NMR (CDCl$_3$): 8.26 (d, J=2.2 Hz, 1H), 7.82 (dd, J=8.8, 2.5 Hz, 1H), 7.28 (d, J=8.5 Hz, 1H), 7.04 (d, J=3.0 Hz, 1H), 6.98 (d, J=8.2 Hz, 1H), 6.94 (dd, J=8.2, 2.7 Hz, 1H), 3.87-3.41 (m, 4H), 2.75 (h, J=6.3 Hz, 1H), 2.65-2.43 (m, 4H), 1.06 (d, J=6.6 Hz, 6H).

Example 7

3-[5-(4-Isopropyl-piperazine-1-carbonyl)-pyridin-2-yloxy]-benzonitrile

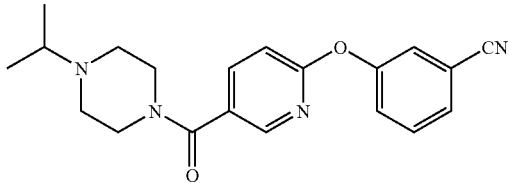 [SMILES: CC(C)N1CCN(C(=O)c2ccc(Oc3cccc(C#N)c3)nc2)CC1]

MS (ESI): mass calcd. for $C_{20}H_{22}N_4O_2$, 350.17; m/z found, 351.7 $[M+H]^+$.
$^1$H NMR (CDCl$_3$): 8.24 (dd, J=2.2, 0.8 Hz, 1H), 7.87 (dd, J=8.2, 2.5 Hz, 1H), 7.55-7.53 (m, 2H), 7.50-7.49 (m, 1H), 7.45-7.41 (m, 1H), 7.05 (dd, J=8.2, 0.5 Hz, 1H), 3.87-3.41 (m, 4H), 2.76 (h, J=6.9 Hz, 1H), 2.68-2.44 (m, 4H), 1.06 (d, J=6.6 Hz, 6H).

Example 8

[6-(4-Chloro-phenoxy)-pyridin-3-yl]-(4-isopropyl-piperazin-1-yl)-methanone

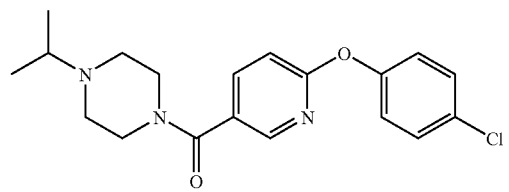 [SMILES: CC(C)N1CCN(C(=O)c2ccc(Oc3ccc(Cl)cc3)nc2)CC1]

MS (ESI): mass calcd. for $C_{19}H_{22}ClN_3O_2$, 359.14; m/z found, 360.7 $[M+H]^+$.
$^1$H NMR (CDCl$_3$): 8.25 (dd, J=2.5, 1.1 Hz, 1H), 7.83 (dd, J=8.5, 2.5 Hz, 1H), 7.41-7.37 (m, 2H), 7.13-7.09 (m, 2H), 6.99 (dd, J=8.8, 0.5 Hz, 1H), 3.85-3.41 (m, 4H), 2.75 (h, J=6.3 Hz, 1H), 2.65-2.43 (m, 4H), 1.06 (d, J=6.6 Hz, 6H).

Example 9

(4-Cyclopropyl-[1,4]diazepan-1-yl)-[6-(3,4-dichloro-phenoxy)-Pyridin-3-yl]-methanone

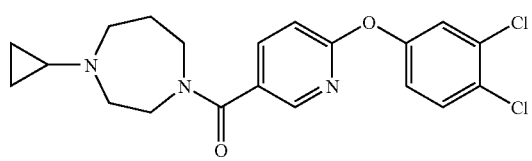 [SMILES: O=C(c1ccc(Oc2ccc(Cl)c(Cl)c2)nc1)N1CCCN(C2CC2)CC1]

MS (ESI): mass calcd. for $C_{20}H_{21}Cl_2N_3O_2$, 405.10; m/z found, 406.7 $[M+H]^+$.
$^1$H NMR (CDCl$_3$): 8.22 (br s, 1H), 7.82-7.78 (m, 1H), 7.46 (d, J=8.8 Hz, 1H), 7.28 (d, J=2.5 Hz, 1H), 7.02 (dd, J=8.8, 2.6 Hz, 1H), 6.98 (br d, J=8.5 Hz, 1H), 3.77-3.71 (m, 1H), 3.52-3.44 (m, 3H), 3.43-3.38 (m, 1H), 2.97-2.92 (m, 1H), 2.89-2.72 (m, 3H), 1.98-1.71 (m, 3H), 0.52-0.33 (m, 4H).

Example 10

[6-(4-Chloro-phenoxy)-pyridin-3-yl]-(4-cyclopropyl-[1,4]diazepin-1-yl)-methanone

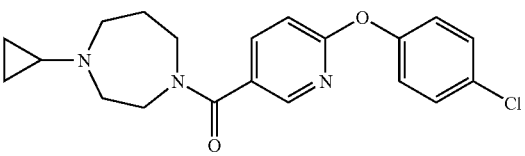 [SMILES: O=C(c1ccc(Oc2ccc(Cl)cc2)nc1)N1CCCN(C2CC2)CC1]

MS (ESI): mass calcd. for $C_{20}H_{22}ClN_3O_2$, 371.14; m/z found, 372.4 $[M+H]^+$.
$^1$H NMR (CDCl$_3$): 8.23 (d, J=2.2 Hz, 1H), 7.82-7.76 (m, 1H), 7.40-7.35 (m, 2H), 7.12-7.07 (m, 2H), 6.96 (d, J=8.8 Hz, 1H), 3.78-3.71 (m, 2H), 3.53-3.45 (m, 2H), 2.98-2.93 (m, 1H), 2.88-2.75 (m, 3H), 1.97-1.75 (m, 3H), 0.52-0.34 (m, 4H).

Example 11

3-[5-(4-Cyclopropyl-[1,4]diazepane-1-carbonyl)-pyridin-2-yloxy]-benzonitrile

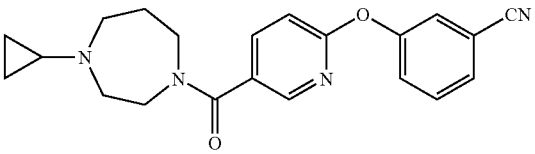 [SMILES: N#Cc1cccc(Oc2ccc(C(=O)N3CCCN(C4CC4)CC3)cn2)c1]

MS (ESI): mass calcd. for $C_{21}H_{22}N_4O_2$, 362.17; m/z found, 363.7 $[M+H]^+$.
$^1$H NMR (CDCl$_3$): 8.23 (br s, 1H), 7.87-7.82 (m, 1H), 7.55-7.51 (m, 2H), 7.50 (br s, 1H), 7.45-7.41 (m, 1H), 7.04 (d, J=8.5 Hz, 1H), 3.79-3.74 (m, 2H), 3.55-3.49 (m, 2H), 3.00-2.95 (m, 1H), 2.89-2.78 (m, 3H), 2.00-1.79 (m, 3H), 0.54-0.36 (m, 4H).

Example 12

[6-(4-Chloro-3-methyl-phenoxy)-pyridin-3-yl]-(4-cyclopropyl-[1,4]diazepan-1-yl)-methanone

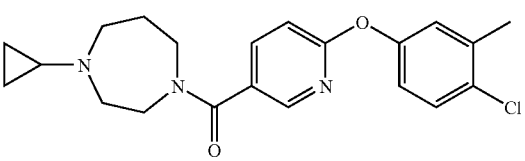

MS (ESI): mass calcd. for $C_{21}H_{24}ClN_3O_2$, 385.16; m/z found, 386.2 [M+H]$^+$.
$^1$H NMR (400 MHz, CDCl$_3$): 8.25 (d, J=1.9 Hz, 1H), 7.82-7.77 (m, 1H), 7.38 (d, J=8.2 Hz, 1H), 7.04 (d, J=2.7 Hz, 1H), 6.99-6.92 (m, 2H), 3.78-3.72 (m, 2H), 3.56-3.47 (m, 2H), 3.00-2.94 (m, 1H), 2.89-2.76 (m, 3H), 1.99-1.76 (m, 3H), 0.53-0.35 (m, 4H).

Example 13

(4-Cyclopropyl-[1,4]diazepan-1-yl)-(6-phenoxy-pyridin-3-yl)-methanone

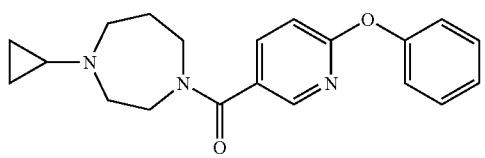 [SMILES: O=C(c1ccc(Oc2ccccc2)nc1)N1CCCN(C2CC2)CC1]

MS (ESI): mass calcd. for $C_{20}H_{23}N_3O_2$, 337.18; m/z found, 338.2 [M+H]$^+$.
$^1$H NMR (CDCl$_3$): 8.23 (d, J=2.5 Hz, 1H), 7.82-7.76 (m, 1H), 7.46-7.41 (m, 2H), 7.27-7.23 (m, 1H), 7.19-7.14 (m, 2H), 6.95 (d, J=8.2 Hz, 1H), 3.78-3.73 (m, 2H), 3.56-3.48 (m, 2H), 3.00-2.94 (m, 1H), 2.89-2.76 (m, 3H), 1.99-1.76 (m, 3H), 0.53-0.35 (m, 4H).

Example 14

(4-Cyclobutyl-[1,4]diazepan-1-yl)-[6-(3,4-dichloro-phenoxy)-pyridin-3-yl]-methanone

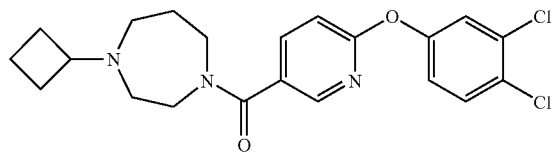 [SMILES: O=C(c1ccc(Oc2ccc(Cl)c(Cl)c2)nc1)N1CCCN(C2CCC2)CC1]

MS (ESI): mass calcd. for $C_{21}H_{23}Cl_2N_3O_2$, 419.12; m/z found, 420.3 [M+H]$^+$.
$^1$H NMR (CDCl$_3$): 8.23 (br s, 1H), 7.82 (dd, J=8.3, 2.3 Hz, 1H), 7.47 (d, J=8.8 Hz, 1H), 7.29 (d, J=3.0 Hz, 1H), 7.03 (dd, J=8.6, 2.3 Hz, 1H), 6.99 (d, J=8.6 Hz, 1H), 3.80-3.73 (m, 2H), 3.57-3.48 (m, 2H), 2.96-2.81 (m, 1H), 2.65-2.59 (m, 1H), 2.53-2.41 (m, 3H), 2.10-1.91 (m, 3H), 1.89-1.65 (m, 5H).

Example 15

[6-(3,4-Dichloro-phenoxy)-pyridin-3-yl]-(4-isopropyl-[1,4]diazepan-1-yl)-methanone

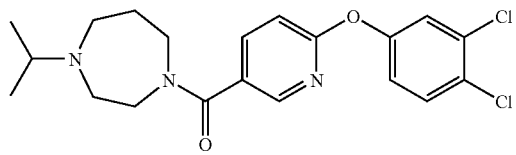 [SMILES: CC(C)N1CCCN(C(=O)c2ccc(Oc3ccc(Cl)c(Cl)c3)nc2)CC1]

MS (ESI): mass calcd. for $C_{20}H_{23}Cl_2N_3O_2$, 407.12; m/z found, 408.2 [M+H]$^+$.
$^1$H NMR (CDCl$_3$): 8.24 (br s, 1H), 7.82 (dd, J=8.3, 2.5 Hz, 1H), 7.47 (d, J=8.6 Hz, 1H), 7.29 (d, J=3.0 Hz, 1H), 7.03 (dd, J=8.3, 1.3 Hz, 1H), 6.99 (d, J=8.4 Hz, 1H), 3.78-3.72 (m, 2H), 3.51-3.45 (m, 2H), 2.99-2.84 (m, 1H), 2.82-2.76 (m, 1H), 2.71-2.58 (m, 3H), 1.95-1.86 (m, 1H), 1.81-1.72 (m, 1H), 1.06-0.94 (m, 6H).

Example 16

[6-(4-Chloro-3-methyl-phenoxy)-pyridin-3-yl]-(4-cyclobutyl-[1,4]diazepan-1-yl)-methanone

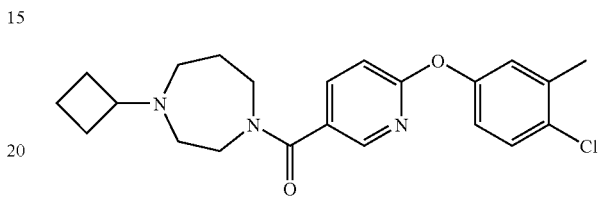

MS (ESI): mass calcd. for $C_{22}H_{26}ClN_3O_2$, 399.17; m/z found, 400.3 [M+H]$^+$.
$^1$H NMR (CDCl$_3$): 8.23 (br s, 1H), 7.78 (dd, J=8.0, 2.5 Hz, 1H), 7.35 (d, J=8.8 Hz, 1H), 7.01 (d, J=2.5 Hz, 1H), 6.96-6.89 (m, 2H), 3.78-3.71 (m, 2H), 3.56-3.46 (m, 2H), 2.93-2.79 (m, 1H), 2.64-2.57 (m, 1H), 2.52-2.39 (m, 3H), 2.37 (s, 3H), 2.09-1.90 (m, 3H), 1.88-1.54 (m, 5H).

Example 17

[6-(4-Chloro-3-methyl-phenoxy)-pyridin-3-yl]-(4-isopropyl-[1,4]diazepan-1-yl)-methanone

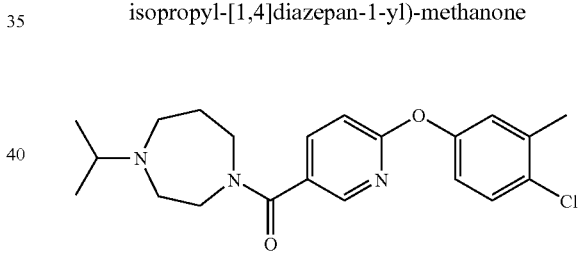

MS (ESI): mass calcd. for $C_{21}H_{26}ClN_3O_2$, 387.90; m/z found, 388.3 [M+H]$^+$.
$^1$H NMR (CDCl$_3$): 8.24 (br s, 1H), 7.79 (dd, J=8.6, 2.3 Hz, 1H), 7.36 (d, J=8.6 Hz, 1H), 7.03 (d, J=2.8 Hz, 1H), 6.97-6.90 (m, 2H), 3.78-3.71 (m, 2H), 3.53-3.45 (m, 2H), 2.99-2.83 (m, 1H), 2.83-2.74 (m, 1H), 2.71-2.57 (m, 3H), 1.96-1.85 (m, 1H), 1.82-1.70 (m, 1H), 1.07-0.93 (m, 6H).

Example 18

(4-Cyclopropyl-[1,4]diazepan-1-yl)-[6-(4-fluoro-phenoxy)-pyridin-3-yl]-methanone

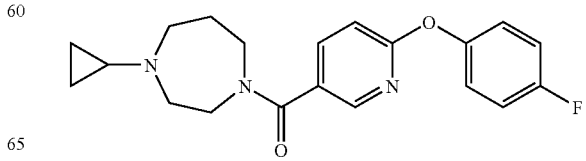

MS (ESI): mass calcd. for $C_{20}H_{22}FN_3O_2$, 355.17; m/z found, 356.4 [M+H]$^+$.
$^1$H NMR (CDCl$_3$): 8.23 (d, J=2.3 Hz, 1H), 7.81-7.75 (m, 1H), 7.14-7.08 (m, 4H), 6.94 (d, J=8.6 Hz, 1H), 3.77-3.70 (m, 2H), 3.54-3.39 (m, 2H), 2.99-2.93 (m, 1H), 2.88-2.73 (m, 3H), 1.98-1.73 (m, 3H), 0.53-0.31 (m, 4H).

Example 19

(4-Cyclobutyl-[1,4]diazepan-1-yl)-[6-(4-fluoro-phenoxy)-pyridin-3-yl]-methanone

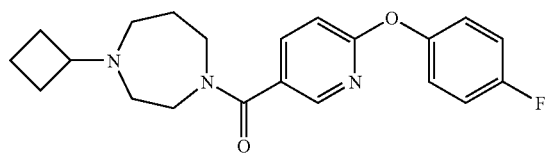

MS (ESI): mass calcd. for $C_{21}H_{24}FN_3O_2$, 369.19; m/z found, 370.4 [M+H]$^+$.
$^1$H NMR (CDCl$_3$): 8.23 (br s, 1H), 7.79 (dd, J=8.6, 2.8 Hz, 1H), 7.13-7.08 (m, 4H), 6.95 (dd, J=8.1, 0.5 Hz, 1H), 3.81-3.71 (m, 2H), 3.58-3.46 (m, 2H), 2.96-2.78 (m, 1H), 2.66-2.58 (m, 1H), 2.53-2.39 (m, 3H), 0.21-1.54 (m, 8H).

Example 20

3-[5-(4-Cyclobutyl-[1,4]diazepane-1-carbonyl)-pyridin-2-yloxy]-benzonitrile

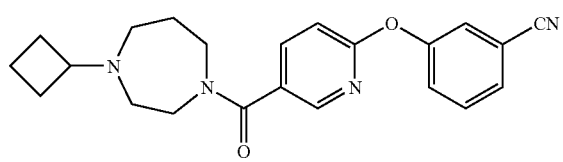 [SMILES: N#Cc1cccc(Oc2ccc(C(=O)N3CCCN(C4CCC4)CC3)cn2)c1]

MS (ESI): mass calcd. for $C_{22}H_{24}N_4O_2$, 376.19; m/z found, 377.5 [M+H]$^+$.
$^1$H NMR (CDCl$_3$): 8.22 (br s, 1H), 7.84 (dd, J=8.6, 2.8 Hz, 1H), 7.56-7.46 (m, 3H), 7.44-7.38 (m, 1H), 7.03 (dd, J=8.3, 0.5 Hz, 1H), 3.82-3.71 (m, 2H), 3.60-3.45 (m, 2H), 2.87-2.79 (m, 1H), 2.67-2.58 (m, 1H), 2.54-2.39 (m, 3H), 2.12-1.52 (m, 8H).

Example 21

(4-Cyclobutyl-[1,4]diazepan-1-yl)-(6-phenoxy-pyridin-3-yl)-methanone

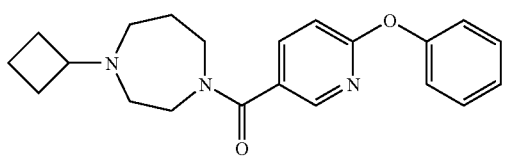

MS (ESI): mass calcd. for $C_{21}H_{25}N_3O_2$, 351.19; m/z found, 352.5 [M+H]$^+$.
$^1$H NMR (CDCl$_3$): 8.25 (br s, 1H), 7.78 (dd, J=8.8, 2.5 Hz, 1H), 7.45-7.39 (m, 2H), 7.26-7.21 (m, 1H), 7.17-7.13 (m, 2H), 6.93 (d, J=8.5 Hz, 1H), 3.81-3.71 (m, 2H), 3.58-3.47 (m, 2H), 2.94-2.79 (m, 1H), 2.66-2.58 (m, 1H), 2.54-2.39 (m, 3H), 2.12-1.92 (m, 3H), 1.89-1.55 (m, 5H).

Example 22

(4-Cyclopropyl-piperazin-1-yl)-[6-(4-fluoro-phenoxy)-pyridin-3-yl]-methanone

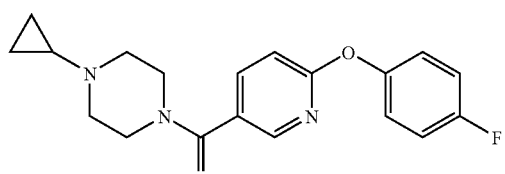

MS (ESI): mass calcd. for $C_{19}H_{20}FN_3O_2$, 341.15; m/z found, 342.5 [M+H]$^+$.
$^1$H NMR (CDCl$_3$): 8.24 (dd, J=2.3, 0.5 Hz, 1H), 7.81 (dd, J=8.6, 2.5 Hz, 1H), 7.15-7.08 (m, 4H), 6.96 (dd, J=8.3, 0.8 Hz, 1H), 3.84-3.33 (m, 4H), 2.76-2.49 (m, 4H), 1.70-1.61 (m, 4H), 0.54-0.37 (m, 4H).

Example 23

[6-(3-Chloro-phenoxy)-pyridin-3-yl]-(4-cyclopropyl-[1,4]diazepan-1-yl)-methanone

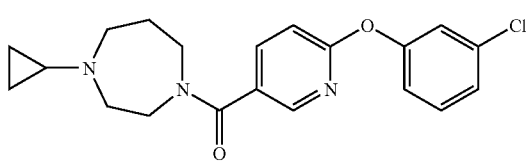

MS (ESI): mass calcd. for $C_{20}H_{22}ClN_3O_2$, 371.14; m/z found, 372.5 [M+H]$^+$.
$^1$H NMR (CDCl$_3$): 8.25 (d, J=2.2 Hz, 1H), 7.83-7.77 (m, 1H), 7.37-7.32 (m, 1H), 7.23-7.20 (m, 1H), 7.19-7.16 (m, 1H), 7.07-7.04 (m, 1H), 6.99-6.95 (m, 1H), 3.78-3.71 (m, 2H), 3.53-3.47 (m, 2H), 2.98-2.93 (m, 1H), 2.88-2.76 (m, 3H), 1.97-1.76 (m, 3H), 0.52-0.34 (m, 4H).

Example 24

[6-(3-Chloro-phenoxy)-Pyridin-3-yl]-(4-cyclobutyl-[1,4]diazepan-1-yl)-methanone

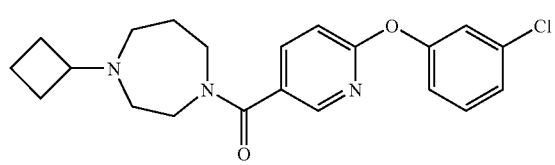 [SMILES: O=C(c1ccc(Oc2cccc(Cl)c2)nc1)N1CCCN(C2CCC2)CC1]

MS (ESI): mass calcd. for $C_{21}H_{21}ClN_3O_2$, 385.16; m/z found, 386.2 [M+H]$^+$.
$^1$H NMR (CDCl$_3$): 8.25 (br s, 1H), 7.81 (dd, J=8.2, 2.2 Hz, 1H), 7.36-7.32 (m, 1H), 7.23-7.19 (m, 1H), 7.19-7.16 (m, 1H), 7.07-7.03 (m, 1H), 6.97 (dd, J=8.5, 0.8 Hz, 1H), 3.81-

3.72 (m, 2H), 3.58-3.47 (m, 2H), 2.97-2.80 (m, 1H). 2.68-2.58 (m, 1H), 2.55-2.40 (m, 3H), 2.11-1.93 (m, 3H), 1.90-1.55 (m, 5H).

Example 25

[6-(4-Chloro-phenoxy)-pyridin-3-yl]-(4-cyclobutyl-[1,4]diazepan-1-yl)-methanone

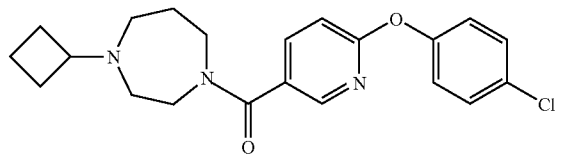

MS (ESI): mass calcd. for C$_{21}$H$_{21}$ClN$_3$O$_2$, 385.16; m/z found, 386.5 [M+H]$^+$.

$^1$H NMR (CDCl$_3$): 8.23 (s, 1H), 7.80 (dd, J=8.5, 2.7 Hz, 1H), 7.40-7.35 (m, 2H), 7.12-7.07 (m, 2H), 6.96 (d, J=8.2 Hz, 1H), 3.79-3.72 (m, 2H), 3.57-3.47 (m, 2H), 2.95-2.79 (m, 1H), 2.65-2.58 (m, 1H), 2.53-2.39 (m, 3H), 2.09-1.92 (m, 3H), 1.88-1.56 (m, 5H).

Example 26

(4-Cyclobutyl-[1,4]diazepan-1-yl)-[6-(3,4-difluoro-phenoxy)-pyridin-3-yl]-methanone

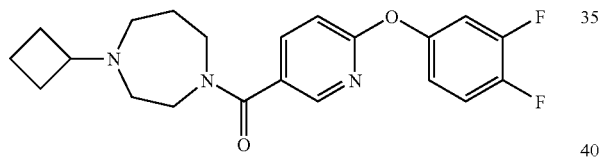

MS (ESI): mass calcd. for C$_{21}$H$_{23}$F$_2$N$_3$O$_2$F, 387.18; m/z found, 388.5 [M+H]$^+$. $^1$H NMR (CDCl$_3$): 8.23 (s, 1H), 7.81 (dd, J=8.8, 2.5 Hz, 1H), 7.24-7.16 (m, 1H), 7.05-6.96 (m, 2H), 6.92-6.86 (m, 1H), 3.80-3.73 (m, 2H), 3.57-3.48 (m, 2H), 2.95-2.79 (m, 1H), 2.66-2.59 (m, 1H), 2.54-2.40 (m, 3H), 2.11-1.92 (m, 3H), 1.89-1.60 (m, 5H).

Example 27

(4-Cyclopropyl-[1,4]diazepan-1-yl)-[6-(3,4-difluoro-phenoxy)-pyridin-3-yl]-methanone

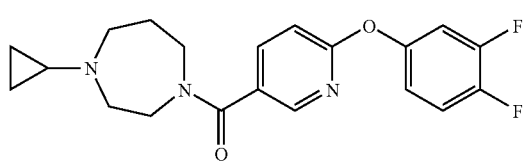 [SMILES: O=C(c1ccc(Oc2ccc(F)c(F)c2)nc1)N1CCCN(C2CC2)CC1]

MS (ESI): mass calcd. for C$_{20}$H$_{21}$F$_2$N$_3$O$_2$, 373.16; m/z found, 374.5 [M+H]$^+$.

$^1$H NMR (CDCl$_3$): 8.23 (d, J=2.0 Hz, 1H), 7.84-7.77 (m, 1H), 7.24-7.15 (m, 1H), 7.06-6.95 (m, 2H), 6.93-6.87 (m, 1H), 3.78-3.70 (m, 2H), 3.54-3.45 (m, 2H), 2.99-2.92 (m, 1H), 2.89-2.76 (m, 3H), 1.98-1.75 (m, 3H), 0.53-0.33 (m, 4H).

Example 28

[6-(3,4-Difluoro-phenoxy)-pyridin-3-yl]-(4-isopropyl-piperazin-1-yl)-methanone

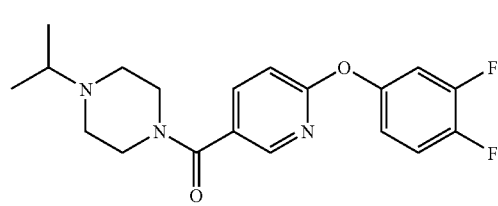 [SMILES: CC(C)N1CCN(C(=O)c2ccc(Oc3ccc(F)c(F)c3)nc2)CC1]

MS (ESI): mass calcd. for C$_{19}$H$_{21}$F$_2$N$_3$O$_2$, 361.16; m/z found, 362.5 [M+H]$^+$.

$^1$H NMR (CDCl$_3$): 8.24 (dd, J=2.5, 1.0 Hz, 1H), 7.83 (dd, J=8.3, 2.3 Hz, 1H), 7.24-7.16 (m, 1H), 7.06-6.97 (m, 2H), 6.92-6.87 (m, 1H), 3.88-3.36 (m, 4H), 2.74 (h, J=6.8 Hz, 1H), 2.66-2.42 (m, 4H), 1.05 (d, J=6.6 Hz, 1H).

Example 29

(4-Cyclobutyl-[1,4]diazepan-1-yl)-[6-(2-fluoro-phenoxy)-pyridin-3-yl]-methanone

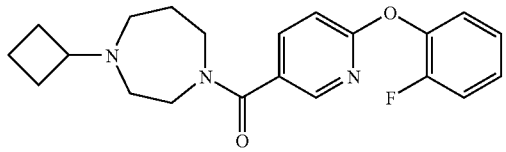

MS (ESI): mass calcd. for C$_{21}$H$_{24}$FN$_3$O$_2$, 369.19; m/z found, 370.5 [M+H]$^+$.

$^1$H NMR (CDCl$_3$): 8.20 (br s, 1H), 7.81 (dd, J=8.6, 2.0 Hz, 1H), 7.26-7.16 (m, 5H), 7.02 (dd, J=8.3, 1.0 Hz, 1H), 3.81-3.71 (m, 2H), 3.59-3.46 (m, 2H), 2.96-2.78 (m, 1H), 2.66-2.58 (m, 1H), 2.54-2.39 (m, 3H), 2.11-1.91 (m, 3H), 1.90-1.55 (m, 5H).

Example 30

(4-Cyclobutyl-[1,4]diazepan-1-yl)-[6-(2,4-difluoro-phenoxy)-pyridin-3-yl]-methanone

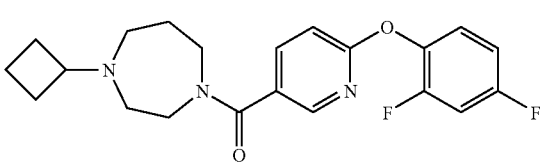 [SMILES: O=C(c1ccc(Oc2ccc(F)cc2F)nc1)N1CCCN(C2CCC2)CC1]

MS (ESI): mass calcd. for C$_{21}$H$_{23}$F$_2$N$_3$O$_2$, 387.18; m/z found, 388.5 [M+H]$^+$.

$^1$H NMR (CDCl$_3$): 8.18 (br s, 1H), 7.81 (dd, J=8.8, 2.5 Hz, 1H), 7.22-7.16 (m, 1H), 7.03 (dd, J=8.5, 0.8 Hz, 1H), 6.99-

6.89 (m, 2H), 3.80-3.72 (m, 2H), 3.56-3.47 (m, 2H), 2.94-2.79 (m, 1H), 2.65-2.59 (m, 1H), 2.53-2.40 (m, 3H), 2.10-1.92 (m, 3H), 1.92-1.56 (m, 5H).

Example 31

(4-Cyclopropyl-[1,4]diazepan-1-yl)-[6-(2-fluorophenoxy)-pyridin-3-yl]-methanone

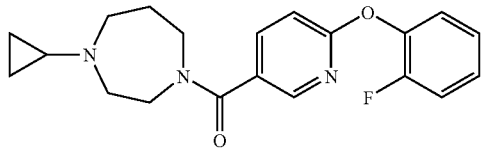 [SMILES: O=C(c1ccc(Oc2ccccc2F)nc1)N1CCCN(C2CC2)CC1]

MS (ESI): mass calcd. for $C_{20}H_{22}FN_3O_2$, 355.17; m/z found, 356.5 [M+H]$^+$.

$^1$H NMR (CDCl$_3$): 8.20 (d, J=2.0 Hz, 1H), 7.83-7.77 (m, 1H), 7.26-7.1 (m, 5H), 7.03 (d, J=8.6 Hz, 1H), 3.78-3.69 (m, 2H), 3.55-3.45 (m, 2H), 2.98-2.91 (m, 1H), 2.88-2.75 (m, 3H), 1.97-1.75 (m, 3H), 0.53-0.33 (m, 4H).

Example 32

(4-Cyclopropyl-[1,4]diazepan-1-yl)-[6-(2,4-difluorophenoxy)-pyridin-3-yl]-methanone

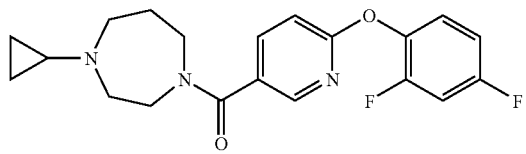 [SMILES: O=C(c1ccc(Oc2ccc(F)cc2F)nc1)N1CCCN(C2CC2)CC1]

MS (ESI): mass calcd. for $C_{20}H_{21}F_2N_3O_2$, 373.16; m/z found, 374.5 [M+H]$^+$.

$^1$H NMR (CDCl$_3$): 8.18 (d, J=2.0 Hz, 1H), 7.83-7.77 (m, 1H), 7.24-7.16 (m, 1H), 7.03 (d, J=8.6 Hz, 1H), 7.00-6.89 (m, 2H), 3.77-3.70 (m, 2H), 3.53-3.45 (m, 2H), 2.98-2.93 (m, 1H), 2.87-2.75 (m, 3H), 1.98-1.75 (m, 3H), 0.52-0.33 (m, 4H).

Example 33

(4-Cyclobutyl-[1,4]diazepan-1-yl)-[6-(3,5-dichlorophenoxy)-pyridin-3-yl]-methanone

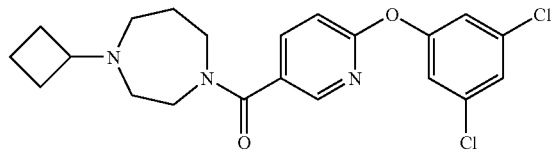 [SMILES: O=C(c1ccc(Oc2cc(Cl)cc(Cl)c2)nc1)N1CCCN(C2CCC2)CC1]

MS (ESI): mass calcd. for $C_{21}H_{23}Cl_2N_3O_2$, 419.12; m/z found, 420.5 [M+H]$^+$.

$^1$H NMR (CDCl$_3$): 8.25 (br s, 1H), 7.83 (dd, J=8.3, 2.3 Hz, 1H), 7.22 (dd, J=1.8, 1.8 Hz, 1H), 7.08 (d, J=2.0 Hz, 1H), 6.99 (dd, J=8.3, 0.5 Hz, 1H), 3.82-2.60 (m, 1H), 2.55-2.41 (m, 3H), 2.12-1.94 (m, 3H), 1.90-1.57 (m, 5H).

Example 34

(4-Cyclopropyl-[1,4]diazepan-1-yl)-[6-(2,5-difluorophenoxy)-pyridin-3-yl]-methanone

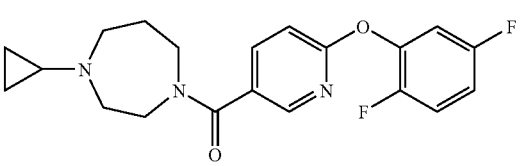 [SMILES: O=C(c1ccc(Oc2cc(F)ccc2F)nc1)N1CCCN(C2CC2)CC1]

MS (ESI): mass calcd. for $C_{20}H_{21}F_2N_3O_2$, 373.16; m/z found, 374.5 [M+H]$^+$.

$^1$H NMR (CDCl$_3$): 8.20 (d, J=1.9 Hz, 1H), 7.84-7.79 (m, 1H), 7.18-7.12 (m, 1H), 7.04 (d, J=8.5 Hz, 1H), 7.02-6.97 (m, 1H), 6.95-6.89 (m, 1H), 3.78-2.71 (m, 2H), 3.53-3.46 (m, 2H), 2.98-2.93 (m, 1H), 2.87-2.76 (m, 3H), 1.97-1.76 (m, 3H), 0.51-0.35 (m, 4H).

Example 35

(4-Cyclopropyl-[1,4]diazepan-1-yl)-[6-(3,5-dichlorophenoxy)-pyridin-3-yl]-methanone

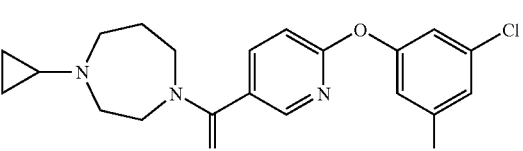

MS (ESI): mass calcd. for $C_{20}H_{21}Cl_2N_3O_2$, 405.10; m/z found, 406.4 [M+H]$^+$.

$^1$H NMR (CDCl$_3$): 8.25 (br s, 1H), 7.85-7.79 (m, 1H), 7.23 (dd, J=1.9, 1.9 Hz, 1H), 7.09 (d, J=1.6 Hz, 1H), 6.99 (d, J=8.2 Hz, 1H), 3.78-3.72 (m, 2H), 3.53-3.47 (m, 2H), 2.94-2.89 (m, 1H), 2.89-2.77 (m, 3H), 1.98-1.76 (m, 3H), 0.53-0.35 (m, 4H).

Example 36

(4-Cyclobutyl-[1,4]diazepan-1-yl)-[6-(3,5-difluorophenoxy)-pyridin-3-yl]-methanone

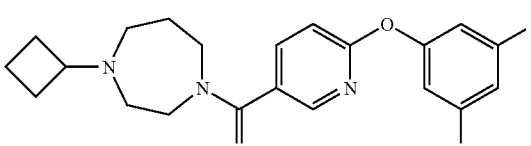

MS (ESI): mass calcd. for $C_{21}H_{23}F_2N_3O_2$, 387.18; m/z found, 388.5 [M+H]$^+$.

Example 37

(4-Cyclopropyl-[1,4]diazepan-1-yl)-[6-(3-fluoro-phenoxy)-pyridin-3-yl]-methanone

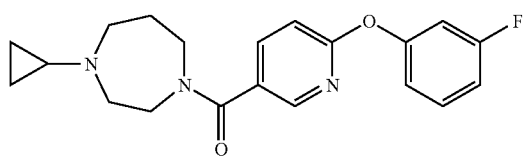 [SMILES: O=C(c1ccc(Oc2cccc(F)c2)nc1)N1CCCN(C2CC2)CC1]

MS (ESI): mass calcd. for C₂₀H₂₂FN₃O₂, 355.17; m/z found, 356.5 [M+H]⁺.

¹H NMR (CDCl₃): 8.30-8.12 (m, 1H), 7.86-7.73 (m, 1H), 7.43-7.33 (m, 1H), 7.03-7.83 (m, 4H), 3.84-3.65 (m, 1H), 3.57-3.36 (m, 3H), 3.00-2.92 (m, 1H), 2.90-2.70 (m, 3H), 2.00-1.66 (m, 3H), 0.54-0.34 (m, 4H).

Example 38

[6-(3-Fluoro-phenoxy)-pyridin-3-yl]-(4-isopropyl-[1,4]diazepan-1-yl)-methanone

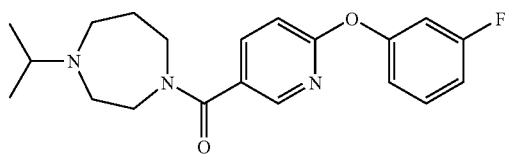 [SMILES: CC(C)N1CCCN(C(=O)c2ccc(Oc3cccc(F)c3)nc2)CC1]

MS (ESI): mass calcd. for C₂₀H₂₄FN₃O₂, 357.19; m/z found, 358.5 [M+H]⁺.

¹H NMR (CDCl₃): 8.32-8.21 (m, 1H), 7.86-7.76 (m, 1H), 7.42-7.32 (m, 1H), 7.03-6.85 (m, 4H), 3.85-3.68 (m, 2H), 3.59-3.40 (m, 2H), 3.08-2.77 (m, 2H), 2.73-2.58 (m, 3H), 2.02-1.86 (m, 2H), 1.15-0.89 (m, 6H).

Example 39

(4-Cyclobutyl-[1,4]diazepan-1-yl)-[6-(3-fluoro-phenoxy)-pyridin-3-yl]-methanone

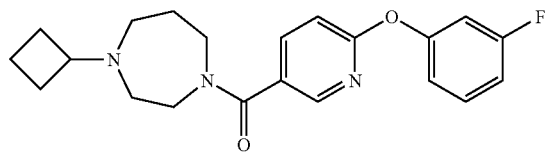 [SMILES: O=C(c1ccc(Oc2cccc(F)c2)nc1)N1CCCN(C2CCC2)CC1]

MS (ESI): mass calcd. for C₂₁H₂₄FN₃O₂, 369.19; m/z found, 370.5 [M+H]⁺.

¹H NMR (CDCl₃): 8.29-8.22 (m, 1H), 7.86-7.77 (m, 1H), 7.42-7.32 (m, 1H), 7.01-6.87 (m, 4H), 3.84-3.72 (m, 2H), 3.59-3.46 (m, 2H), 2.98-2.78 (m, 1H), 2.68-2.58 (m, 1H), 2.55-2.38 (m, 3H), 2.12-1.54 (m, 8H).

Example 40

(4-Cyclobutyl-[1,4]diazepan-1-yl)-[6-(3-methyl-4-methylsulfanyl-phenoxy)-pyridin-3-yl]methanone

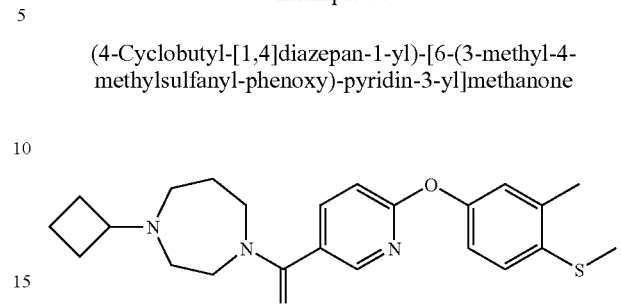

MS (ESI): mass calcd. for C₂₃H₂₉N₃O₂S, 411.12; m/z found, 412.5 [M+H]⁺.

¹H NMR (CDCl₃): 8.31-8.19 (m, 1H), 7.83-7.74 (m, 1H), 7.24-7.17 (m, 1H), 7.03-6.88 (m, 3H), 3.84-3.66 (m, 2H), 3.62-3.45 (m, 2H), 2.99-2.77 (m, 1H), 2.69-2.67 (m, 1H), 2.56-2.38 (m, 6H), 3.52 (5, 3H), 2.13-1.50 (m, 8H).

Example 41

(4-Cyclopropyl-[1,4]diazepan-1-yl)-[6-(3-methyl-4-methylsulfanyl-phenoxy)-pyridin-3-yl]-methanone

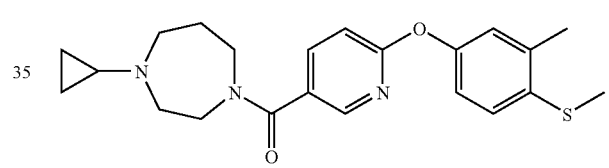

MS (ESI): mass calcd. for C₂₂H₂₇N₃O₂S, 397.18; m/z found, 398.5 [M+H]⁺.

¹H NMR (CDCl₃): 8.30-8.19 (m, 1H), 7.84-7.70 (m, 1H), 7.24-7.18 (m, 1H), 7.05-6.88 (m, 3H), 3.84-3.68 (m, 2H), 3.56-3.46 (m, 2H), 3.01-2.91 (m, 1H), 2.89-2.72 (m, 3H), 2.47 (s, 3H), 2.35 (s, 3H), 1.99-1.71 (m, 3H), 0.56-0.26 (m, 4H).

Example 42

(4-Isopropyl-[1,4]diazepan-1-yl)-[6-(3-methyl-4-methylsulfanyl-phenoxy)-pyridin-3-yl]methanone

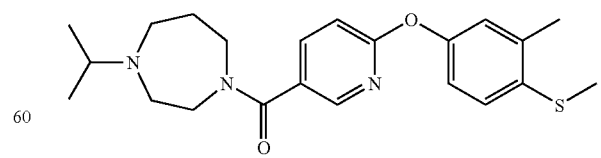

MS (ESI): mass calcd. for C₂₂H₂₉N₃O₂S, 399.20; m/z found, 400.5 [M+H]⁺.

¹H NMR (CDCl₃): 8.29-8.20 (m, 1H), 7.81-7.65 (m, 1H), 7.24-7.18 (m, 1H), 7.02-6.90 (m, 3H), 3.83-3.63 (m, 2H), 3.57-3.43 (m, 2H), 3.06-2.74 (m, 2H), 2.72-2.56 (m, 3H), 2.47 (s, 3H), 3.52 (s, 3H), 1.98-1.87 (m, 1H), 1.84-1.71 (m, 1H), 1.12-0.90 (m, 6H).

Example 43

[6-(3,4-Dichloro-phenoxy)-pyridin-2-yl]-(4-isopropyl-piperazin-1-yl)-methanone

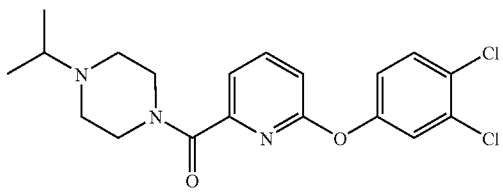 [SMILES: CC(C)N1CCN(C(=O)c2cccc(Oc3ccc(Cl)c(Cl)c3)n2)CC1]

Step A; (6-Bromo-pyridin-2-yl)-(4-isopropyl-piperazin-1-yl)-methanone

To a solution of 6-bromo-pyridine-2-carboxylic acid (100.00 mg, 0.50 mmol) in DCM (5.0 mL) was added 1-isopropylpiperazine (95.20 mg, 0.74 mmol) followed by 1-(3-dimethylaminopropyl)-3-ethylcarbodiimide hydrochloride (EDC; 189.78 mg, 0.99 mmol), 1-hydroxybenzotriazole (HOBt; 133.78 mg, 0.99 mmol), and iPr$_2$NEt (0.86 mL, 4.95 mmol). After 18 h at rt, the mixture was diluted with water and extracted with DCM. Purification by FCC provided the desired product (83.0 mg, 54%). MS (ESI): mass calcd. for $C_{13}H_{18}BrN_3O$, 311.06; m/z found, 312.2 [M+H]$^+$. $^1$H NMR (CDCl$_3$): 7.69-7.59 (m, 2H), 7.56-7.52 (m, 1H), 3.84-3.76 (m, 2H), 2.79-2.68 (m, 1H), 2.62 (t, J=5.1 Hz, 2H), 2.53 (t, J=5.1 Hz, 2H), 1.06 (d, J=6.5 Hz, 6H). Assay 1 (Human H$_3$): K$_i$=1400 nM.

Step B

To a solution of (6-bromo-pyridin-2-yl)-(4-isopropyl-piperazin-1-yl)-methanone (76.7 mg, 0.25 mmol) in DMF (2.5 mL) was added 3,4 dichlorophenol (40.07 mg, 0.25 mmol) and K$_2$CO$_3$ (101.93 mg, 0.74 mmol). After 18 h at 120° C., the mixture was cooled to rt, diluted with water, and extracted with DCM. Purification by FCC followed by reverse phase HPLC (basic conditions) provided the desired product (10.0 mg, 3.5%). MS (ESI): mass calcd. for $C_{19}H_{21}Cl_2N_3O_2$, 393.10; m/z found, 394.3 [M+H]$^+$. $^1$H NMR (CDCl$_3$): 7.82 (dd, J=8.2, 7.4 Hz, 1H), 7.52-7.44 (m, 2H), 7.26 (d, J=2.7 Hz, 1H), 7.06-6.98 (m, 2H), 3.75-3.67 (m, 2H), 3.50-3.44 (m, 2H), 2.70-2.61 (m, 1H), 2.55-2.48 (m, 2H), 2.23-2.15 (m, 2H), 1.01 (d, J=6.6 Hz, 6H).

The compounds in Examples 44-52 were prepared using methods analogous to those described in Example 43. Where trifluoroacetic acid salts were obtained, purification was done using preparative HPLC (acidic conditions).

Example 44

(4-Cyclopropyl-[1,4]diazepan-1-yl)-[6-(3,4-dichloro-phenoxy)-pyridin-2-yl]-methanone

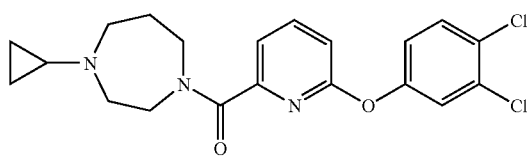 [SMILES: O=C(c1cccc(Oc2ccc(Cl)c(Cl)c2)n1)N1CCCN(C2CC2)CC1]

Step A; (6-Bromo-pyridin-2-yl)-(4-cyclopropyl-[1,4]diazepan-1-yl)-methanone

MS (ESI): mass calcd. for $C_{14}H_{18}BrN_3O$, 323.06; m/z found, 326.3 [M+H]$^+$. $^1$H NMR (CDCl$_3$): 7.67-7.63 (m, 1H), 7.62-7.58 (m, 1H), 7.54-7.51 (m, 1H), 3.80-3.73 (m, 2H), 3.62-3.53 (m, 2H), 3.00-2.95 (m, 1H), 2.92-2.81 (m, 3H), 1.99-1.81 (m, 3H), 0.54-0.35 (m, 4H). Assay 1 (Human H$_3$): K$_i$=431 nM.

Step B

MS (ESI): mass calcd. for $C_{20}H_{21}Cl_2N_3O_2$, 405.10; m/z found, 406.4 [M+H]$^+$. $^1$H NMR (CDCl$_3$): 7.85-7.78 (m, 1H), 7.49-7.40 (m, 2H), 7.29-7.24 (m, 1H), 7.04-6.97 (m, 2H), 3.71-3.64 (m, 2H), 3.43-3.35 (m, 2H), 2.91-2.85 (m, 1H), 2.75-2.69 (m, 1H), 2.64-2.59 (m, 1H), 2.44-2.38 (m, 1H), 1.93-1.85 (m, 1H), 1.64-1.50 (m, 2H), 0.51-0.28 (m, 4H).

Example 45

(4-Cyclobutyl-[1,4]diazepan-1-yl)-[6-(3,4-dichloro-phenoxy)-pyridin-2-yl]-methanone

Step A; (6-Bromo-pyridin-2-yl)-(4-cyclobutyl-[1,4]diazepan-1-yl)-methanone

MS (ESI): mass calcd. for $C_{15}H_{20}BrN_3O$, 337.08; m/z found, 339.2 [M+H]$^+$. $^1$H NMR (CDCl$_3$): 7.67-7.58 (m, 2H), 7.54-7.50 (m, 1H), 3.85-3.74 (m, 2H), 3.69-3.52 (m, 2H), 3.01-2.86 (m, 1H), 2.69-2.44 (m, 4H), 2.14-1.53 (m, 8H). Assay 1 (Human H$_3$): K$_i$=33 nM.

Step B

MS (ESI): mass calcd. for $C_{21}H_{23}Cl_2N_3O_2$, 419.12; m/z found, 420.4 [M+H]$^+$. $^1$H NMR (CDCl$_3$): 7.86-7.78 (m, 1H), 7.50-7.39 (m, 2H), 7.28-7.23 (m, 1H), 7.04-6.97 (m, 2H), 3.73-3.66 (m, 2H), 3.48-3.42 (m, 1H), 3.39 (t, J=6.5 Hz, 1H), 2.91-2.58 (m, 1H), 2.57-2.51 (m, 1H), 2.91-2.58 (M, 1H), 2.23-2.20 (m, 1H), 2.14-1.87 (m, 4H), 1.86-1.48 (m, 5H).

Example 46

[6-(3,4-Dichloro-phenoxy)-pyridin-2-yl]-(4-isopropyl-[1,4]diazepan-1-yl)-methanone

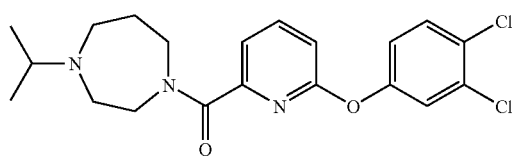

Step A; (6-Bromo-pyridin-2-yl)-(4-isopropyl-[1,4]diazepan-1-yl)-methanone

MS (ESI): mass calcd. for $C_{14}H_{20}BrN_3O$, 325.08; m/z found, 328.3 [M+H]$^+$. $^1$H NMR (CDCl$_3$): 7.68-7.58 (m, 2H), 7.54-7.50 (m, 1H), 3.82-3.72 (m, 2H), 3.63-3.53 (m, 2H), 3.01-2.87 (m, 1H), 2.84-2.76 (m, 1H), 2.77-2.61 (m, 3H), 2.02-1.78 (m, 2H), 1.08-0.95 (m, 6H). Assay 1 (Human H$_3$): K$_i$=752 nM.

Step B

MS (ESI): mass calcd. for $C_{20}H_{23}Cl_2N_3O_2$, 407.12; m/z found, 408.4 [M+H]$^+$. $^1$H NMR (CDCl$_3$): 7.86-7.79 (m, 1H), 7.51-7.40 (m, 2H), 7.25 (d, J=2.7, 1H), 7.03-6.96 (m, 2H), 3.73-3.67 (m, 2H), 3.65-3.57 (m, 2H), 3.47-3.43 (m, 1H), 3.41-3.35 (m, 1H), 2.99-2.67 (m, 2H) 2.62-2.54 (m, 1H), 2.45-2.32 (m, 2H), 1.98-1.41 (m, 2H), 1.00-0.92 (m, 6H).

Example 47

[6-(4-Chloro-3-methyl-phenoxy)-pyridin-2-yl]-(4-cyclopropyl-[1,4]diazepan-1-yl)-methanone trifluoroacetic acid salt

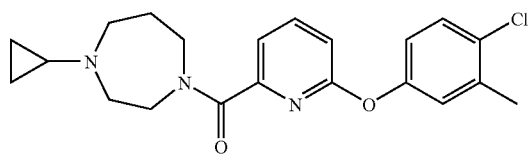 [SMILES: Cc1cc(Oc2cccc(C(=O)N3CCCN(C4CC4)CC3)n2)ccc1Cl]

MS (ESI): mass calcd. for $C_{21}H_{24}ClN_3O_2$, 385.16; m/z found, 386.5 [M+H]$^+$.

$^1$H NMR (MeOD): 8.04-7.94 (m, 1H), 7.62-7.39 (m, 2H), 7.25-7.10 (m, 2H), 7.08-6.96 (m, 1H), 4.42-3.08 (m, 7H), 3.03-2.96 (m, 1H), 2.92-2.82 (m, 0.5H), 2.59-2.50 (m, 0.5H), 2.44-2.35 (m, 3H), 2.28-2.04 (m, 1H), 1.95-1.35 (m, 1H), 1.09-0.86 (m, 4H).

Example 48

[6-(4-Chloro-3-methyl-phenoxy)-pyridin-2-yl]-(4-cyclobutyl-[1,4]diazepan-1-yl)-methanone trifluoroacetic acid salt

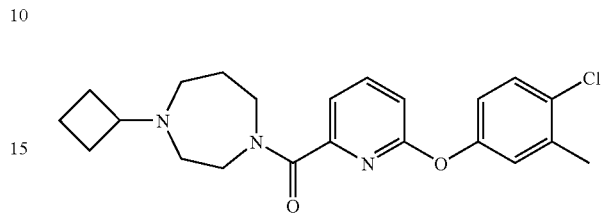

MS (ESI): mass calcd. for $C_{22}H_{26}ClN_3O_2$, 399.17; m/z found, 400.5 [M+H]$^+$.

$^1$H NMR (MeOD): 8.09-7.90 (m, 1H), 7.63-7.37 (m, 2H), 7.26-7.10 (m, 2H), 7.08-6.94 (m, 1H), 4.32-3.24 (m, 7H), 3.19-2.50 (m, 3H), 2.50-1.20 (m, 7H), 1.98-1.67 (m, 3H).

Example 49

[6-(4-Chloro-3-methyl-phenoxy)-pyridin-2-yl]-(4-isopropyl-[1,4]diazepan-1-yl)-methanone trifluoroacetic acid salt

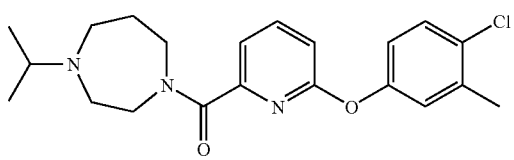 [SMILES: Cc1cc(Oc2cccc(C(=O)N3CCCN(C(C)C)CC3)n2)ccc1Cl]

MS (ESI): mass calcd. for $C_{21}H_{26}ClN_3O_2$, 387.17; m/z found, 388.5 [M+H]$^+$.

$^1$H NMR (MeOD): 8.08-7.93 (m, 1H), 7.50-7.38 (m, 2H), 7.29-7.09 (m, 2H), 7.07-6.96 (m, 1H), 4.18-3.86 (m, 1H), 3.86-3.40 (m, 4H), 3.41-2.82 (m, 4H), 2.44-2.35 (m, 3H), 2.33-1.97 (m, 1H), 1.93-1.76 (m, 1H), 1.39-1.08 (m, 6H).

Example 50

[5-(3,4-Dichloro-phenoxy)-pyridin-2-yl]-(4-isopropyl-[1,4]diazepan-1-yl)-methanone trifluoroacetic acid salt

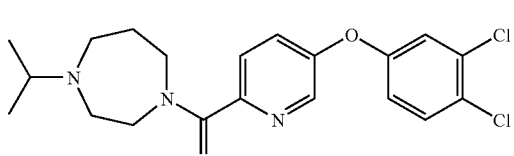

Step A; (5-Bromo-pyridin-2-yl)-(4-isopropyl-[1,4]diazepan-1-yl)-methanone

MS (ESI): mass calcd. for $C_{14}H_{20}BrN_3O$, 326.08; m/z found, 328.4 [M+H]$^+$. $^1$H NMR (CDCl$_3$): 8.64 (dd, J=2.4, 0.8

Hz, 1H), 7.93-7.89 (m, 1H), 7.56-7.52 (m, 1H), 3.81-7.75 (m, 2H), 3.60-3.53 (m, 2H), 3.00-2.85 (m, 1H), 2.83-2.77 (m, 1H), 2.72-2.60 (m, 3H), 1.97-1.90 (m, 1H), 1.84-1.72 (m, 1H), 1.05-0.96 (m, 6H). Assay 1 (Human H$_3$): K$_i$=194 nM.

Step B

MS (ESI): mass calcd. for C$_{20}$H$_{23}$Cl$_2$N$_3$O$_2$, 407.12; m/z found, 408.4 [M+H]$^+$. $^1$H NMR (MeOD): 8.45-8.34 (m, 1H), 7.87-7.71 (m, 1H), 7.62-7.55 (m, 2H), 7.38-7.32 (m, 1H), 7.14-7.05 (m, 1H), 4.23-3.50 (m, 7H), 3.45-3.27 (m, 2H), 2.39-2.10 (m, 2H), 1.44-1.34 (m, 6H).

Example 51

(4-Cyclobutyl-[1,4]diazepan-1-yl)-[5-(3,4-dichloro-phenoxy)-pyridin-2-yl]-methanone trifluoroacetic acid salt

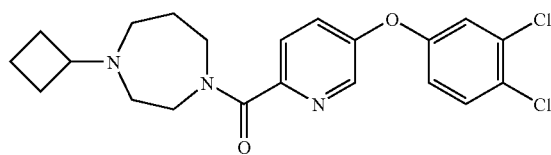 [SMILES: O=C(c1ccc(Oc2ccc(Cl)c(Cl)c2)cn1)N1CCCN(C2CCC2)CC1]

Step A; (5-Bromo-pyridin-2-yl)-(4-cyclobutyl-[1,4]diazepan-1-yl)-methanone

MS (ESI): mass calcd. for C$_{15}$H$_{20}$BrN$_3$O, 337.08; m/z found, 340.4 [M+H]$^+$. $^1$H NMR (CDCl$_3$): 8.66-8.61 (m, 1H), 7.95-7.89 (m, 1H), 7.58-7.52 (m, 1H), 3.82-3.76 (m, 2H), 3.65-3.55 (m, 2H), 2.98-2.82 (m, 1H), 2.67-2.60 (m, 1H), 2.56-2.44 (m, 3H), 2.12-1.55 (m, 8H). Assay 1 (Human H$_3$): K$_i$=11 nM.

Step B

MS (ESI): mass calcd. for C$_{21}$H$_{23}$Cl$_2$N$_3$O$_2$, 419.12; m/z found, 420.4 [M+H]$^+$. $^1$H NMR (MeOD): 8.49-8.31 (m, 1H), 7.92-7.72 (m, 1H), 7.70-7.53 (m, 2H), 7.77-7.28 (m, 1H), 7.21-7.04 (m, 1H), 4.37-4.02 (m, 1H), 3.97-3.02 (m, 8H), 2.52-2.06 (m, 6H), 2.01-1.71 (m, 2H).

Example 52

(4-Cyclopropyl-[1,4]diazepan-1-yl)-[5-(3,4-dichloro-phenoxy)-pyridin-2-yl]-methanone trifluoroacetic acid salt

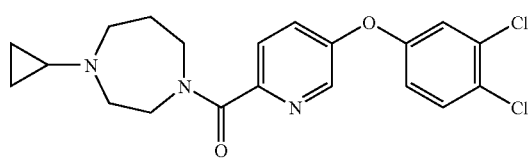 [SMILES: O=C(c1ccc(Oc2ccc(Cl)c(Cl)c2)cn1)N1CCCN(C2CC2)CC1]

Step A; (5-Bromo-pyridin-2-yl)-(4-cyclopropyl-[1,4]diazepan-1-yl)-methanone

MS (ESI): mass calcd. for C$_{14}$H$_{18}$BrN$_3$O, 323.06; m/z found, 324.4 [M+H]$^+$. $^1$H NMR (CDCl$_3$): 8.66-8.62 (m, 1H), 7.95-7.89 (m, 1H), 7.58-7.51 (m, 1H), 3.82-3.73 (m, 2H), 3.63-3.52 (m, 2H), 3.01-2.94 (m, 1H), 2.90-2.78 (m 3H), 2.01-1.78 (m, 3H), 0.54-0.34 (m, 4H). Assay 1 (Human H$_3$): K$_i$=115 nM.

Step B

MS (ESI): mass calcd. for C$_{20}$H$_{21}$Cl$_2$N$_3$O$_2$, 405.10; m/z found, 406.4 [M+H]$^+$. $^1$H NMR (MeOD): 8.43-8.32 (m, 1H), 7.87-7.72 (m, 1H), 7.64-7.42 (m, 2H), 7.40-7.29 (m, 1H), 7.14-7.01 (m, 1H), 4.08-3.43 (m, 8H), 3.08-2.93 (m, 1H), 2.48-2.09 (m, 2H), 1.12-0.94 (m, 4H).

Example 53

3-(3,4-Dichloro-phenoxy)-6-(4-isopropyl-piperazine-1-carbonyl)-pyridine-2-carbonitrile trifluoroacetic acid salt

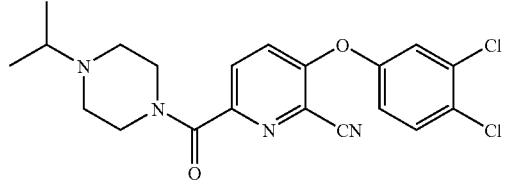 [SMILES: CC(C)N1CCN(C(=O)c2ccc(Oc3ccc(Cl)c(Cl)c3)c(C#N)n2)CC1]

Step A; 5-Bromo-pyridine-2-carboxylic acid methyl ester

A mixture of 5-bromo-2-pyridine carboxylic acid (26.2 g, 0.124 mol) and conc. H$_2$SO$_4$ (12.5 mL) in MeOH (250 mL) was heated to 60° C. and diluted with additional MeOH (250 mL). After 18 h at 60° C., the mixture was cooled to rt, diluted with DCM, and washed with a solution consisting of 21 g KOH in 200 mL water, sat. K$_2$CO$_3$, and water. The organic layer was dried and concentrated to give the title compound (21.4 g, 76%) as a white solid. This material was used in the next step without further purification.

Step B; 5-Bromo-1-oxo-pyridine-2-carboxylic acid methyl ester

To a 0° C. mixture of 5-bromo-pyridine-2-carboxylic acid methyl ester (10.1 g, 46.8 mmol) and urea hydrogen peroxide complex (9.33 g, 99.2 mmol) in acetonitrile (150 mL) was added trifluoroacetic anhydride (13.0 mL, 93.7 mmol). After 2 h, the mixture was poured into 0.5 M HCl and extracted with DCM. The organic layer was washed with satd. aq. NaHCO$_3$, dried, and concentrated. The residue was purified by FCC (ethyl acetate (EtOAc)/hexanes) to give the title compound (9.70 g, 89%) as a colorless viscous oil. MS (ESI): mass calcd. for C$_7$H$_6$BrNO$_3$, 230.95; m/z found, 232.2 [M+H]$^+$. $^1$H NMR (d$^6$-acetone): 8.49-8.48 (m, 1H), 7.63-7.62 (m, 2H), 3.89 (s, 3H).

Step C; 5-Bromo-6-cyano-pyridine-2-carboxylic acid methyl ester

A mixture of 5-bromo-1-oxo-pyridine-2-carboxylic acid methyl ester (9.43 g, 40.6 mmol), TMSCN (54 mL), and dimethylcarbamyl chloride (38 mL) was heated at 50° C. for 16 h. The mixture was allowed to cool to rt and was poured over ice water containing NaOH (40 g, 1 mol). The mixture was extracted with DCM (2×), and the combined organic layers were dried and concentrated to give the crude product as a red solid. Recrystallization from hot MeOH and FCC (EtOAc/hexanes) of the concentrated mother liquor together gave the title compound (7.51 g, 77%). $^1$H NMR (d$^6$-acetone): 8.83 (d, J=8.4 Hz, 1H), 8.27 (d, J=8.4 Hz, 1H), 3.96 (s, 3H).

Step D; 5-Bromo-6-cyano-pyridine-2-carboxylic acid

To a solution of potassium trimethylsilanoate (0.80 g, 6.22 mmol) in THF (26 mL) was added 5-bromo-6-cyano-pyridine-2-carboxylic acid methyl ester (998 mg, 4.15 mmol). The mixture was heated at 50° C. for 3 h, then was cooled to rt and treated with HCl (4 N in dioxane; 1.60 mL). After 30 min, the mixture was concentrated. The residue was dissolved in hot EtOAc and filtered. The filtrate was concentrated to give the title compound (993 mg, >100%), which was used in the next step without further purification.

Step E; 3-Bromo-6-(4-isopropyl-piperazine-1-carbonyl)-pyridine-2-carbonitrile A mixture of 5-bromo-6-cyano-pyridine-2-carboxylic acid (875 mg, 3.85 mmol), HOBt (882 mg, 6.53 mmol), and EDC (1.11 g, 5.80 mmol) in DMF (32 mL) was stirred for 5 min and then treated with 1-isopropyl-piperazine (943 mg, 7.35 mmol). After 5 h, the mixture was diluted with DCM, washed with 1 N NaOH and water, dried, and concentrated. Purification of the residue by FCC gave a viscous foam that crystallized upon standing. Further purification by reverse-phase HPLC gave the title compound (476 mg, 37%). MS (ESI): mass calcd. for $C_{14}H_{17}BrN_4O$, 336.06; m/z found, 337.2 [M+H]$^+$. $^1$H NMR (d$^6$-acetone): 8.43 (d, J=8.4 Hz, 1H), 7.83 (d, J=8.4 Hz, 1H), 3.70-3.68 (m, 2H), 3.51-3.49 (m, 2H), 2.73 (septet, J=6.6 Hz, 1H), 2.58-2.56 (m, 2H), 2.50-2.48 (m, 2H), 1.01 (d, J=6.6 Hz, 6H).

Step F

A mixture of 3-bromo-6-(4-isopropyl-piperazine-1-carbonyl)-pyridine-2-carbonitrile (54.4 mg), 3,4-dichlorophenol (76.8 mg), and anhydrous $Cs_2CO_3$ (350 mg) in DMSO (0.6 mL) was heated by microwave irradiation at 150° C. for 30 min. The mixture was purified by HPLC to give the title compound (18.5 mg, 31%) as the TFA salt. MS (ESI): mass calcd. for $C_{20}H_{20}Cl_2N_4O_2$, 418.10; m/z found, 419.2 [M+H]$^+$. $^1$H NMR (MeOD): 8.00 (d, J=9.0 Hz, 1H), 7.67 (d, J=8.4 Hz, 1H), 7.63 (d, J=9.0 Hz, 1H), 7.51 (d, J=3.0 Hz, 1H), 7.23-7.21 (dd, J=8.7, 2.4 Hz, 1H), 4.87-4.80 (br s, 1H), 4.59-4.48 (br s, 1H), 3.70-3.46 (m, 4H), 3.35-3.18 (br s, 3H), 1.41 (d, J=7.2 Hz, 6H).

Example 54

3-(3,4-Dichloro-phenoxy)-6-(4-isopropyl-piperazine-1-carbonyl)-pyridine-2-carboxylic acid amide trifluoroacetic acid salt

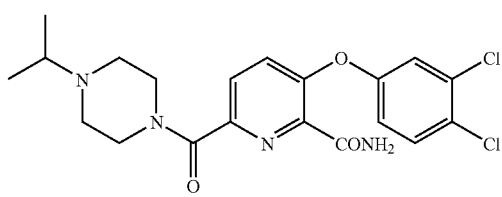 [SMILES: CC(C)N1CCN(C(=O)c2ccc(Oc3ccc(Cl)c(Cl)c3)c(C(N)=O)n2)CC1]

The title compound was obtained from Example 53 using methods similar to those described in Example 62 (9.8 mg, 16%). MS (ESI): mass calcd. for $C_{20}H_{22}Cl_2N_4O_3$, 436.11; m/z found, 437.3 [M+H]$^+$. $^1$H NMR (MeOD): 7.97 (d, J=9.0 Hz, 1H), 7.70 (d, J=9.0 Hz, 1H), 7.58 (d, J=8.4 Hz, 1H), 7.31 (d, J=3.0 Hz, 1H), 7.06-7.04 (dd, J=8.7, 3.0 Hz, 1H), 4.6 (br s, 1H), 3.90 (s, 2H), 3.69-3.55 (m, 3H), 3.55-3.46 (br s, 1H), 3.42-3.20 (br m, 3H), 1.41 (d, J=7.2 Hz, 6H).

Example 55

6-(4-Cyclopropyl-[1,4]diazepane-1-carbonyl)-3-(4-methylsulfanyl-phenoxy)-pyridine-2-carbonitrile

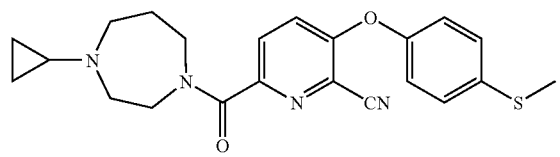 [SMILES: CSc1ccc(Oc2ccc(C(=O)N3CCCN(C4CC4)CC3)nc2C#N)cc1]

Step A; 5-Bromo-1-oxo-pyridine-2-carboxylic acid

To a 0° C. mixture of 5-bromo-picolinic acid (18.5 g, 91.6 mmol) and urea hydrogen peroxide complex (18.2 g, 0.194 mol) in acetonitrile (275 mL) was added trifluoroacetic anhydride (26 mL, 0.187 mol). After 4.5 h, the mixture was treated with aq. $Na_2S_2O_3$ at 0° C., stirred for 10 min, and then extracted with DCM (300 mL×5). The combined organic layers were concentrated to give the crude product, which was suspended in boiling water (500 mL) and filtered. The filtered solid was triturated with boiling MeOH (500 mL) twice, leaving a yellow solid. The aqueous and methanolic extracts were combined and concentrated to dryness to give >100% of the acid as a tan solid. MS (ESI): mass calcd. for $C_6H_4BrNO_3$, 216.94; m/z found, 218.1 [M+H]$^+$. $^1$H NMR (d$^6$-DMSO): 17.70 (s, 1H), 9.19 (d, J=1.5 Hz, 1H), 8.18-8.12 (m, 2H).

Step B; (5-Bromo-1-oxo-pyridin-2-yl)-(4-cyclopropyl-[1,4]diazepan-1-yl)-methanone A mixture of 5-bromo-1-oxo-pyridine-2-carboxylic acid (1.12 g, 5.15 mmol), HOBt (1.17 g, 8.69 mmol), and EDC (1.56 g, 8.14 mmol) in DMF (32 mL) was stirred for 5 min and then treated with 1-cyclopropyl-[1,4]diazepane dihydrochloride (1.38 g, 6.48 mmol) and 1,8-diazabicyclo[5.4.0]undec-7-ene (DBU; 2.3 mL, 15.4 mmol). After 22 h, the mixture was diluted with DCM and washed with 1 N NaOH and water. The organic layer was dried and concentrated. The residue was purified by FCC to give the title compound (1.13 g, 65%). MS (ESI): mass calcd. for $C_{14}H_{18}BrN_3O_2$, 339.06; m/z found, 340.2 [M+H]$^+$.

Step C; 3-Bromo-6-(4-cyclopropyl-[1,4]diazepane-1-carbonyl)-pyridine-2-carbonitrile The title compound (76%) was prepared using methods analogous to those described for Example 53, Step C. MS (ESI): mass calcd. for $C_{15}H_{17}BrN_4O$, 348.0586; m/z found, 349.6 [M+H]$^+$. $^1$H NMR (d$^6$-acetone): 8.42 (d, J=8.4 Hz, 1H), 7.83-7.81 (m, 1H), 3.70-3.68 (m, 2H), 3.55-3.52 (m, 2H), 2.93-2.91 (m, 1H), 2.87-2.80 (m, 3H), 1.96-1.87 (m, 2H), 1.84-1.80 (m, 1H), 0.46-0.44 (m, 1H), 0.43-0.41 (m, 1H), 0.37-0.35 (m, 1H), 0.32-0.30 (m, 1H).

Step D

The title compound (71%) was prepared using methods analogous to those described for Example 53, Step F, with purification by FCC. MS (ESI): mass calcd. for $C_{22}H_{24}N_4O_2S$, 408.16; m/z found, 409.7 [M+H]$^+$. $^1$H NMR (d$^6$-acetone): 7.87-7.85 (dd, J=8.7, 3.6 Hz, 1H), 7.51 (d, J=9.0 Hz, 1H), 7.43 (d, J=8.4 Hz, 2H), 7.26 (d, J=9.0 Hz, 2H), 3.70-3.68 (m, 2H), 3.61-3.58 (m, 2H), 3.40-3.37 (m, 3H), 2.92-2.88 (m, 2H), 2.85-2.81 (m, 2H), 2.77-2.70 (m, 3H), 2.54 (s, 3H), 1.96-1.83 (m, 4H), 1.75-1.71 (m, 1H), 0.46-0.44 (m, 1H), 0.43-0.40 (m, 1H), 0.37-0.35 (m, 1H), 0.33-0.30 (m, 2H).

The compounds in Examples 56-61 were prepared using methods analogous to those described for Example 55, with exceptions where noted.

Example 56

6-(4-Cyclopropyl-[1,4]diazepane-1-carbonyl)-3-(pyridin-3-yloxy)-pyridine-2-carbonitrile hydrochloride salt

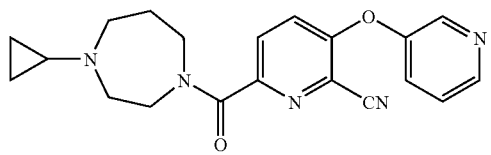 [SMILES: N#Cc1nc(C(=O)N2CCCN(C3CC3)CC2)ccc1Oc1cccnc1]

MS (ESI): mass calcd. for $C_{20}H_{21}N_5O_2$, 363.18; m/z found, 364.7 [M+H]$^+$.

$^1$H NMR (d$^6$-acetone): 8.62 (d, J=2.5 Hz, 1H), 8.56-8.55 (dd, J=4.8, 1.5 Hz, 1H), 7.90-7.88 (dd, J=8.8, 3.5 Hz, 1H), 7.78-7.75 (m, 1H), 7.63 (d, J=9.0 Hz, 1H), 7.56-7.54 (dd, J=8.5, 5.0 Hz, 1H), 3.70 (m, 2H), 3.62-3.58 (m, 2H), 2.93-2.88 (m, 2H), 2.85-2.81 (m, 2H), 1.96-1.83 (m, 3H), 0.47-0.41 (m, 2H), 0.38-0.35 (m, 1H), 0.33-0.31 (m, 1H). The free base was dissolved in excess HCl (1.25 M in MeOH) and concentrated to give the hydrochloride salt.

Example 57

3-(4-Chloro-3-methyl-phenoxy)-6-(4-cyclopropyl-[1,4]diazepane-1-carbonyl)-pyridine-2-carbonitrile

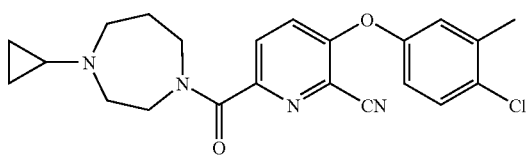 [SMILES: Cc1cc(Oc2ccc(C(=O)N3CCCN(C4CC4)CC3)nc2C#N)ccc1Cl]

MS (ESI): mass calcd. for $C_{22}H_{23}ClN_4O_2$, 410.15; m/z found, 411.1 [M+H]$^+$.

$^1$H NMR (CDCl$_3$): 7.86 (d, J=8.8 Hz, 1H), 7.41 (d, J=8.6 Hz, 1H), 7.27 (d, J=9.9 Hz, 1H), 7.00 (d, J=2.4 Hz, 1H), 6.90 (dd, J=8.5, 2.6 Hz, 1H), 3.78-3.74 (m, 2H), 3.70-3.64 (m, 2H), 2.98-2.94 (m, 2H), 2.88-2.83 (m, 2H), 2.39 (s, 3H), 1.98-1.86 (m, 3H), 0.52-0.36 (m, 4H).

Example 58

6-(4-Cyclopropyl-[1,4]diazepane-1-carbonyl)-3-(3,4-dichloro-phenoxy)-pyridine-2-carbonitrile

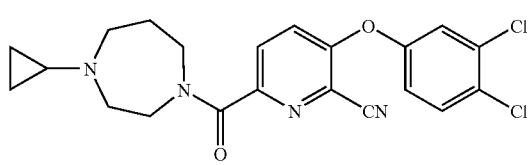 [SMILES: N#Cc1nc(C(=O)N2CCCN(C3CC3)CC2)ccc1Oc1ccc(Cl)c(Cl)c1]

MS (ESI): mass calcd. for $C_{21}H_{20}Cl_2N_4O_2$, 431.31; m/z found, 432.9 [M+H]$^+$. $^1$H NMR (CDCl$_3$): 7.92-7.89 (m, 1H), 7.54 (dd, J=8.7, 0.6 Hz, 1H), 7.34 (dd, J=8.8, 1.1 Hz, 1H), 7.27-7.25 (m, 1H), 7.00 (ddd, J=8.8, 2.8, 0.9 Hz, 1H), 3.79-3.75 (m, 2H), 3.70-3.64 (m, 2H), 2.99-2.94 (m, 2H), 2.89-2.83 (m, 2H), 1.98-1.85 (m, 3H), 0.52-0.37 (m, 4H).

Example 59

6-(4-Cyclopropyl-[1,4]diazepane-1-carbonyl)-3-(4-fluoro-phenoxy)-pyridine-2-carbonitrile

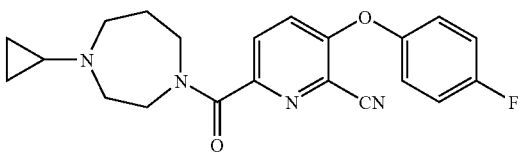 [SMILES: N#Cc1nc(C(=O)N2CCCN(C3CC3)CC2)ccc1Oc1ccc(F)cc1]

MS (ESI): mass calcd. for $C_{21}H_{21}FN_4O_2$, 380.42; m/z found, 381.5 [M+H]$^+$.

$^1$H NMR (CDCl$_3$): 7.84 (d, J=8.9 Hz, 1H), 7.22 (dd, J=8.8, 0.4 Hz, 1H), 7.17-7.07 (m, 4H), 3.79-3.70 (m, 2H), 3.68-3.63 (m, 2H), 2.97-2.91 (m, 2H), 2.87-2.81 (m, 2H), 1.97-1.83 (m, 3H), 0.50-0.34 (m, 4H).

Example 60

6-(4-Cyclopropyl-[1,4]diazepane-1-carbonyl)-3-(3-fluoro-phenoxy)-pyridine-2-carbonitrile

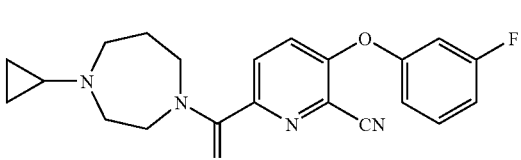

MS (ESI): mass calcd. for $C_{21}H_{21}FN_4O_2$, 380.42; m/z found, 381.5 [M+H]$^+$.

$^1$H NMR (CDCl$_3$): 7.88 (d, J=8.8 Hz, 1H), 7.42 (dd, J=14.7, 8.2 Hz, 1H), 7.33 (dd, J=8.9, 0.8 Hz, 1H), 7.05-6.95

(m, 1H), 6.92-6.83 (m, 2H), 3.78-3.73 (m, 2H), 3.69-3.63 (m, 2H), 2.98-2.93 (m, 2H), 2.88-2.82 (m, 2H), 1.97-1.85 (m, 3H), 0.51-0.35 (m, 4H).

Example 61

6-(4-Cyclopropyl-[1,4]diazepane-1-carbonyl)-3-(2-fluoro-phenoxy)-pyridine-2-carbonitrile

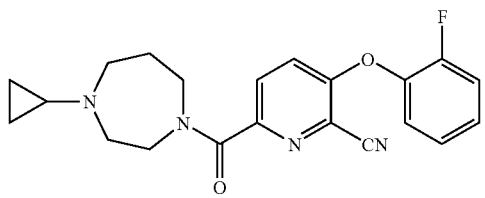 [SMILES: N#Cc1nc(C(=O)N2CCCN(C3CC3)CC2)ccc1Oc1ccccc1F]

MS (ESI): mass calcd. for $C_{21}H_{21}FN_4O_2$, 380.42; m/z found, 381.5 [M+H]$^+$.
$^1$H NMR (CDCl$_3$): 7.84 (d, J=8.8 Hz, 1H), 7.32-7.27 (m, 1H), 7.27-7.21 (m, 3H), 7.17 (dd, J=8.8, 1.1 Hz, 1H), 3.76-3.70 (m, 2H), 3.68-3.62 (m, 2H), 2.96-2.92 (m, 2H), 2.86-2.81 (m, 2H), 1.95-1.84 (m, 3H), 0.49-0.34 (m, 4H).

Example 62

6-(4-Cyclopropyl-[1,4]diazepane-1-carbonyl)-3-(4-methylsulfanyl-phenoxy)-pyridine-2-carboxylic acid amide

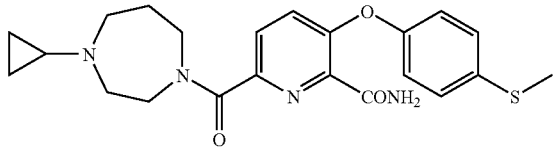 [SMILES: CSc1ccc(Oc2ccc(C(=O)N3CCCN(C4CC4)CC3)nc2C(N)=O)cc1]

A mixture of 6-(4-cyclopropyl-[1,4]diazepane-1-carbonyl)-3-(4-methylsulfanyl-phenoxy)-pyridine-2-carbonitrile (171.0 mg), 28% aq. NH$_3$ (5 mL), and 30% aq. H$_2$O$_2$ (1.0 mL) in MeOH (4.0 mL) was stirred for 1.5 h. The mixture was diluted with DCM and washed with satd. aq. Na$_2$S$_2$O$_3$. The organic layer was dried and concentrated. The residue was purified by reverse-phase HPLC followed by FCC to give the title compound (46.4 mg, 26%). MS (ESI): mass calcd. for $C_{22}H_{26}N_4O_3S$, 426.17; m/z found, 427.8 [M+H]$^+$. $^1$H NMR (d$^6$-acetone): 7.74-7.72 (dd, J=8.5, 2.5 Hz, 1H), 7.55 (br s, 1H), 7.51-7.49 (dd, J=8.5, 1.5 Hz, 1H), 7.33 (d, J=8.5 Hz, 2H), 7.03 (d, J=8.5 Hz, 2H), 6.82 (br s, 1H), 3.71-3.68 (m, 2H), 3.65-3.61 (m, 2H), 2.93-2.88 (m, 2H), 2.85-2.80 (m, 2H), 2.49 (s, 3H), 1.96-1.80 (m, 3H), 0.46-0.44 (m, 1H), 0.42-0.40 (m, 1H), 0.37-0.36 (m, 1H), 0.32-0.30 (m, 1H).

Example 63

6-(4-Cyclopropyl-[1,4]diazepane-1-carbonyl)-3-(pyridin-3-yloxy)-pyridine-2-carboxylic acid amide

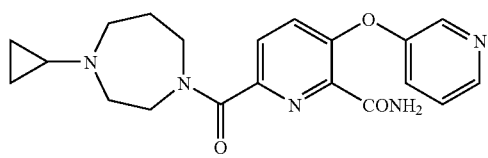 [SMILES: NC(=O)c1nc(C(=O)N2CCCN(C3CC3)CC2)ccc1Oc1cccnc1]

The title compound (67%) was prepared using methods analogous to those described for Example 62. MS (ESI): mass calcd. for $C_{20}H_{23}N_5O_3$, 381.18; m/z found, 382.7 [M+H]$^+$.
$^1$H NMR (d$^6$-acetone): 8.37 (d, J=2.4 Hz, 1H), 8.35-8.34 (dd, J=4.0, 1.6 Hz, 1H), 7.81-7.78 (dd, J=8.8, 2.8 Hz, 1H), 7.69-7.67 (m, 1H), 7.61 (br s, 1H), 7.41-7.35 (m, 2H), 6.83 (br s, 1H), 3.72-3.69 (m, 2H), 3.65-3.60 (m, 2H), 2.94-2.80 (m, 5H), 1.96-1.82 (m, 3H), 0.48-0.44 (m, 1H), 0.42-0.40 (m, 1H), 0.38-0.34 (m, 1H), 0.33-0.29 (m, 1H).

Example 64

[6-Aminomethyl-5-(3,4-dichloro-phenoxy)-pyridin-2-yl]-(4-isopropyl-piperazin-1-yl)-methanone trifluoroacetic acid salt

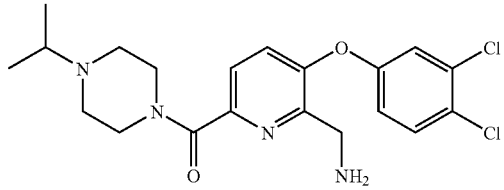 [SMILES: CC(C)N1CCN(C(=O)c2ccc(Oc3ccc(Cl)c(Cl)c3)c(CN)n2)CC1]

A mixture of 3-(3,4-dichloro-phenoxy)-6-(4-isopropyl-piperazine-1-carbonyl)-pyridine-2-carbonitrile (20.0 mg, 0.038 mmol) and CoCl$_2$.6H$_2$O (29.7 mg, 0.125 mmol) in THF/water (2:1; 0.6 mL) was stirred for 5 min and then treated with NaBH$_4$ (34.3 mg, 0.907 mmol). After 6 h, the mixture was diluted with DCM, washed with 1 N NaOH, dried over Na$_2$CO$_3$, and concentrated. Reverse-phase HPLC gave the desired product as the TFA salt (4.7 mg, 19%). MS (ESI): mass calcd. for $C_{20}H_{24}Cl_2N_4O_2$, 422.13; m/z found, 423.3 [M+H]$^+$. $^1$H NMR (MeOD): 7.78 (d, J=8.4 Hz, 1H), 7.64 (d, J=9.0 Hz, 1H), 7.47 (d, J=9.0 Hz, 1H), 7.42 (d, J=3.0 Hz, 1H), 7.16-7.14 (dd, J=8.7, 2.4 Hz, 1H), 4.47 (s, 2H), 3.74-3.60 (m, 4H), 3.52-3.38 (br s, 2H), 3.36-3.10 (br s, 3H), 1.41 (d, J=6.6 Hz, 6H).

The compounds in Examples 65-83 were prepared using methods analogous to those described in the preceding examples, except where otherwise noted.

Example 65

(4-Cyclopentyl-[1,4]diazepan-1-yl)-(6-phenoxy-pyridin-3-yl)-methanone

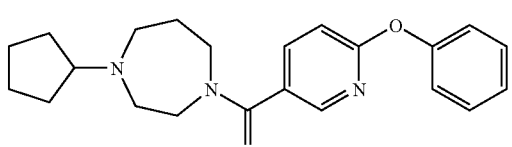

MS (ESI): mass calcd. for $C_{22}H_{27}N_3O_2$, 365.21; m/z found 366.5 [M+H]$^+$. $^1$H NMR (CDCl$_3$): 8.33-7.25 (m, 1H), 7.85-7.78 (m, 1H), 7.48-7.42 (m, 2H), 7.30-6.24 (m, 1H), 7.20-7.13 (m, 2H) 6.96 (d, J=8.5 Hz, 1H), 3.94-3.72 (m, 2H), 3.65-3.50 (m, 2H), 3.50-3.10 (m, 5H), 2.15-1.20 (m, 10H).

Example 66

(4-Cyclopentyl-[1,4]diazepan-1-yl)-[6-(3,4-dichloro-phenoxy)-pyridin-3-yl]methanone

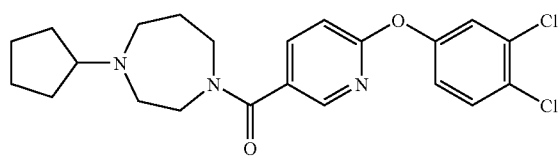 [SMILES: O=C(c1ccc(Oc2ccc(Cl)c(Cl)c2)nc1)N1CCCN(C2CCCC2)CC1]

MS (ESI): mass calcd. for $C_{22}H_{25}Cl_2N_3O_2$, 433.13; m/z found, 434.5 [M+H]$^+$.
$^1$H NMR (CDCl$_3$): 8.27-8.24 (m, 1H), 7.84 (dd, J=8.5, 2.2 Hz, 1H), 7.49 (d, J=8.5 Hz, 1H), 7.32 (d, J=2.7 Hz, 1H), 7.06 (d, J=2.7 Hz, 1H), 7.03-7.00 (m, 1H), 3.84-7-3.72 (m, 2H), 3.01-2.81 (m, 2H), 2.80-2.66 (m, 3H), 2.05-1.27 (m, 10H).

Example 67

(4-Cyclopentyl-[1,4]diazepan-1-yl)-[6-(4-fluoro-phenoxy)-pyridin-3-yl]-methanone

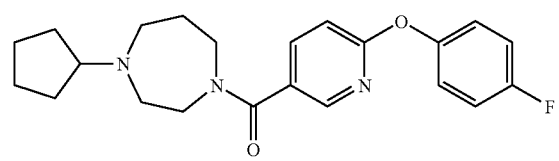 [SMILES: O=C(c1ccc(Oc2ccc(F)cc2)nc1)N1CCCN(C2CCCC2)CC1]

MS (ESI): mass calcd. for $C_{22}H_{26}FN_3O_2$, 383.20; m/z found, 384.5 [M+H]$^+$.
$^1$H NMR (CDCl$_3$): 8.30-8.20 (m, 1H), 8.87-7.76 (m, 1H), 7.15-7.09 (m, 4H), 6.97 (d, J=8.5 Hz, 1H), 3.87-3.71 (m, 2H), 3.62-3.47 (m, 2H), 3.10-2.67 (m, 5H), 2.15-1.24 (m, 10H).

Example 68

[5-(4-Chloro-phenoxy)-pyridin-2-yl]-(4-cyclobutyl-[1,4]diazepan-1-yl)-methanone trifluoroacetic acid salt

To a mixture of (5-bromo-pyridin-2-yl)-(4-isopropyl-piperazin-1-yl)-methanone (175 mg, 0.52 mmol) in DMA (2.5 mL) was added 4-chlorophenol (133 mg, 1.03 mmol) and Cs$_2$CO$_3$ (336 mg, 1.03 mmol). The mixture was heated at 200° C. for 90 min and cooled to rt. Water was added and mixture was extracted with DCM. The organic layer was concentrated and the residue was purified by FCC, followed by reverse phase HPLC, to give the title compound (108 mg, 42%). MS (ESI): mass calcd. for $C_{21}H_{24}ClN_3O_2$, 385.16; m/z found, 386.5 [M+H]$^+$. $^1$H NMR (CDCl$_3$): 8.36-8.27 (m, 1H), 7.71-7.62 (m, 1H), 7.40-7.29 (m, 3H), 7.05-6.97 (m, 2H), 3.86-3.76 (m, 2H), 3.75-3.68 (m, 1H), 3.68-3.62 (m, 2H), 3.00-2.84 (m, 1H), 2.71-2.63 (m, 1H), 2.62-2.46 (m, 2H), 2.13-1.96 (m 3H), 1.96-1.77 (m, 3H), 1.76-1.53 (m, 2H).

Example 69

(4-Cyclobutyl-[1,4]diazepan-1-yl)-1-yl)-[5-(4-fluoro-phenoxy)-pyridin-2-yl]-methanone trifluoroacetic acid salt

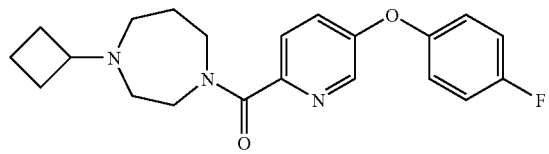 [SMILES: O=C(c1ccc(Oc2ccc(F)cc2)cn1)N1CCCN(C2CCC2)CC1]

MS (ESI): mass calcd. for $C_{21}H_{24}FN_3O_2$, 369.19; m/z found, 370.5 [M+H]$^+$.
$^1$H NMR (MeOD): 8.37-8.29 (m, 1H), 7.84-7.69 (m, 1H), 7.51-7.44 (m, 1H), 7.27-7.13 (m, 4H), 4.35-4.03 (m, 1H), 3.93-3.05 (m, 8H), 2.45-2.17 (m, 6H), 1.97-1.73 (m, 2H).

Example 70

[5-(3-Chloro-phenoxy)-pyridin-2-yl]-(4-cyclobutyl-[1,4]diazepan-1-yl)-methanone trifluoroacetic acid salt

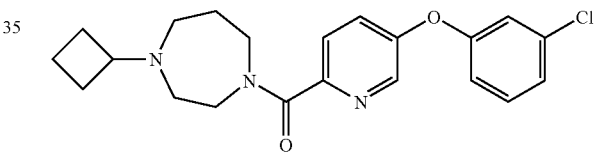

MS (ESI): mass calcd. for $C_{21}H_{24}ClN_3O_2$, 385.16; m/z found, 386.5 [M+H]$^+$.
$^1$H NMR (MeOD): 8.42-8.33 (m, 1H), 7.82-7.78 (m, 1H), 7.60-7.52 (m, 1H), 7.49-7.41 (m, 1H), 7.32-7.25 (m, 1H), 7.21-7.17 (m, 1H), 7.11-7.06 (m, 1H), 7.38-4.05 (m, 1H), 3.96-3.02 (m, 8H), 2.47-2.13 (m, 6H), 1.96-1.73 (m, 2H).

Example 71

(4-Cyclobutyl-[1,4]diazepan-1-yl)-[5-(3-fluoro-phenoxy)-pyridin-2-yl]-methanone trifluoroacetic acid salt

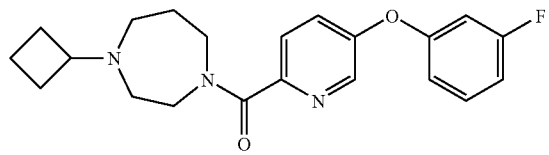 [SMILES: O=C(c1ccc(Oc2cccc(F)c2)cn1)N1CCCN(C2CCC2)CC1]

MS (ESI): mass calcd. for $C_{21}H_{24}FN_3O_2$, 369.18; m/z found, 370.5 [M+H]$^+$.
$^1$H NMR (MeOD): 8.44-8.34 (m, 1H), 7.82-7.78 (m, 1H), 7.62-7.54 (m, 1H), 7.52-7.43 (m, 1H), 7.07-6.99 (m, 1H), 6.99-6.90 (m, 2H), 4.39-4.03 (m, 1H), 3.96-3.03 (m, 8H), 2.46-2.16 (m, 6H), 1.98-1.76 (m, 2H).

Example 72

(4-Cyclobutyl-[1,4]diazepan-1-yl)-[5-(2-fluoro-phenoxy)-pyridin-2-yl]-methanone

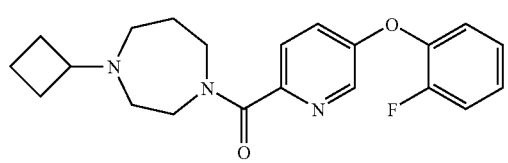 [SMILES: O=C(c1ccc(Oc2ccccc2F)cn1)N1CCCN(C2CCC2)CC1]

MS (ESI): mass calcd. for $C_{21}H_{24}FN_3O_2$, 369.18; m/z found, 370.5 [M+H]$^+$.
$^1$H NMR (CDCl$_3$): 8.36-8.26 (m, 1H), 7.68-7.60 (m, 1H), 7.31-7.12 (m, 4H), 3.84-3.75 (m, 2H), 3.72-3.67 (m, 1H), 3.67-3.61 (m, 1H), 3.0-2.82 (m, 1H), 2.67-2.61 (m, 1H), 2.58-2.44 (m, 3H), 2.11-1.95 (m, 3H), 1.93-1.74 (m, 3H), 1.74-1.54 (m, 2H).

Example 73

[6-(2-Chloro-phenoxy)-pyridin-3-yl]-(4-cyclobutyl-[1,4]diazepan-1-yl)-methanone

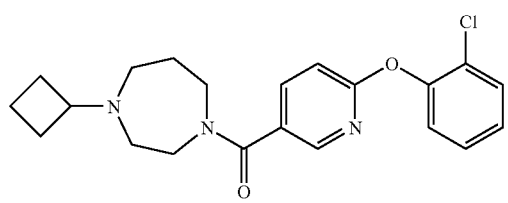 [SMILES: O=C(c1ccc(Oc2ccccc2Cl)nc1)N1CCCN(C2CCC2)CC1]

MS (ESI): mass calcd. for $C_{21}H_{24}ClN_3O_2$, 385.16; m/z found, 386.5 [M+H]$^+$.

Example 74

(4-Cyclopentyl-piperazin-1-yl)-[6-(4-fluoro-phenoxy)-pyridin-3-yl]-methanone

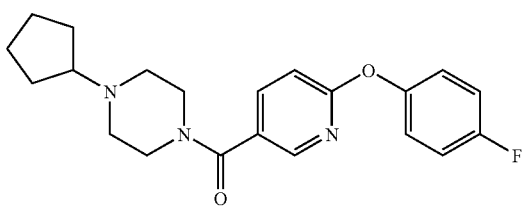 [SMILES: O=C(c1ccc(Oc2ccc(F)cc2)nc1)N1CCN(C2CCCC2)CC1]

MS (ESI): mass calcd. for $C_{21}H_{24}FN_3O_2$, 369.19; m/z found, 370.5 [M+H]$^+$.

Example 75

[6-(2-Chloro-phenoxy)-pyridin-3-yl]-(4-isopropyl-piperazin-1-yl)-methanone

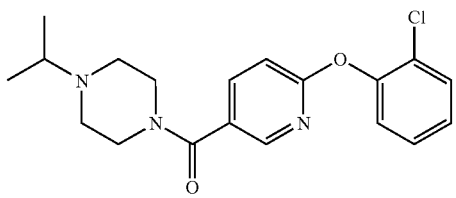 [SMILES: CC(C)N1CCN(C(=O)c2ccc(Oc3ccccc3Cl)nc2)CC1]

MS (ESI): mass calcd. for $C_{19}H_{22}ClN_3O_2$, 359.14; m/z found, 360.5 [M+H]$^+$.

Example 76

[6-(2-Chloro-phenoxy)-pyridin-3-yl]-(4-cyclopentyl-piperazin-1-yl)-methanone

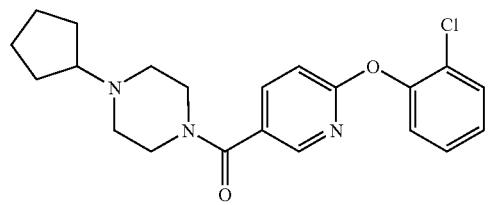 [SMILES: O=C(c1ccc(Oc2ccccc2Cl)nc1)N1CCN(C2CCCC2)CC1]

MS (ESI): mass calcd. for $C_{21}H_{24}ClN_3O_2$, 385.16; m/z found, 386.5 [M+H]$^+$.

Example 77

[6-(4-Chloro-phenoxy)-pyridin-3-yl]-(4-cyclopentyl-piperazin-1-yl)-methanone

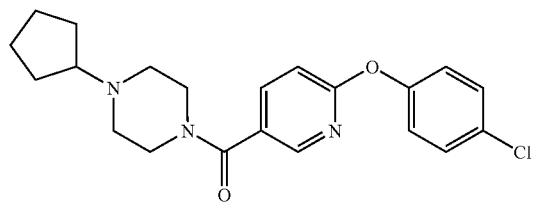 [SMILES: O=C(c1ccc(Oc2ccc(Cl)cc2)nc1)N1CCN(C2CCCC2)CC1]

MS (ESI): mass calcd. for $C_{21}H_{24}ClN_3O_2$, 385.16; m/z found, 386.5 [M+H]$^+$.

Example 78

(4-Cyclopentyl-piperazin-1-yl)-[6-(2-fluoro-phenoxy)-pyridin-3-yl]-methanone

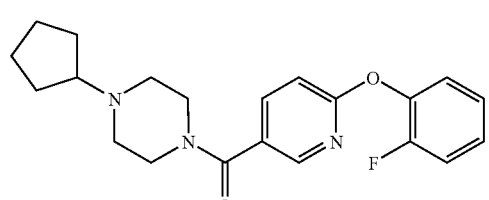

MS (ESI): mass calcd. for $C_{21}H_{24}FN_3O_2$, 369.19; m/z found, 370.5 [M+H]$^+$.

Example 79

(4-Cyclobutyl-piperazin-1-yl)-[6-(4-fluoro-phenoxy)-pyridin-3-yl]-methanone

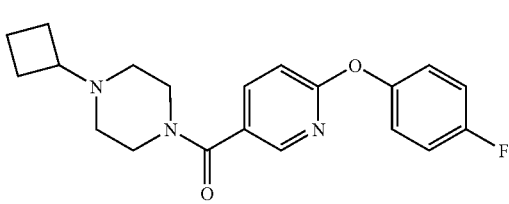 [SMILES: O=C(c1ccc(Oc2ccc(F)cc2)nc1)N1CCN(C2CCC2)CC1]

MS (ESI): mass calcd. for $C_{20}H_{22}FN_3O_2$, 355.17; m/z found, 356.5 $[M+H]^+$.

Example 80

[6-(4-Fluoro-phenoxy)-pyridin-3-yl]-(4-methyl-[1,4]diazepan-1-yl)-methanone

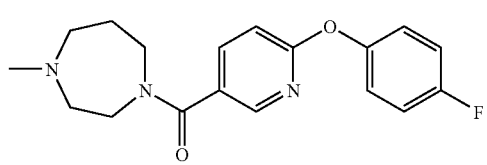 [SMILES: CN1CCCN(C(=O)c2ccc(Oc3ccc(F)cc3)nc2)CC1]

MS (ESI): mass calcd. for $C_{18}H_{20}FN_3O_2$, 329.15; m/z found, 330.5 $[M+H]^+$.

Example 81

6-(4-Cyclopropyl-[1,4]diazepane-1-carbonyl)-3-phenoxy-pyridine-2-carbonitrile

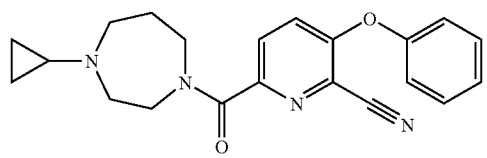 [SMILES: N#Cc1nc(C(=O)N2CCCN(C3CC3)CC2)ccc1Oc1ccccc1]

MS (ESI): mass calcd. for $C_{21}H_{22}N_4O_2$, 362.17; m/z found, 363.5 $[M+H]^+$.

$^1$H NMR (CDCl$_3$): 7.85 (d, J=8.9 Hz, 1H), 7.50-7.44 (m, 2H), 7.34-7.29 (m, 1H), 7.26 (t, J=4.5 Hz, 1H), 7.14-7.10 (m, 2H), 3.79-3.74 (m, 2H), 3.72-3.65 (m, 2H), 3.00-2.94 (m, 2H), 2.89-2.84 (m, 2H), 1.99-1.85 (m, 3H), 0.52-0.37 (m, 4H).

Example 82

6-(4-Cyclobutyl-[1,4]diazepane-1-carbonyl)-3-(4-fluoro-phenoxy)-pyridine-2-carbonitrile

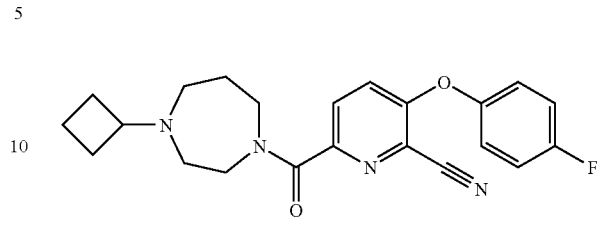

MS (ESI): mass calcd. for $C_{22}H_{23}FN_4O_2$, 394.18; m/z found, 395.5 $[M+H]^+$.

$^1$H NMR (CDCl$_3$): 7.93-7.81 (m, 1H), 7.23 (d, J=8.8 Hz, 1H), 7.19-7.13 (m, 2H), 7.13-7.08 (m, 2H), 3.82-3.76 (m, 2H), 3.75-3.67 (m, 2H), 2.99-2.87 (m, 1H), 2.67-2.61 (m, 2H), 2.55-2.47 (m, 2H), 2.11-1.93 (m, 4H), 1.91-1.76 (m, 2H), 1.75-1.59 (m, 2H).

Example 83

(4-Cyclobutyl-[1,4]diazepan-1-yl)-[6-(4-fluoro-phenylsulfanyl)-pyridin-3-yl]methanone

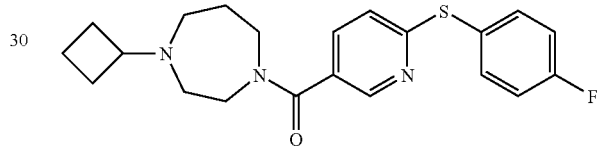

MS (ESI): mass calcd. for $C_{21}H_{24}FN_3OS$, 385.16; m/z found, 386.5 $[M+H]^+$.

$^1$H NMR (CDCl$_3$): 8.48-8.42 (m, 1H), 7.64-7.56 (m, 2H), 7.54 (dd, J=8.2, 2.2 Hz, 1H), 7.21-7.12 (m, 2H), 6.88 (d, J=8.2 Hz, 1H), 3.81-3.69 (m, 2H), 3.56-3.43 (m, 2H), 2.96-2.77 (m, 1H), 2.65-2.56 (m, 1H), 2.54-2.47 (m, 2H), 2.46-2.39 (m, 2H), 2.11-1.90 (m, 3H), 1.88-1.54 (m, 5H).

The compounds in Examples 84-93 were prepared using methods analogous to those described in the preceding examples.

Example 84

(4-Cyclobutyl-[1,4]diazepan-1-yl)-[5-(4-fluoro-phenylsulfanyl)-pyridin-2-yl]-methanone trifluoroacetic acid salt

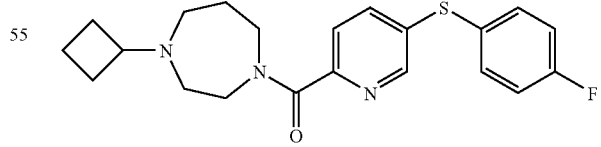

MS (ESI): mass calcd. for $C_{21}H_{24}FN_3OS$, 385.50; m/z found, 386.5 $[M+H]^+$.

$^1$H NMR (MeOD): 8.39-8.34 (m, 1H), 7.55-7.43 (m, 4H), 7.14-7.06 (m, 2H), 3.85-3.73 (m, 2H), 3.69-3.63 (m, 1H), 3.60 (t, J=6.5 Hz, 1H), 2.98-2.83 (m, 1H), 2.6-2.61 (m, 1H), 2.59-2.45 (m, 3H), 2.12-1.95 (m, 3H), 1.94-1.76 (m, 3H), 1.75-1.54 (m, 2H).

Example 85

[6-(4-Chloro-phenylsulfanyl)-pyridin-3-yl]-(4-cyclobutyl-[1,4]diazepan-1-yl)-methanone

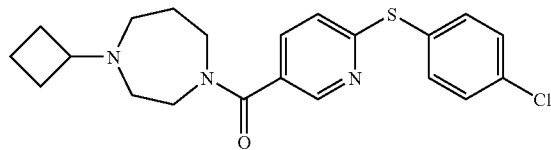 [SMILES: O=C(c1ccc(Sc2ccc(Cl)cc2)nc1)N1CCCN(C2CCC2)CC1]

MS (ESI): mass calcd. for $C_{21}H_{24}ClN_3OS$, 401.13; m/z found, 402.5 [M+H]$^+$.

$^1$H NMR (CDCl$_3$): 8.50-8.43 (m, 1H), 7.58-7.51 (m, 3H), 7.46-7.39 (m, 2H), 6.94 (d, J=8.2 Hz, 1H), 3.81-3.70 (m, 2H), 3.55-3.42 (m, 2H), 2.96-2.79 (m, 1H), 2.66-2.57 (m, 1H), 2.53-2.47 (m, 1H), 2.47-2.38 (m, 2H), 2.13-1.90 (m, 3H), 1.90-1.55 (m, 5H).

Example 86

(4-Cyclobutyl-[1,4]diazepan-1-yl)-(6-phenylsulfanyl-pyridin-3-yl)-methanone

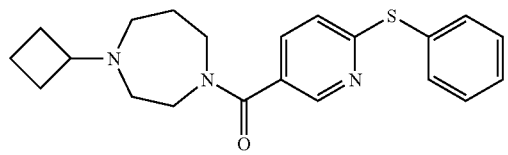

MS (ESI): mass calcd. for $C_{21}H_{25}N_3OS$, 367.17; m/z found, 368.5 [M+H]$^+$.

$^1$H NMR (CDCl$_3$): 8.50-8.44 (m, 1H), 7.65-7.57 (m, 2H), 7.55-7.50 (m, 1H), 7.49-7.42 (m, 3H), 6.88 (d, J=8.1 Hz, 1H), 3.80-3.69 (m, 2H), 3.54-3.43 (m, 2H), 2.96-2.78 (m, 1H), 2.65-2.56 (m, 1H), 2.53-2.46 (m, 1H), 2.46-2.39 (m, 2H), 2.11-1.91 (m, 3H), 1.90-1.54 (m, 6H).

Example 87

(4-Cyclopentyl-piperazin-1-yl)-[6-(3-methyl-4-methylsulfanyl-phenoxy)-pyridin-3-yl]methanone

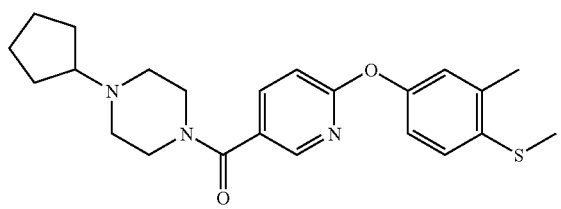 [SMILES: CSc1ccc(Oc2ccc(C(=O)N3CCN(C4CCCC4)CC3)cn2)cc1C]

MS (ESI): mass calcd. for $C_{23}H_{29}N_3O_2S$, 411.20; m/z found, 412.3 [M+H]$^+$.

$^1$H NMR (CDCl$_3$): 8.26 (dd, J=2.4, 0.8 Hz, 1H), 7.79 (dd, J=8.6, 2.4 Hz, 1H), 7.21 (d, J=8.2 Hz, 1H), 7.03-6.92 (m, 3H), 3.99-3.33 (m, 4H), 2.62-2.39 (m, 7H), 2.35 (s, 3H), 1.91-1.79 (m, 2H), 1.76-1.63 (m, 3H), 1.63-1.48 (m, 2H), 1.47-1.33 (m, 2H).

Example 88

(4-Isopropyl-piperazin-1-yl)-[6-(3-methyl-4-methylsulfanyl-phenoxy)-pyridin-3-yl]methanone

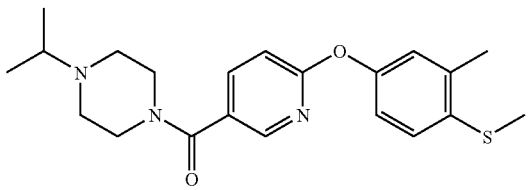 [SMILES: CSc1ccc(Oc2ccc(C(=O)N3CCN(C(C)C)CC3)cn2)cc1C]

MS (ESI): mass calcd. for $C_{21}H_{27}N_3O_2S$, 385.18; m/z found, 386.3 [M+H]$^+$.

$^1$H NMR (CDCl$_3$): 8.26 (dd, J=2.4, 0.8 Hz, 1H), 7.81-7.77 (m, 1H), 7.23-7.20 (m, 1H), 7.02-6.92 (m, 3H), 3.89-3.37 (m, 4H), 2.80-2.67 (m, 1H), 2.65-2.42 (m, 7H), 2.35 (s, 3H), 1.04 (d, J=6.5 Hz, 6H).

Example 89

[6-(4-Fluoro-phenoxy)-pyridin-3-yl]-(4-isopropyl-piperazin-1-yl)-methanone

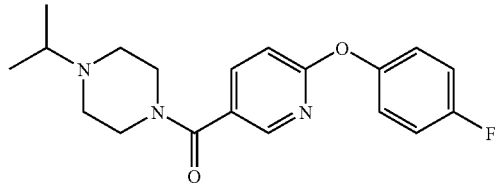 [SMILES: CC(C)N1CCN(C(=O)c2ccc(Oc3ccc(F)cc3)nc2)CC1]

MS (ESI): mass calcd. for $C_{19}H_{22}FN_3O_2$, 343.17; m/z found, 344.3 [M+H]$^+$.

$^1$H NMR (CDCl$_3$): 8.25-8.22 (m, 1H), 7.83-7.79 (m, 1H), 7.12-7.11 (m, 2H), 7.11-7.10 (m, 2H), 6.96 (dd, J=8.4, 0.8 Hz, 1H), 3.93-3.32 (m, 4H), 2.79-2.67 (m, 1H), 2.66-2.39 (m, 4H), 1.04 (d, J=6.5 Hz, 6H).

Example 90

(4-Ethyl-[1,4]diazepan-1-yl)-[6-(4-fluoro-phenoxy)-pyridin-3-yl]-methanone

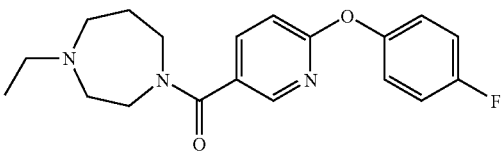 [SMILES: CCN1CCCN(C(=O)c2ccc(Oc3ccc(F)cc3)nc2)CC1]

MS (ESI): mass calcd. for $C_{19}H_{22}FN_3O_2$, 343.17; m/z found, 344.5 [M+H]$^+$.

$^1$H NMR (CDCl$_3$): 8.26 (br s, 1H), 7.88-7.77 (m, 1H), 7.19-7.06 (m, 4H), 6.97 (d, J=8.2 Hz, 1H), 3.86-3.72 (m, 2H), 3.63-3.46 (m, 2H), 2.87-2.77 (m, 1H), 2.74-2.51 (m, 5H), 2.03-1.95 (m, 1H), 1.92-1.82 (m, 1H), 1.16-1.00 (m, 3H).

Example 91

(4-Cyclobutyl-[1,4]diazepan-1-yl)-(5-phenylsulfanyl-pyridin-2-yl)-methanone

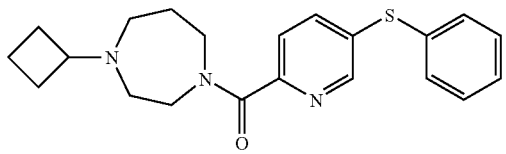 [SMILES: O=C(c1ccc(Sc2ccccc2)cn1)N1CCCN(C2CCC2)CC1]

MS (ESI): mass calcd. for $C_{21}H_{25}N_3OS$, 367.17; m/z found, 368.5 [M+H]$^+$.

$^1$H NMR (CDCl$_3$): 8.44-8.41 (m, 1H), 7.61-7.49 (m, 2H), 7.47-7.32 (m, 5H), 3.82-3.75 (m, 2H), 3.68-3.56 (m, 2H), 2.96-2.81 (m, 1H), 2.65-2.60 (m, 1H), 2.55-2.43 (m, 3H), 2.10-1.94 (m, 3H), 1.90-1.74 (m, 3H), 1.73-1.54 (m, 2H).

Example 92

[6-(4-Fluoro-phenoxy)-pyridin-3-yl]-(4-methyl-[1,4]diazepan-1-yl)-methanone

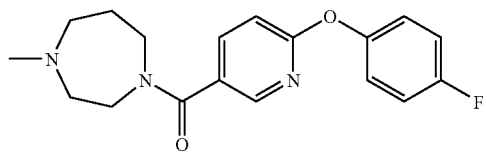 [SMILES: CN1CCCN(C(=O)c2ccc(Oc3ccc(F)cc3)nc2)CC1]

MS (ESI): mass calcd. for $C_{18}H_{20}FN_3O_2$, 329.15; m/z found, 330.5 [M+H]$^+$.

$^1$H NMR (CDCl$_3$): 8.30-8.21 (m, 1H), 7.86-7.76 (m, 1H), 7.17-7.18 (m, 4H), 6.97 (d, J=8.5 Hz, 1H), 3.85-3.75 (m, 2H), 3.63-3.57 (m, 1H), 3.57-3.51 (m, 1H), 2.78-2.73 (m, 1H), 2.68-2.63 (m, 1H), 2.62-2.54 (m, 2H), 2.45-2.32 (m, 3H), 2.06-1.97 (m, 1H), 1.94-1.86 (m, 1H).

Example 93

[6-(4-Fluoro-phenoxy)-pyridin-3-yl]-(4-isobutyl-piperazin-1-yl)-methanone

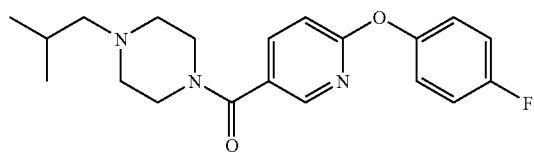 [SMILES: CC(C)CN1CCN(C(=O)c2ccc(Oc3ccc(F)cc3)nc2)CC1]

MS (ESI): mass calcd. for $C_{20}H_{24}FN_3O_2$, 357.19; m/z found, 358.5 [M+H]$^+$.

$^1$H NMR (CDCl$_3$): 8.23 (dd, J=2.5, 0.9 Hz, 1H), 7.80 (dd, J=8.8, 2.2 Hz, 1H), 7.13-7.09 (m, 4H), 6.96 (dd, J=8.3, 0.8 Hz, 1H), 3.86-3.37 (br d, 4H), 2.53-2.28 (br s, 4H), 2.10 (d, J=8.1 Hz, 2H), 1.83-1.71 (m, 1H), 0.90 (d, J=6.3 Hz, 6H).

The compounds in Examples 94-105 were prepared using methods analogous to those described in the preceding examples.

Example 94

(4-Cyclobutyl-[1,4]diazepan-1-yl)-(5-phenylsulfanyl-pyridin-2-yl)-methanone

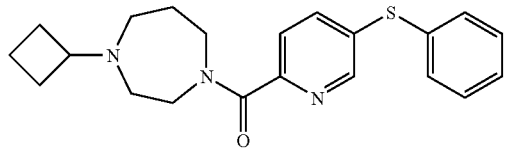 [SMILES: O=C(c1ccc(Sc2ccccc2)cn1)N1CCCN(C2CCC2)CC1]

MS (ESI): mass calcd. for $C_{21}H_{25}N_3OS$, 367.2; m/z found, 368.5 [M+H]$^+$. $^1$H NMR (CDCl$_3$): 8.45-8.39 (m, 1H), 7.60-7.55 (m, 1H), 7.55-7.50 (m, 1H), 7.47-7.42 (m, 2H), 7.42-7.33 (m, 3H), 3.82-3.75 (m, 2H), 3.67-3.63 (m, 1H), 3.62-3.57 (m, 1H), 2.96-2.80 (m, 1H), 2.65-2.60 (m, 1H), 2.55-2.43 (m, 3H), 2.10-1.94 (m, 3H), 1.91-1.73 (m, 3H), 1.72-1.54 (m, 2H).

Example 95

(4-Cyclobutyl-[1,4]diazepan-1-yl)-(6-phenylsulfanyl-pyridin-3-yl)-methanone

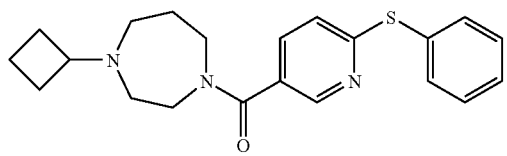 [SMILES: O=C(c1ccc(Sc2ccccc2)nc1)N1CCCN(C2CCC2)CC1]

MS (ESI): mass calcd. for $C_{21}H_{25}N_3OS$, 367.2; m/z found, 368.5 [M+H]$^+$. $^1$H NMR (CDCl$_3$): 8.51-8.43 (m, 1H), 7.65-7.58 (m, 2H), 7.55-7.49 (m, 1H), 7.49-7.42 (m, 3H), 6.88 (d, J=8.4 Hz, 1H), 3.80-3.69 (m, 2H), 3.56-3.43 (m, 2H), 2.95-2.77 (m, 1H), 2.65-2.56 (m, 1H), 2.53-2.36 (m, 3H), 2.11-1.91 (m, 3H), 1.90-1.54 (m, 5H).

Example 96

[6-(4-Chloro-phenylsulfanyl)-pyridin-3-yl]-(4-cyclobutyl-[1,4]diazepan-1-yl)-methanone

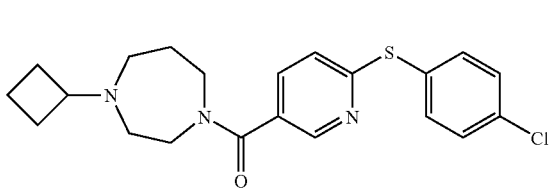 [SMILES: O=C(c1ccc(Sc2ccc(Cl)cc2)nc1)N1CCCN(C2CCC2)CC1]

MS (ESI): mass calcd. for $C_{21}H_{24}ClN_3OS$, 401.1; m/z found, 402.5 [M+H]$^+$.

$^1$H NMR (CDCl$_3$): 8.49-8.43 (m, 1H), 7.58-7.50 (m, 3H), 7.45-7.42 (m, 1H), 7.42-7.40 (m, 1H), 6.94 (d, J=8.2 Hz, 1H), 3.79-3.71 (m, 2H), 3.54-3.44 (m, 2H), 2.96-2.78 (m, 1H), 2.67-2.57 (m, 1H), 2.55-2.38 (m, 3H), 2.13-1.91 (m, 3H), 1.90-1.53 (m, 5H).

Example 97

(4-Cyclobutyl-[1,4]diazepan-1-yl)-[6-(4-fluoro-phenylsulfanyl)-pyridin-3-yl]-methanone

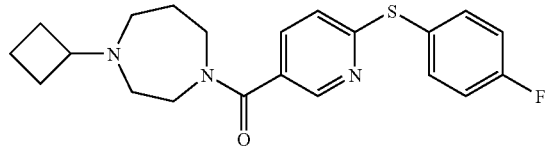 [SMILES: O=C(c1ccc(Sc2ccc(F)cc2)nc1)N1CCCN(C2CCC2)CC1]

MS (ESI): mass calcd. for $C_{21}H_{24}FN_3OS$, 385.2; m/z found, 386.5 [M+H]$^+$.
$^1$H NMR (CDCl$_3$): 8.48-8.44 (m, 1H), 7.63-7.57 (m, 2H), 7.54 (dd, J=8.2, 2.2 Hz, 1H), 7.19-7.11 (m, 2H), 6.88 (d, J=8.2 Hz, 1H), 3.80-3.70 (m, 2H), 3.55-3.34 (m, 2H), 2.95-2.78 (m, 1H), 2.65-2.57 (m, 1H), 2.53-2.46 (m, 1H), 2.46-2.38 (m, 2H), 2.10-1.91 (m, 3H), 1.89-1.54 (m, 5H).

Example 98

(4-Ethyl-[1,4]diazepan-1-yl)-[6-(4-fluoro-phenoxy)-pyridin-3-yl]-methanone

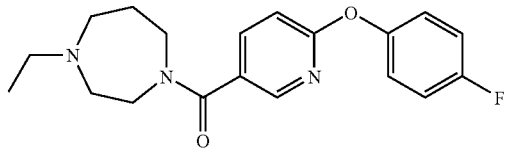 [SMILES: CCN1CCCN(C(=O)c2ccc(Oc3ccc(F)cc3)nc2)CC1]

MS (ESI): mass calcd. for $C_{19}H_{22}FN_3O_2$, 343.2; m/z found, 344.5 [M+H]$^+$. $^1$H NMR (CDCl$_3$): 8.25 (br s, 1H), 7.88-7.56 (m, 1H), 7.18-7.10 (m, 4H), 6.97 (d, J=8.2 Hz, 1H), 3.87-3.72 (m, 2H), 3.63-3.48 (m, 2H), 2.87-2.76 (m, 1H), 2.75-2.49 (m, 5H), 2.03-1.94 (m, 1H), 1.92-1.82 (m, 1H), 1.16-1.00 (m, 3H).

Example 99

[6-(4-Fluoro-phenoxy)-pyridin-3-yl]-(4-isopropyl-piperazin-1-yl)-methanone

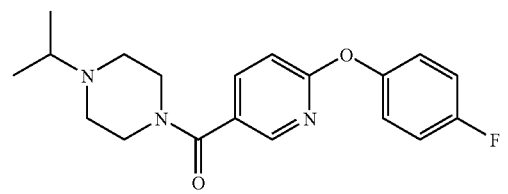 [SMILES: CC(C)N1CCN(C(=O)c2ccc(Oc3ccc(F)cc3)nc2)CC1]

MS (ESI): mass calcd. for $C_{19}H_{22}FN_3O_2$, 343.2; m/z found, 344.5 [M+H]$^+$. $^1$H NMR (CDCl$_3$): 8.24-8.21 (m, 1H), 7.83-7.79 (m, 1H), 7.12 (br s, 2H), 7.11-7.08 (m, 2H), 6.98-6.94 (m, 1H), 3.93-3.63 (m, 2H), 3.61-3.36 (m, 2H), 2.80-2.67 (m, 1H), 2.66-2.37 (m, 4H), 1.04 (d, J=6.5 Hz, 6H).

Example 100

(4-Cyclopentyl-piperazin-1-yl)-[6-(3-methyl-4-methylsulfanyl-phenoxy)-pyridin-3-yl]methanone

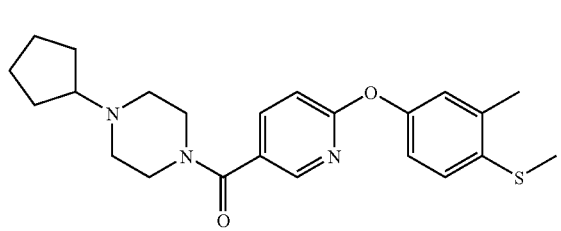 [SMILES: CSc1ccc(Oc2ccc(C(=O)N3CCN(C4CCCC4)CC3)cn2)cc1C]

MS (ESI): mass calcd. for $C_{23}H_{29}N_3O_2S$, 411.2; m/z found, 412.3 [M+H]$^+$. $^1$H NMR (CDCl$_3$): 8.26 (dd, J=2.4, 0.8 Hz, 1H), 7.83-7.77 (m, 1H), 7.21 (d, J=8.4 Hz, 1H), 7.03-6.92 (m, 3H), 3.95-3.36 (m, 4H), 2.69-2.41 (m, 7H), 2.35 (s, 3H), 1.93-1.80 (m, 2H), 1.78-1.62 (m, 3H), 1.62-1.49 (m, 2H), 1.46-1.32 (m, 2H).

Example 101

(4-Isopropyl-piperazin-1-yl)-[6-(3-methyl-4-methylsulfanyl-phenoxy)-pyridin-3-yl]-methanone

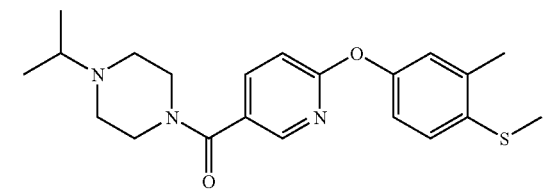 [SMILES: CSc1ccc(Oc2ccc(C(=O)N3CCN(C(C)C)CC3)cn2)cc1C]

MS (ESI): mass calcd. for $C_{21}H_{27}N_3O_2S$, 385.2; m/z found, 386.3 [M+H]$^+$. $^1$H NMR (CDCl$_3$): 8.26 (dd, J=2.4, 0.8 Hz, 1H), 7.82-7.76 (m, 1H), 7.21 (d, J=8.2 Hz, 1H), 7.01-6.94 (m, 3H), 3.88-3.35 (m, 4H), 2.80-2.68 (m, 1H), 2.66-2.41 (m, 7H), 2.35 (m, 3H), 1.05 (d, J=6.5 Hz, 6H).

Example 102

(4-Cyclobutyl-[1,4]diazepan-1-yl)-(6-o-tolyloxy-pyridin-3-yl)-methanone

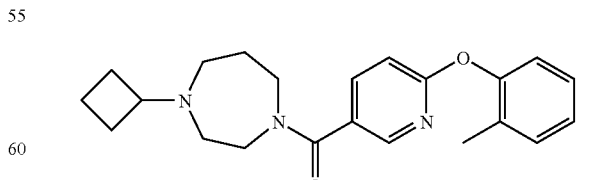

MS (ESI): mass calcd. for $C_{21}H_{27}N_3O_2S$, 365.2; m/z found, 366.3 [M+H]$^+$. $^1$H NMR (CDCl$_3$): 8.25 (br s, 1H), 7.82-7.77 (m, 1H), 7.33-7.29 (m, 1H), 7.28-7.24 (m, 1H), 7.21-7.16 (m, 1H), 7.09-7.05 (m, 1H), 6.94-6.90 (m, 1H), 3.81-3.73 (m, 2H), 3.60-3.50 (m, 2H), 2.98-2.82 (m, 1H), 2.67-2.59 (m, 1H), 2.54-2.39 (m, 3H), 2.19 (s, 3H), 2.12-1.93 (m, 3H), 1.92-1.54 (m, 5H).

Example 103

(4-Cyclobutyl-[1,4]diazepan-1-yl)-(6-m-tolyloxy-pyridin-3-yl)-methanone

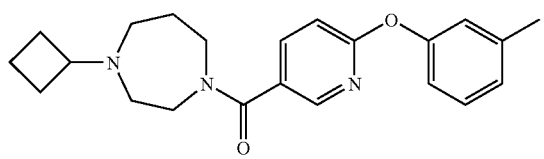 [SMILES: Cc1cccc(Oc2ccc(C(=O)N3CCCN(C4CCC4)CC3)cn2)c1]

MS (ESI): mass calcd. for $C_{21}H_{27}N_3O_2S$, 365.2; m/z found, 366.3 [M+H]$^+$. $^1$H NMR (CDCl$_3$): 8.26 (br s, 1H), 7.78 (dd, J=8.4, 2.4 Hz, 1H), 7.32-7.27 (m, 1H), 7.07-7.02 (m, 1H), 6.97-6.90 (m, 3H), 3.81-3.71 (m, 2H), 3.59-3.47 (m, 2H), 2.95-2.78 (m, 1H), 2.66-2.58 (m, 1H), 2.54-2.39 (m, 3H), 2.37 (s, 3H), 2.11-1.91 (m, 3H), 1.90-1.56 (m, 5H).

Example 104

(4-Cyclobutyl-[1,4]diazepan-1-yl)-(6-p-tolyloxy-pyridin-3-yl)-methanone

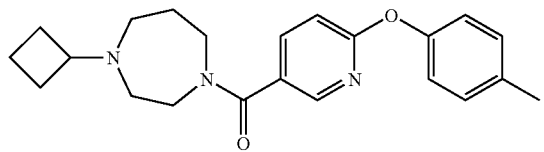 [SMILES: Cc1ccc(Oc2ccc(C(=O)N3CCCN(C4CCC4)CC3)cn2)cc1]

MS (ESI): mass calcd. for $C_{21}H_{27}N_3O_2S$, 365.2; m/z found, 366.3 [M+H]$^+$. $^1$H NMR (CDCl$_3$): 8.24 (br s, 1H), 7.80-7.73 (m, 1H), 7.24-7.18 (m, 2H), 7.05-7.00 (m, 2H), 6.94-6.90 (m, 1H), 3.81-3.70 (m, 2H), 3.59-3.46 (m, 2H), 2.95-2.78 (m, 1H), 2.67-2.57 (m, 1H), 2.55-2.40 (m, 3H), 2.37 (s, 3H), 2.13-1.91 (m, 3H), 1.91-1.54 (m, 5H).

Example 105

(4-Cyclobutyl-[1,4]diazepan-1-yl)-[6-(4-methylsulfanyl-phenoxy)-pyridin-3-yl]-methanone

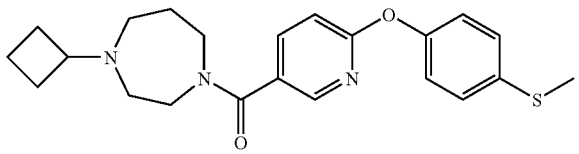 [SMILES: CSc1ccc(Oc2ccc(C(=O)N3CCCN(C4CCC4)CC3)cn2)cc1]

MS (ESI): mass calcd. for $C_{22}H_{27}N_3O_2S$, 397.2; m/z found, 398.3 [M+H]$^+$. $^1$H NMR (CDCl$_3$): 8.25 (br s, 1H), 7.78 (dd, J=8.4, 2.4 Hz, 1H), 7.36-7.29 (m, 2H), 7.14-7.05 (m, 2H), 6.97-6.90 (m, 1H), 3.83-3.70 (m, 2H), 3.59-3.46 (m, 2H), 2.97-2.77 (m, 1H), 2.66-2.58 (m, 1H), 2.55-2.38 (m, 6H), 2.11-1.91 (m, 3H), 1.91-1.52 (m, 5H).

Example 106

(4-Cyclobutyl-[1,4]diazepan-1-yl)-[6-(4-fluoro-phenoxy)-pyridin-3-yl]-methanone

5-Bromo-2-(4-fluoro-phenoxy)-pyridine (27.2 mg, 0.102 mmol) was dissolved in Et$_2$O (0.8 mL). The mixture was cooled to −78° C. n-Butyl lithium (0.040 mL, 2.5 M in hexanes) was added and the reaction mixture was stirred for 5 min at −78° C. CO$_2$ gas (from dry ice, passed through 4 Å molecular sieves) was bubbled through the mixture and the reaction was allowed to warm to 23° C. over 3 min. The solvents were removed by distillation then DCM (0.5 mL), DMF (0.05 mL) and oxalyl chloride (0.070 mL, 2.0 M in DCM) were added. The mixture was stirred for 3 min then cyclobutyl diazepine bis-HCl salt (27.6 mg, 0.122 mmol) and iPr$_2$NEt (0.1 mL) were added to the reaction following dissolution in DCM (0.5 mL). The mixture was stirred for 3 min at 23° C. and was concentrated. Analysis by HPLC indicated a yield of 80%. Chromatography on SiO$_2$ gave 21.5 mg (57%) of the title compound that was >90% pure by NMR.

Note: The synthesis may also be performed with $^{11}$CO$_2$ to provide the $^{11}$C-labelled analog of the title compound.

Example 107

(4-Cyclobutyl-[1,4]diazepan-1-yl)-[6-(4-fluoro-phenoxy)-pyridin-3-yl]-methanone hydrochloride monohydrate Step A: 4-Cyclobutyl-[1,4]diazepane-1-carboxylic acid tert-butyl ester A 3-L, 3-necked, round-bottomed flask under a positive pressure of nitrogen was equipped with a mechanical stirrer and charged with tert-butylhomopiperazine-1-carboxylate (1-BOC-homopiperazine) (73.0 g, 365.0 mmol) and anhydrous dichloroethane (800 mL). To this stirred solution was added cyclobutanone (25.5 g, 363.8 mmol). The pale yellow reaction was stirred at rt for 1 h, following which, sodium triacetoxyborohydride (92.5 g, 436.3 mmol) was added portion-wise over 1 h. The reaction mixture was stirred for 48 h. 1 N NaOH$_{(aq)}$ (225 mL) was added to the reaction mixture and stirred for 1 h. The phases were separated and the aqueous layer was extracted with dichloroethane (2×100 mL). The organic layers were pooled, washed with satd. aq. NaCl (1×250 mL), dried over anhydrous Na$_2$SO$_4$ and filtered. The solvent was removed by rotary evaporation under reduced pressure to afford the crude product as pale yellow semi-solid (92.4 g, 98%). $^1$H-NMR (400 MHz, CDCl$_3$) δ ppm: 3.59-3.40 (m, 4H), 2.98-2.84 (m, 1H), 2.59-2.43 (m, 4H), 2.12-2.03 (m, 2H), 2.00-1.83 (m, 4H), 1.76-1.55 (m, 2H), 1.51-1.41 (s, 9H). MS m/z (ESI+): 255.2 (M+H$^+$).

Step B: 1-Cyclobutyl-[1,4]diazepane dihydrochloride

A 1-L, 3-necked, round-bottomed flask was equipped with a mechanical stirrer and a reflux condenser. The flask was charged with a slurry of crude 4-cyclobutyl-[1,4]diazepane-1-carboxylic acid tert-butyl ester (92.4 g, 363.8 mmol) in a mixture of dioxane/MeOH (100 mL/50 mL). HCl (4 M in dioxane, 250 mL) was added with vigorous mechanical agitation following which the reaction mixture was heated to ca. 55° C. in an oil bath. A pale orange-yellow solution resulted. The reaction mixture was maintained at ca. 55° C. for 16 h. After cooling to rt, the reaction mixture, a thick slurry, was transferred to a 2-L recovery flask and concentrated to a pasty solid. Methyl tert-butyl ether (200 mL) was added, and the slurry agitated at ca. 55° C. in an oil bath for 1 h. The solvent was removed by rotary evaporation under reduced pressure to afford the product as an off-white solid (81.2 g, 98%). $^1$H-NMR (400 MHz, DMSO-d$_6$) δ ppm: 11.92 (s, 1H), 9.87 (s, 1H), 9.46 (s, 1H), 3.76-3.03 (m, 9H), 2.43-2.33 (m, 2H), 2.17-2.15 (m, 4H), 1.75-1.60 (m, 2H). MS m/z (ESI+): 155.1 (M+H$^+$).

Step C: (6-Chloro-pyridin-3-yl)-(4-cyclobutyl-[1,4] diazepan-1-yl)-methanone

A 5-L, 3-necked, round-bottomed flask was equipped with a mechanical stirrer and a thermocouple and charged with 1-cyclobutyl-[1,4]diazepane dihydrochloride (110.0 g, 484.6 mmol), 1 N NaOH (1400 mL) and isopropyl acetate (600 mL). A pre-cooled (0° C.). solution of 6-chloronicotinyl chloride (82.7 g, 470.0 mmol) in isopropyl acetate (800 mL) was added via an addition funnel at a rate such that the reaction temperature was maintained between 5-10° C. After the addition was complete, the reaction mixture was warmed to rt and stirred for 2 h (pH of reaction mixture ca. 5.6). The reaction mixture was basified with 2 N NaOH$_{(aq)}$ (to pH ca. 13). The phases were separated and the aqueous layer was extracted with isopropyl acetate (2×300 mL). Some reddish-brown flocculent material was observed during the extractions. The organic layers were pooled and filtered through a pad of diatomaceous earth. The filtrate was washed with satd. aq. NaCl (1×300 mL) and dried over anhydrous Na$_2$SO$_4$. Filtration and removal of the solvent by rotary evaporation under reduced pressure afforded the crude product as a reddish brown oil (126.0 g, 91%). $^1$H-NMR (400 MHz, CDCl$_3$) δ ppm: 8.45 (m, 1H), 7.74 (m, 1H), 7.39 (m, 1H), 3.86-3.76 (m, 2H), 3.53-3.45 (m, 2H), 3.05-2.80 (m, 1H), 2.70 (br s, 1H), 2.62-2.45 (m 3H), 2.10-1.56 (m, 8H). MS m/z (ESI+): 294.1 (M+H$^+$). HPLC (Method B): R$_t$=6.06 min.

Step D: (4-Cyclobutyl-[1,4]diazepan-1-yl)-[6-(4-fluoro-phenoxy)-pyridin-3-yl]-methanone A 5-L, 3-necked, round-bottomed flask under a positive pressure of nitrogen was equipped with a mechanical stirrer, thermocouple and a reflux condenser. The flask was charged with anhydrous DMA (625 mL), 4-fluorophenol (57.3 g, 511.6 mmol) and Cs$_2$CO$_3$ (278.0 g, 853.3 mmol). The yellow colored suspension was stirred for 15 min following which a solution of crude (6-chloro-pyridin-3-yl)-(4-cyclobutyl-[1,4] diazepan-1-yl)-methanone (125.0 g, 426.6 mmol) in anhydrous DMA (625 mL) was added via an addition funnel over 0.5 h. The reaction mixture was heated to ca. 100° C. and maintained at that temperature for 12 h. The reaction mixture was cooled to rt, then filtered through a pad of diatomaceous earth (3" pad in a 600 mL coarse glass frit) and the pad was washed with DMA (2×125 mL). The filtrate was diluted with ice water (ca. 1 L) and 2 N NaOH$_{(aq)}$ (500 mL). The pH of the reaction mixture was ca. 13. Out of convenience, the reaction mixture was divided into two approximately equal portions. Each portion was extracted with MTBE (3×300 mL). The organic layers were pooled, dried over anhydrous MgSO$_4$, filtered and concentrated by rotary evaporation under reduced pressure to afford the a thick orange colored oil. HPLC analysis of the crude material indicated a peak at ca. 9.18 min. The crude product was dissolved in anhydrous Et$_2$O (1 L) and stirred at rt for 16 h. A pale yellow solid precipitated and this was collected by filtration (ca. 8.5 g). $^1$H-NMR (D$_2$O) spectrum of this solid was very similar to that of the product. Upon stirring the solid in aq. HCl, the peak at 9.18 min slowly disappeared with the concomitant appearance of a peak at 7.30 min (desired product). Presumably, the product formed a complex with the drying agent (MgSO$_4$). Azeotropic drying or the use of sodium sulfate as the drying agent is recommended. The solid was collected to give the title compound (120 g, 76% after Et$_2$O trituration). $^1$H NMR (400 MHz, CDCl$_3$) δ ppm: 8.23 (br s, 1H), 7.79 (dd, J=8.48, 2.39 Hz, 1H), 7.11-7.10 (m, 4H), 6.95 (d, J=8.48 Hz, 1H), 3.76 (t, J=5.84 Hz, 2H), 3.55-3.50 (m, 2H), 2.90-2.84 (m, 1H), 2.61 (t, J=4.71 Hz, 1H), 2.55-2.37 (m, 3H), 2.06-1.92 (m, 3H), 1.88-1.56 (m, 5H). MS m/z (ESI+): 370.1 (M+H+). HPLC (Method B): R$_t$=7.30 min.

Step E: (4-Cyclobutyl-[1,4]diazepan-1-yl)-[6-(4-fluoro-phenoxy)-pyridin-3-yl]-methanone hydrochloride monohydrate A 3-L, 3-necked, round-bottomed flask was equipped with a mechanical stirrer, addition funnel and a thermocouple. The flask was charged with a solution of crude (4-cyclobutyl-[1, 4]diazepan-1-yl)-[6-(4-fluoro-phenoxy)-pyridin-3-yl] methanone (118.0 g, 319.8 mmol) in ethanol/Et$_2$O (1:1, 800 mL). The reaction vessel was cooled to ca. 5° C. in an ice-water bath. HCl (2 M in Et$_2$O, 152 mL, 304 mmol, 0.95 equiv.) was added drop-wise via the addition funnel over 30 min. The resulting suspension was stirred for 2 h, and then diluted with Et$_2$O (200 mL). The resulting suspension was stirred at rt for 16 h. The suspension was re-cooled to 0° C., maintained at that temperature for 2 h with agitation, then filtered. The filter-cake was broken and washed with Et$_2$O/ EtOH (60:40, 100 mL×3) and the product dried under house vacuum for 1 h, then in a vacuum oven at 50° C. for 48 h. The product (113.5 g) was suspended in Et$_2$O (2 L) and agitated (mechanical stirrer) for 6 h. The suspension was filtered, the filter-cake broken and washed with Et$_2$O (3×100 mL). The product was dried in a vacuum oven at 45° C. for 16 h (106.8 g, 82%). $^1$H NMR (400 MHz, D$_2$O) δ ppm: 8.09-8.05 (m, 1H), 7.88-7.81 (m, 1H), 7.13-7.09 (m, 4H), 7.02 (d, J=8.64 Hz, 1H), 4.15-4.10 (m, 1H), 3.87-3.39 (m, 6H), 3.07-2.90 (m, 2H), 2.28-1.99 (m, 6H), 1.75-1.63 (m, 2H). MS m/z (ESI+): 370.1 (M+H$^+$). HPLC (Method B): R$_t$=7.13 min. Anal. calcd for C$_{21}$H$_{24}$FN$_3$O$_2$.HCl.H$_2$O (monohydrochloride-monohydrate): C, 59.50; H, 6.42; N, 9.91. Found: C, 59.36; H, 6.66; N, 9.98.

Example 108

(4-Cyclobutyl-[1,4]diazepan-1-yl)-[6-(4-fluoro-phenoxy)-pyridin-3-yl]-methanone hydrochloride monohydrate (Alternate Method)

Step A: Ethyl 6-(4-fluorophenoxy)nicotinate

To a 2-L, 3-necked, round-bottomed flask equipped with a mechanical stirrer, a thermo couple, and a condenser was added DMF (194 mL), ethyl 6-chloronicotinate (100.00 g, 0.522 mol), and 4-fluorophenol (65.09 g, 0.575 mol). A brown solution formed after stirring for 5-10 min. To the solution was then added Cs$_2$CO$_3$ (189.19 g, 0.575 mol) in one portion. The reaction temperature increased from 20° C. to 30° C. over 10 min without external heating and then started cooling down. The resulting suspension was stirred at rt for 2-3 h and the internal reaction temperature cooled back to 23-25° C. The reaction mixture was then heated to 60° C. and stirred for 18-20 h. HPLC analysis indicated that the reaction was complete. The heating mantle was removed and the reaction mixture was allowed to cool to 25-30° C. To the mixture was added deionized water (145.5 mL) in a steady stream over 5 min and a slight exotherm was observed. The resulting suspension was stirred at rt for 15-20 min. Two additional portions of deionized water (145.5 mL each) were added and the suspension was stirred at rt for 15-30 min. The pH of the suspension was around 9-10. The solid product was collected by vacuum filtration, rinsed thoroughly with deionized water in portions. The filter cake as dried in a filter funnel by pulling through air for 24 h. The product was isolated as a white solid (133.6 g). mp: 68.0° C. (by DSC). $^1$H NMR (CDCl$_3$): δ 8.81 (d, J=2.6 Hz, 1H), 8.22 (dd, J=8.5, 2.6 Hz, 1H), 7.12 (br s, 2H), 7.10 (d, J=1.0 Hz, 2H), 6.94 (d, J=8.5 Hz, 1H), 4.38 (q, J=7.1 Hz, 2H), 4.38 (t, J=7.1 Hz, 3H). MS (ESI): M+H$^+$=262.1.

Step B: [1,4]Diazepan-1-yl-[6-(4-fluoro-phenoxy)-pyridin-3-yl]-methanone

A 5-L, 4-necked round-bottomed flask fitted with an external cooling bath, overhead stirrer, thermometer, addition funnel, under a nitrogen atmosphere was charged with THF (2 L), a solution of homopiperazine (234.4 g, 2.34 mol) in THF (20 mL), and ethyl 6-(4-fluorophenoxy)nicotinate (dry; 251.34 g, 0.962 mol). The mixture was stirred to dissolve the solids, leaving a slightly cloudy solution. The mixture was cooled to ca. 0° C. and treated with hexyllithium (440.41 g, 1.43 mol) via an addition funnel over a period of ca. 0.75 to 1 h. The addition rate and external cooling were adjusted such that the internal reaction temperature was maintained between 0 and 10° C. After addition of the hexyllithium is complete, the reaction was warmed to ca. 25° C. and monitored by HPLC until the ester is consumed (ca. 2 h). The mixture was cooled to ca. 15° C. and quenched with water (1 L). The phases were separated and the amount of product in the aqueous phase was checked by HPLC prior to being discarded. The aqueous phase was optionally extracted with MTBE (¼ volume). The basic aqueous phase was discarded and the combined organic phases were extracted with HCl (2 N, 600 mL) (aqueous phase pH ca. 2-3). The phases were separated and the organic phase was extracted with HCl (2 N, 200 mL). The organic phase was discarded. The aqueous extracts were combined and allowed to stand for several hours for any remaining {4-[6-(4-fluoro-phenoxy)-pyridine-3-carbonyl]-[1,4]diazepan-1-yl}-[6-(4-fluoro-phenoxy)-pyridin-3-yl]methanone (diamide by-product) to crystallize as a fine solid. The solid was removed by filtration through a glass fiber filter and the filtrate was extracted with MTBE (7×180 mL) to remove any remaining diamide. The aqueous phase was treated with NaOH (50% w/w; 175.4 g, 2.19 mol). Once the pH was greater than 9, a second liquid phase separated. The two phases were separated and the aqueous phase was extracted with EtOAc (2×150 mL). The organic phases obtained from the basified aqueous extracts are combined and washed with satd. aq. NaCl (100 mL). Once the phases are completely separated, the organic phase was placed in a distillation apparatus and treated with EtOAc (100 mL). The excess EtOAc was distilled at atmospheric pressure to azeotropically remove water. An additional charge of EtOAc (600 mL) was added in several portions and distillation was continued (repeated until Karl-Fischer analysis of the pot residue showed less than 0.8% water). The residue was filtered hot to remove NaCl and the filtrate was stirred for several hours until a large amount of solid formed. The mixture was treated slowly with heptane (500 mL) over a period of about 1 hour and allowed to stir an additional hour. The solid is isolated by filtration and dried to give the title compound (168.9 g). mp: 95.4° C. (by DSC). $^1$H-NMR (CDCl$_3$): δ 8.24 (d, J=2.2 Hz, 1H), 7.80 (dd, J=2.2, 8.4 Hz, 1H), 7.12 (s, 2H), 6.95 (d, J=8.4 Hz, 1H), 3.76 (br m, 2H), 3.51 (br m, 2H), 3.60 (br m, 1H), 2.90 (br m, 3H), 1.90 (br m, 1H), 1.80 (br s, 3H).

Step C: (4-Cyclobutyl-[1,4]diazepan-1-yl)-[6-(4-fluoro-phenoxy)-pyridin-3-yl]-methanone hydrochloride monohydrate To a 3-L, 3-necked, round-bottomed flask equipped with a mechanical stirrer, a thermo couple, and a condenser was charged EtOAc (1080 mL) and (1,4-diazepan-1-yl)-(6-(4-fluorophenoxy)pyridin-3-yl)methanone (136.2 g, 0.428 mol). The resulting suspension was warmed to 32-35° C. to dissolve all solids. The solution was then cooled to 5-10° C., treated with cyclobutanone (36.33 g, 0.513 mol), and the mixture was stirred at 5-10° C. for 5-10 min. To the solution at 5-10° C. was added sodium triacetoxyborohydride (143.09 g, 0.641 mol) in several portions over 15-20 min. The reaction temperature was kept below 15° C. by using cooling bath and by adjusting the addition rate. The resulting suspension was stirred at 15° C. for 10-15 min and then at rt (20-24° C.) for 2.5-3 h. Once HPLC analysis indicated the reaction was complete (<1 area % starting material), the reaction was quenched with a solution of K$_2$CO$_3$ (164.15 g, 1.175 mol) in deionized water (540 mL). The internal reaction temperature increased from 22° C. to 30° C. with a gentle gas evolution. The mixture was stirred for 20-30 min (pH ca. 10). The organic layer was separated and further washed with deionized water (3×540 mL). The organic layer was filtered through a pad of diatomaceous earth (10 g) and rinsed with EtOAc (270 mL). The combined organic layer was assayed by HPLC (contained 143.88 g of free base, 90% crude yield). The solution was diluted with absolute EtOH (270 mL). To the solution was slowly added a solution of concentrated aqueous HCl (0.95 eq. of the freebase based on HPLC assay; 36.73 g, 0.368 mol) in absolute ethanol (67 mL) and the resulting solution was stirred at rt (22-24° C.). After 20-30 min, the mixture became cloudy and the product crystallized slowly. After stirring at rt (22-24° C.) for 20-24 h, the solid product was collected by vacuum filtration. The filter cake was rinsed with EtOAc (540 mL) in several portions, and air-dried for 30 min. The damp filter cake was transferred to a glass dish and further dried in a vacuum oven at 50° C. for 20-24 h. $^1$H-NMR analysis of the solid product indicated the residual solvents were removed. The solid product was then re-hydrated in a sealed oven at rt in the presence of a satd. solution of ZnSO$_4$.7H$_2$O (100.0 g, 0.348 mol) in deionized water (200 mL) for 24-48 h to form the monohydrate. The product was isolated as white solid (125.0 g). Karl-Fisher analysis: ~4.25% water. mp: 143.4° C. (by DSC with closed pan). $^1$H NMR (d$^6$-DMSO): δ 11.40 (br s, 1H), 8.26 (s, 1H), 7.97 (br s, 1H), 7.24 (m, 4H), 7.11 (d, J=8.8 Hz, 1H), 4.12 (br m, 1H), 3.64 (br m, 3H), 3.36 (br m, 3H), 2.98 (br m, 2H), 2.44 (br m, 3H), 2.13 (br m, 3H), 1.66 (br m, 2H). MS (ESI): M+H$^+$=370.2.

Biological Methods:
H$_3$Receptor Binding (Human)

Binding of compounds to the cloned human H$_3$ receptors, stably expressed in SK-N-MC cells, was performed as described by Barbier, A. J. et al. (Br. J. Pharmacol. 2004, 143(5), 649-661). Data for compounds tested in this assay are presented in Table 1 as an average of the results obtained.

TABLE 1

| Ex# | Human H$_3$ K$_i$ (nM) |
|---|---|
| 1 | 29 |
| 2 | 56 |
| 3 | 66 |
| 4 | 56 |
| 5 | 71 |
| 6 | 32 |
| 7 | 57 |
| 8 | 68 |
| 9 | 11 |
| 10 | 10 |
| 11 | 7 |
| 12 | 5 |
| 13 | 6 |
| 14 | 2 |
| 15 | 8 |
| 16 | 2 |
| 17 | 5 |
| 18 | 2 |
| 19 | 4 |
| 20 | 1 |
| 21 | 2 |
| 22 | 180 |
| 23 | 3 |
| 24 | 1 |
| 25 | 1 |
| 26 | 1 |
| 27 | 4 |
| 28 | 13 |
| 29 | 1 |
| 30 | 1 |
| 31 | 4 |
| 32 | 4 |
| 33 | 1 |
| 34 | 5 |
| 35 | 3 |
| 36 | 1 |
| 37 | 5 |
| 38 | 6 |
| 39 | 1 |
| 40 | 1 |
| 41 | 4 |
| 42 | 12 |
| 43 | 299 |
| 44 | 327 |
| 45 | 34 |
| 46 | 202 |
| 47 | 357 |
| 48 | 67 |
| 49 | 115 |
| 50 | 18 |
| 51 | 2 |
| 52 | 4 |
| 53 | 49 |
| 54 | 104 |
| 55 | 21 |
| 56 | 5 |
| 57 | 3 |
| 58 | 10 |
| 59 | 3 |
| 60 | 29 |
| 61 | 6 |
| 62 | 36 |
| 63 | 32 |
| 64 | 165 |
| 65 | 2 |
| 66 | 1 |
| 67 | 2 |
| 68 | 2 |
| 69 | 2 |
| 70 | 2 |
| 71 | 2 |
| 72 | 2 |
| 73 | 4 |
| 74 | 7 |
| 75 | 9 |
| 76 | 19 |
| 77 | 22 |

TABLE 1-continued

| Ex# | Human H$_3$ K$_i$ (nM) |
|---|---|
| 78 | 24 |
| 79 | 10 |
| 80 | 253 |
| 81 | 3 |
| 82 | 1 |
| 83 | 1 |
| 84 | 2 |
| 85 | 1 |
| 86 | 1 |
| 87 | 98 |
| 88 | 59 |
| 89 | 28 |
| 90 | 19 |
| 91 | 3 |
| 92 | 250 |
| 93 | 58 |
| 94 | 3 |
| 95 | 1 |
| 96 | 1 |
| 97 | 1 |
| 98 | 19 |
| 99 | 28 |
| 100 | 98 |
| 101 | 59 |
| 102 | 1 |
| 103 | 1 |
| 104 | 2 |
| 105 | 11 |

H$_3$ Receptor Binding (Rat)

A rat brain without cerebellum (Zivic Laboratories Inc., Pittsburgh, Pa.) was homogenized in 50 mM Tris-HCl/5 mM EDTA and centrifuged at 1,000 rpm for 5 min. The supernatant was removed and recentrifuged at 15,000 rpm for 30 min. Pellets were rehomogenized in 50 mM Tris/5 mM EDTA (pH 7.4). Membranes were incubated with 0.8 nM N-[$^3$H]-α-methylhistamine plus/minus test compounds for 60 min at 25° C. and harvested by rapid filtration over GF/C glass fiber filters (pretreated with 0.3% polyethylenimine) followed by four washes with buffer. Nonspecific binding was defined in the presence of 100 μM histamine. Inhibitory concentration (responsible for 50% inhibition of maximal effect, IC$_{50}$) values were determined by a single site curve-fitting program (GraphPad, San Diego, Calif.) and converted to K$_i$ values based on a N-[$^3$H]-α-methylhistamine dissociation constant (K$_d$) of 0.8 nM. Data for compounds tested in this assay are presented in Table 2 as an average of the results obtained.

TABLE 2

| Ex# | Rat H$_3$ K$_i$ (nM) |
|---|---|
| 9 | 130 |
| 11 | 447 |
| 12 | 51 |
| 13 | 54 |
| 14 | 10 |
| 18 | 68 |
| 19 | 66 |
| 20 | 17 |
| 21 | 16 |
| 23 | 70 |
| 24 | 15 |
| 25 | 25 |
| 26 | 16 |
| 27 | 86 |
| 29 | 20 |
| 30 | 26 |
| 31 | 39 |
| 32 | 92 |

TABLE 2-continued

| Ex# | Rat H$_3$ K$_i$ (nM) |
|---|---|
| 36 | 30 |
| 37 | 130 |
| 39 | 21 |
| 40 | 36 |
| 41 | 75 |
| 51 | 60 |
| 52 | 110 |
| 56 | 179 |
| 57 | 132 |
| 84 | 37 |
| 102 | 17 |
| 105 | 32 |

Cyclic AMP Accumulation

Sublines of SK-N-MC cells were created that expressed a reporter construct and either the human or rat H$_3$ receptor. The pA$_2$ values were obtained as described by Barbier et al. (2004). Data for compounds tested in these assays are presented in Table 3, as an average of the results obtained (NT=not tested).

TABLE 3

| Ex# | Human pA$_2$ | Rat pA$_2$ |
|---|---|---|
| 9 | 8.06 | 7.35 |
| 11 | 8.53 | NT |
| 12 | 8.26 | NT |
| 14 | 9.26 | 8.16 |
| 19 | 9.38 | 8.48 |
| 24 | 9.15 | 8.36 |
| 25 | 9.22 | 8.42 |
| 26 | 9.64 | 8.67 |
| 29 | 9.09 | 8.45 |
| 30 | 9.27 | 8.38 |
| 31 | 8.62 | 8.12 |
| 39 | 9.40 | 8.38 |
| 40 | 8.88 | 7.87 |
| 51 | 8.64 | 7.66 |
| 56 | 8.63 | 7.86 |
| 59 | 8.51 | 7.57 |
| 61 | 8.44 | 7.49 |
| 65 | 8.94 | 9.18 |
| 66 | 8.95 | 7.94 |
| 67 | 8.87 | 8.17 |
| 68 | 8.61 | 7.80 |
| 70 | 8.72 | 7.72 |
| 73 | 9.51 | 8.92 |
| 74 | 8.05 | 7.44 |
| 83 | 9.48 | 8.49 |
| 86 | 9.48 | 8.50 |
| 95 | 9.48 | 8.50 |
| 97 | 9.48 | 8.49 |
| 102 | 9.70 | 8.92 |
| 104 | 9.14 | 8.37 |

NT = not tested

What is claimed is:

1. A pharmaceutical composition, comprising:
   (a) an effective amount of a compound of Formula (I):

wherein
R$^1$ is —C$_{1-4}$alkyl or saturated monocyclic cycloalkyl;
m is 1 or 2;
X is N or CH;
Y is N or CR$^a$;
   R$^a$ is —H, —Z—Ar, —CH$_2$NR$^b$R$^c$, —CN, —CO$_2$C$_{1-4}$alkyl, —CO$_2$H, or —CONR$^b$R$^c$; where R$^b$ and R$^c$ are each independently —H or —C$_{1-4}$alkyl; and
R$^2$ is —H or —Z—Ar;
with the proviso that one of X and Y is N and one of R$^a$ and R$^2$ is —Z—Ar;
   where Z is O or S; and
   Ar is a phenyl or monocyclic heteroaryl group unsubstituted or substituted with one, two, or three R$^3$ substituents;
      where each R$^3$ substituent is independently selected from the group consisting of: halo, —C$_{1-4}$alkyl, —OH, —OC$_{1-4}$alkyl, —SC$_{1-4}$alkyl, —CN, —CONR$^d$R$^e$, and —NO$_2$;
         where R$^d$ and R$^e$ are each independently —H or —C$_{1-4}$alkyl;
or a pharmaceutically acceptable salt, thereof; and
   (b) a pharmaceutically acceptable excipient.

2. A pharmaceutical composition according to claim 1, further comprising: an active ingredient selected from the group consisting of H$_1$ receptor antagonists, H$_2$ receptor antagonists, H$_3$ receptor antagonists, serotonin-norepinephrine reuptake inhibitors, selective serotonin reuptake inhibitors, noradrenergic reuptake inhibitors, non-selective serotonin re-uptake inhibitors, acetylcholinesterase inhibitors, and modafinil.

3. A pharmaceutical composition according to claim 1, further comprising topiramate.

4. A compound selected from the group consisting of:
[6-(3,4-Dichloro-phenoxy)-pyridin-3-yl]-(4-isopropyl-piperazin-1-yl)-methanone;
(4-Isopropyl-piperazin-1-yl)-[6-(pyridin-3-yloxy)-pyridin-3-yl]-methanone;
(4-Isopropyl-piperazin-1-yl)-[6-(4-methylsulfanyl-phenoxy)-pyridin-3-yl]-methanone;
[6-(3-Chloro-phenoxy)-pyridin-3-yl]-(4-isopropyl-piperazin-1-yl)-methanone;
(4-Isopropyl-piperazin-1-yl)-(6-phenoxy-pyridin-3-yl)-methanone;
[6-(4-Chloro-3-methyl-phenoxy)-pyridin-3-yl]-(4-isopropyl-piperazin-1-yl)-methanone;
3-[5-(4-Isopropyl-piperazine-1-carbonyl)-pyridin-2-yloxy]-benzonitrile;
[6-(4-Chloro-phenoxy)-pyridin-3-yl]-(4-isopropyl-piperazin-1-yl)-methanone;
(4-Cyclopropyl-[1,4]diazepan-1-yl)-[6-(3,4-dichloro-phenoxy)-pyridin-3-yl]-methanone;
[6-(4-Chloro-phenoxy)-pyridin-3-yl]-(4-cyclopropyl-[1,4]diazepan-1-yl)-methanone;
3-[5-(4-Cyclopropyl[1,4]diazepane-1-carbonyl)-pyridin-2-yloxy]-benzonitrile;
[6-(4-Chloro-3-methyl-phenoxy)-pyridin-3-yl]-(4-cyclopropyl-[1,4]diazepan-1-yl)-methanone;
(4-Cyclopropyl-[1,4]diazepan-1-yl)-(6-phenoxy-pyridin-3-yl)-methanone;
(4-Cyclobutyl-[1,4]diazepan-1-yl)-[6-(3,4-dichloro-phenoxy)-pyridin-3-yl]-methanone;
[6-(3,4-Dichloro-phenoxy)-pyridin-3-yl]-(4-isopropyl-[1,4]diazepan-1-yl)-methanone;
[6-(4-Chloro-3-methyl-phenoxy)-pyridin-3-yl]-(4-cyclobutyl-[1,4]diazepan-1-yl)-methanone;
[6-(4-Chloro-3-methyl-phenoxy)-pyridin-3-yl]-(4-isopropyl-[1,4]diazepan-1-yl)-methanone;

(4-Cyclopropyl-[1,4]diazepan-1-yl)-[6-(4-fluoro-phenoxy)-pyridin-3-yl]-methanone;
(4-Cyclobutyl-[1,4]diazepan-1-yl)-[6-(4-fluoro-phenoxy)-pyridin-3-yl]-methanone;
3-[5-(4-Cyclobutyl-[1,4]diazepane-1-carbonyl)-pyridin-2-yloxy]-benzonitrile;
(4-Cyclobutyl-[1,4]diazepan-1-yl)-(6-phenoxy-pyridin-3-yl)-methanone;
(4-Cyclopropyl-piperazin-1-yl)-[6-(4-fluoro-phenoxy)-pyridin-3-yl]-methanone;
[6-(3-Chloro-phenoxy)-pyridin-3-yl]-(4-cyclopropyl-[1,4]diazepan-1-yl)-methanone;
[6-(3-Chloro-phenoxy)-pyridin-3-yl]-(4-cyclobutyl-[1,4]diazepan-1-yl)-methanone;
[6-(4-Chloro-phenoxy)-pyridin-3-yl]-(4-cyclobutyl-[1,4]diazepan-1-yl)-methanone;
(4-Cyclobutyl-[1,4]diazepan-1-yl)-[6-(3,4-difluoro-phenoxy)-pyridin-3-yl]-methanone;
(4-Cyclopropyl-[1,4]diazepan-1-yl)-[6-(3,4-difluoro-phenoxy)-pyridin-3-yl]-methanone;
[6-(3,4-Difluoro-phenoxy)-pyridin-3-yl]-(4-isopropyl-piperazin-1-yl)-methanone;
(4-Cyclobutyl-[1,4]diazepan-1-yl)-[6-(2-fluoro-phenoxy)-pyridin-3-yl]-methanone;
(4-Cyclobutyl-[1,4]diazepan-1-yl)-[6-(2,4-difluoro-phenoxy)-pyridin-3-yl]-methanone;
(4-Cyclopropyl-[1,4]diazepan-1-yl)-[6-(2-fluoro-phenoxy)-pyridin-3-yl]-methanone;
(4-Cyclopropyl-[1,4]diazepan-1-yl)-[6-(2,4-difluoro-phenoxy)-pyridin-3-yl]-methanone;
(4-Cyclobutyl-[1,4]diazepan-1-yl)-[6-(3,5-dichloro-phenoxy)-pyridin-3-yl]-methanone;
(4-Cyclopropyl-[1,4]diazepan-1-yl)-[6-(2,5-difluoro-phenoxy)-pyridin-3-yl]-methanone;
(4-Cyclopropyl-[1,4]diazepan-1-yl)-[6-(3,5-dichloro-phenoxy)-pyridin-3-yl]-methanone;
(4-Cyclobutyl-[1,4]diazepan-1-yl)-[6-(3,5-difluoro-phenoxy)-pyridin-3-yl]-methanone;
(4-Cyclopropyl-[1,4]diazepan-1-yl)-[6-(3-fluoro-phenoxy)-pyridin-3-yl]-methanone;
[6-(3-Fluoro-phenoxy)-pyridin-3-yl]-(4-isopropyl-[1,4]diazepan-1-yl)-methanone;
(4-Cyclobutyl-[1,4]diazepan-1-yl)-[6-(3-fluoro-phenoxy)-pyridin-3-yl]-methanone;
(4-Cyclobutyl-[1,4]diazepan-1-yl)-[6-(3-methyl-4-methylsulfanyl-phenoxy)-pyridin-3-yl]-methanone;
(4-Cyclopropyl-[1,4]diazepan-1-yl)-[6-(3-methyl-4-methylsulfanyl-phenoxy)-pyridin-3-yl]-methanone;
(4-Isopropyl-[1,4]diazepan-1-yl)-[6-(3-methyl-4-methylsulfanyl-phenoxy)-pyridin-3-yl]-methanone;
[6-(3,4-Dichloro-phenoxy)-pyridin-2-yl]-(4-isopropyl-piperazin-1-yl)-methanone;
(4-Cyclopropyl-[1,4]diazepan-1-yl)-[6-(3,4-dichloro-phenoxy)-pyridin-2-yl]-methanone;
(4-Cyclobutyl-[1,4]diazepan-1-yl)-[6-(3,4-dichloro-phenoxy)-pyridin-2-yl]-methanone;
[6-(3,4-Dichloro-phenoxy)-pyridin-2-yl]-(4-isopropyl-[1,4]diazepan-1-yl)-methanone;
[6-(4-Chloro-3-methyl-phenoxy)-pyridin-2-yl]-(4-cyclopropyl-[1,4]diazepan-1-yl)-methanone;
[6-(4-Chloro-3-methyl-phenoxy)-pyridin-2-yl]-(4-cyclobutyl-[1,4]diazepan-1-yl)-methanone;
[6-(4-Chloro-3-methyl-phenoxy)-pyridin-2-yl]-(4-isopropyl-[1,4]diazepan-1-yl)-methanone;
[5-(3,4-Dichloro-phenoxy)-pyridin-2-yl]-(4-isopropyl-[1,4]diazepan-1-yl)-methanone;
(4-Cyclobutyl-[1,4]diazepan-1-yl)-[5-(3,4-dichloro-phenoxy)-pyridin-2-yl]-methanone;
(4-Cyclopropyl-[1,4]diazepan-1-yl)-[5-(3,4-dichloro-phenoxy)-pyridin-2-yl]-methanone;
3-(3,4-Dichloro-phenoxy)-6-(4-isopropyl-piperazine-1-carbonyl)-pyridine-2-carbonitrile;
3-(3,4-Dichloro-phenoxy)-6-(4-isopropyl-piperazine-1-carbonyl)-pyridine-2-carboxylic acid amide;
6-(4-Cyclopropyl-[1,4]diazepane-1-carbonyl)-3-(4-methylsulfanyl-phenoxy)-pyridine-2-carbonitrile;
6-(4-Cyclopropyl-[1,4]diazepane-1-carbonyl)-3-(pyridin-3-yloxy)-pyridine-2-carbonitrile;
3-(4-Chloro-3-methyl-phenoxy)-6-(4-cyclopropyl-[1,4]diazepane-1-carbonyl)-pyridine-2-carbonitrile;
6-(4-Cyclopropyl-[1,4]diazepane-1-carbonyl)-3-(3,4-dichloro-phenoxy)-pyridine-2-carbonitrile;
6-(4-Cyclopropyl-[1,4]diazepane-1-carbonyl)-3-(4-fluoro-phenoxy)-pyridine-2-carbonitrile;
6-(4-Cyclopropyl-[1,4]diazepane-1-carbonyl)-3-(3-fluoro-phenoxy)-pyridine-2-carbonitrile;
6-(4-Cyclopropyl-[1,4]diazepane-1-carbonyl)-3-(2-fluoro-phenoxy)-pyridine-2-carbonitrile;
6-(4-Cyclopropyl-[1,4]diazepane-1-carbonyl)-3-(4-methylsulfanyl-phenoxy)-pyridine-2-carboxylic acid amide;
6-(4-Cyclopropyl-[1,4]diazepane-1-carbonyl)-3-(pyridin-3-yloxy)-pyridine-2-carboxylic acid amide;
[6-Aminomethyl-5-(3,4-dichloro-phenoxy)-pyridin-2-yl]-(4-isopropyl-piperazin-1-yl)-methanone;
(4-Cyclopentyl-[1,4]diazepan-1-yl)-(6-phenoxy-pyridin-3-yl)-methanone;
(4-Cyclopentyl-[1,4]diazepan-1-yl)-[6-(3,4-dichloro-phenoxy)-pyridin-3-yl]-methanone;
(4-Cyclopentyl-[1,4]diazepan-1-yl)-[6-(4-fluoro-phenoxy)-pyridin-3-yl]-methanone;
[5-(4-Chloro-phenoxy)-pyridin-2-yl]-(4-cyclobutyl-[1,4]diazepan-1-yl)-methanone;
(4-Cyclobutyl-[1,4]diazepan-1-yl)-[5-(4-fluoro-phenoxy)-pyridin-2-yl]-methanone;
[5-(3-Chloro-phenoxy)-pyridin-2-yl]-(4-cyclobutyl-[1,4]diazepan-1-yl)-methanone;
(4-Cyclobutyl-[1,4]diazepan-1-yl)-[5-(3-fluoro-phenoxy)-pyridin-2-yl]-methanone;
(4-Cyclobutyl-[1,4]diazepan-1-yl)-[5-(2-fluoro-phenoxy)-pyridin-2-yl]-methanone;
[6-(2-Chloro-phenoxy)-pyridin-3-yl]-(4-cyclobutyl-[1,4]diazepan-1-yl)-methanone;
(4-Cyclopentyl-piperazin-1-yl)-[6-(4-fluoro-phenoxy)-pyridin-3-yl]-methanone;
[6-(2-Chloro-phenoxy)-pyridin-3-yl]-(4-isopropyl-piperazin-1-yl)-methanone;
[6-(2-Chloro-phenoxy)-pyridin-3-yl]-(4-cyclopentyl-piperazin-1-yl)-methanone;
[6-(4-Chloro-phenoxy)-pyridin-3-yl]-(4-cyclopentyl-piperazin-1-yl)-methanone;
(4-Cyclopentyl-piperazin-1-yl)-[6-(2-fluoro-phenoxy)-pyridin-3-yl]-methanone;
(4-Cyclobutyl-piperazin-1-yl)-[6-(4-fluoro-phenoxy)-pyridin-3-yl]-methanone;
[6-(4-Fluoro-phenoxy)-pyridin-3-yl]-(4-methyl-[1,4]diazepan-1-yl)-methanone;
6-(4-Cyclopropyl-[1,4]diazepane-1-carbonyl)-3-phenoxy-pyridine-2-carbonitrile;
6-(4-Cyclobutyl-[1,4]diazepane-1-carbonyl)-3-(4-fluoro-phenoxy)-pyridine-2-carbonitrile;
(4-Cyclobutyl-[1,4]diazepan-1-yl)-[6-(4-fluoro-phenylsulfanyl)-pyridin-3-yl]-methanone;

(4-Cyclobutyl-[1,4]diazepan-1-yl)-[5-(4-fluoro-phenyl-sulfanyl)-pyridin-2-yl]-methanone;
[6-(4-Chloro-phenylsulfanyl)-pyridin-3-yl]-(4-cyclobutyl-[1,4]diazepan-1-yl)-methanone;
(4-Cyclobutyl-[1,4]diazepan-1-yl)-(6-phenylsulfanyl-pyridin-3-yl)-methanone;
(4-Cyclopentyl-piperazin-1-yl)-[6-(3-methyl-4-methylsulfanyl-phenoxy)-pyridin-3-yl]-methanone;
(4-Isopropyl-piperazin-1-yl)-[6-(3-methyl-4-methylsulfanyl-phenoxy)-pyridin-3-yl]-methanone;
[6-(4-Fluoro-phenoxy)-pyridin-3-yl]-(4-isopropyl-piperazin-1-yl)-methanone;
(4-Ethyl-[1,4]diazepan-1-yl)-[6-(4-fluoro-phenoxy)-pyridin-3-yl]-methanone;
(4-Cyclobutyl-[1,4]diazepan-1-yl)-(5-phenylsulfanyl-pyridin-2-yl)-methanone;
[6-(4-Fluoro-phenoxy)-pyridin-3-yl]-(4-methyl-[1,4]diazepan-1-yl)-methanone;
[6-(4-Fluoro-phenoxy)-pyridin-3-yl]-(4-isobutyl-piperazin-1-yl)-methanone;
(4-Cyclobutyl-[1,4]diazepan-1-yl)-(5-phenylsulfanyl-pyridin-2-yl)-methanone;
(4-Cyclobutyl-[1,4]diazepan-1-yl)-(6-phenylsulfanyl-pyridin-3-yl)-methanone;
[6-(4-Chloro-phenylsulfanyl)-pyridin-3-yl]-(4-cyclobutyl-[1,4]diazepan-1-yl)-methanone;
(4-Cyclobutyl-[1,4]diazepan-1-yl)-[6-(4-fluoro-phenylsulfanyl)-pyridin-3-yl]-methanone;
(4-Ethyl-[1,4]diazepan-1-yl)-[6-(4-fluoro-phenoxy)-pyridin-3-yl]-methanone;
[6-(4-Fluoro-phenoxy)-pyridin-3-yl]-(4-isopropyl-piperazin-1-yl)-methanone;
(4-Cyclopentyl-piperazin-1-yl)-[6-(3-methyl-4-methylsulfanyl-phenoxy)-pyridin-3-yl]-methanone;
(4-Isopropyl-piperazin-1-yl)-[6-(3-methyl-4-methylsulfanyl-phenoxy)-pyridin-3-yl]-methanone;
(4-Cyclobutyl-[1,4]diazepan-1-yl)-(6-o-tolyloxy-pyridin-3-yl)-methanone;
(4-Cyclobutyl-[1,4]diazepan-1-yl)-(6-m-tolyloxy-pyridin-3-yl)-methanone;
(4-Cyclobutyl-[1,4]diazepan-1-yl)-(6-p-tolyloxy-pyridin-3-yl)-methanone; and
(4-Cyclobutyl-[1,4]diazepan-1-yl)-[6-(4-methylsulfanyl-phenoxy)-pyridin-3-yl]-methanone;
and monohydrochloride monohydrates thereof.

* * * * *